(12) United States Patent
Wieland et al.

(10) Patent No.: US 12,291,696 B2
(45) Date of Patent: *May 6, 2025

(54) CLEANING COMPOSITIONS CONTAINING DISPERSINS III

(71) Applicant: Henkel AG & Co. KGaA, Duesseldorf (DE)

(72) Inventors: Susanne Wieland, Dormagen/Zons (DE); Stefan Karsten, Gummersbach (DE); Thomas Weber, Weimar (DE); Regina Stehr, Neuss (DE); Marianne Schmeling, Korschenbroich (DE); Michael Dreja, Neuss (DE); Mirko Weide, Duesseldorf (DE); Christian Oehlenschlaeger, Valby (DK); Dorotea Raventos Segura, Rungsted (DK); Rebecca Vejborg, Alleroed (DK); Henrik Geertz-Hansen, Copenhagen (DK); Lilian Baltsen, Bagsvaerd (DK); Jesper Salomon, Holte (DK)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/760,454

(22) PCT Filed: Oct. 31, 2018

(86) PCT No.: PCT/EP2018/079845
§ 371 (c)(1),
(2) Date: Apr. 30, 2020

(87) PCT Pub. No.: WO2019/086526
PCT Pub. Date: May 9, 2019

(65) Prior Publication Data
US 2020/0347324 A1    Nov. 5, 2020

(30) Foreign Application Priority Data
Nov. 1, 2017  (DE) .................... 10 2017 125 560.5

(51) Int. Cl.
*C12N 9/24* (2006.01)
*C11D 1/94* (2006.01)
(Continued)

(52) U.S. Cl.
CPC ............ *C11D 3/38636* (2013.01); *C11D 1/94* (2013.01); *C11D 3/0005* (2013.01); *C11D 3/001* (2013.01); *C11D 3/0036* (2013.01); *C11D 3/1246* (2013.01); *C11D 3/128* (2013.01); *C11D 3/2082* (2013.01); *C11D 3/225* (2013.01); *C11D 3/30* (2013.01); *C11D 3/361* (2013.01); *C11D 3/3723* (2013.01); *C11D 3/373* (2013.01); *C11D 3/3757* (2013.01); *C11D 3/381* (2013.01); *C11D 3/3951* (2013.01); *C11D 3/42* (2013.01); *C11D 3/43* (2013.01); *C11D 3/48* (2013.01); *C11D 3/50* (2013.01); *C12N 9/2402* (2013.01); *C12Y 302/0105* (2013.01);
(Continued)

(58) Field of Classification Search
CPC ..... C11D 3/38636; C11D 1/94; C11D 3/0005; C11D 3/001; C11D 3/0036; C11D 3/1246; C11D 3/128; C11D 3/2082; C11D 3/225; C11D 3/30; C11D 3/361; C11D 3/3723; C11D 3/373; C11D 3/3757; C11D 3/381; C11D 3/3951; C11D 3/42; C11D 3/43; C11D 3/48; C11D 3/50; C11D 11/0017; C11D 11/0023; C11D 1/62; C11D 1/66; C11D 3/2065; C11D 3/2068; C11D 3/2086; C11D 3/227; C11D 3/33; C11D 3/37; C11D 3/3707; C11D 3/3769; C11D 3/378; C11D 3/38645; C11D 3/38672; C11D 3/3905; C11D 17/043; C12N 9/2402; C12Y 302/0105; C12Y 302/01052; C12Y 302/01096; D06M 16/003

See application file for complete search history.

(56) References Cited

U.S. PATENT DOCUMENTS

| | | |
|---|---|---|
| 4,106,991 A | 8/1978 | Markussen et al. |
| 4,435,307 A | 3/1984 | Barbesgaard et al. |

(Continued)

FOREIGN PATENT DOCUMENTS

| | | |
|---|---|---|
| AU | 6559390 A | 5/1991 |
| CA | 2202553 A1 | 4/1996 |

(Continued)

OTHER PUBLICATIONS

Witkowski et al., Biochemistry 38:11643-11650, 1999.*

(Continued)

*Primary Examiner* — Delia M Ramirez
(74) *Attorney, Agent, or Firm* — CANTOR COLBURN LLP

(57) ABSTRACT

Cleaning compositions may include at least 0.001 ppm of a polypeptide having hexosaminidase activity. The cleaning compositions may include a polypeptide having at least 60% sequence identity to the mature polypeptide shown in one or more of the motif(s) of SEQ ID NO 7, SEQ ID 8, SEQ ID 9, SEQ ID 10, SEQ ID 11, or combinations thereof. The cleaning compositions may be or include laundry detergents, fabric finishers, acidic cleaning agents, neutral cleaning agents, alkaline cleaning agents, hand dishwashing agents, automatic dishwasher compositions, or combinations thereof.

11 Claims, 3 Drawing Sheets
Specification includes a Sequence Listing.

(51) Int. Cl.

| | |
|---|---|
| C11D 3/00 | (2006.01) |
| C11D 3/12 | (2006.01) |
| C11D 3/20 | (2006.01) |
| C11D 3/22 | (2006.01) |
| C11D 3/30 | (2006.01) |
| C11D 3/36 | (2006.01) |
| C11D 3/37 | (2006.01) |
| C11D 3/38 | (2006.01) |
| C11D 3/386 | (2006.01) |
| C11D 3/395 | (2006.01) |
| C11D 3/42 | (2006.01) |
| C11D 3/43 | (2006.01) |
| C11D 3/48 | (2006.01) |
| C11D 3/50 | (2006.01) |

(52) U.S. Cl.
CPC .............. *C12Y 302/01052* (2013.01); *C12Y 302/01096* (2013.01); *C11D 2111/12* (2024.01); *C11D 2111/14* (2024.01)

(56) References Cited

U.S. PATENT DOCUMENTS

| | | | |
|---|---|---|---|
| 4,661,452 | A | 4/1987 | Markussen et al. |
| 4,664,839 | A | 5/1987 | Rieck |
| 5,352,604 | A | 10/1994 | Wilson et al. |
| 5,389,536 | A | 2/1995 | Gray et al. |
| 5,453,372 | A | 9/1995 | Vetter et al. |
| 5,457,046 | A | 10/1995 | Woeldike et al. |
| 5,648,263 | A | 7/1997 | Schuelein et al. |
| 5,686,593 | A | 11/1997 | Woeldike et al. |
| 5,691,178 | A | 11/1997 | Schuelein et al. |
| 5,763,254 | A | 6/1998 | Woeldike et al. |
| 5,776,757 | A | 7/1998 | Schuelein et al. |
| 5,827,718 | A | 10/1998 | Ishida et al. |
| 5,888,954 | A | 3/1999 | Haerer et al. |
| 5,942,431 | A | 8/1999 | Yoneda et al. |
| 5,977,053 | A | 11/1999 | Groth et al. |
| 6,197,589 | B1 | 3/2001 | Maurer et al. |
| 6,218,165 | B1 | 4/2001 | Estell et al. |
| 6,313,081 | B1 | 11/2001 | Lenting et al. |
| 6,461,849 | B1 | 10/2002 | Olsen et al. |
| 6,465,410 | B1 | 10/2002 | Bettiol et al. |
| 6,468,955 | B1* | 10/2002 | Smets .............. C11D 3/38681 510/276 |
| 6,566,114 | B1 | 5/2003 | Kauppinen et al. |
| 7,062,042 | B1 | 6/2006 | Gilbert |
| 7,262,042 | B2 | 8/2007 | Weber et al. |
| 7,993,898 | B2 | 8/2011 | Andersen et al. |
| 8,202,831 | B2 | 6/2012 | Lant et al. |
| 8,399,235 | B2 | 3/2013 | Frank et al. |
| 8,821,862 | B2 | 9/2014 | Madhyastha et al. |
| 10,030,239 | B2 | 7/2018 | Gjermansen |
| 2008/0153983 | A1 | 6/2008 | Boeckh et al. |
| 2009/0011970 | A1 | 1/2009 | Evers |
| 2009/0155215 | A1 | 6/2009 | Collins et al. |
| 2011/0196319 | A1 | 8/2011 | Arscott, II et al. |
| 2012/0258089 | A1 | 10/2012 | Madhyastha et al. |
| 2014/0080178 | A1* | 3/2014 | Schnorr .............. C12N 9/2434 435/69.1 |
| 2014/0295522 | A1 | 10/2014 | Mussmann et al. |
| 2016/0017304 | A1 | 1/2016 | Cascao-Pereira et al. |
| 2017/0240877 | A1 | 8/2017 | Andersen et al. |
| 2017/0355931 | A1 | 12/2017 | Lant et al. |
| 2017/0355933 | A1 | 12/2017 | Lant et al. |
| 2018/0155802 | A1 | 6/2018 | Lant |
| 2019/0127663 | A1 | 5/2019 | Oehlenschlaeger et al. |
| 2019/0153417 | A1 | 5/2019 | Adams et al. |
| 2019/0161707 | A1 | 5/2019 | Vejborg et al. |
| 2019/0169547 | A1 | 6/2019 | Ooehlenschlaeger et al. |
| 2019/0284511 | A1 | 9/2019 | Oehlenschlaeger et al. |
| 2021/0222089 | A1 | 7/2021 | Blackman et al. |

FOREIGN PATENT DOCUMENTS

| | | |
|---|---|---|
| CN | 109415665 A | 3/2019 |
| EP | 0164514 A1 | 12/1985 |
| EP | 0179486 A2 | 4/1986 |
| EP | 0218272 A1 | 4/1987 |
| EP | 0238216 A1 | 9/1987 |
| EP | 0258068 A2 | 3/1988 |
| EP | 0305216 A1 | 3/1989 |
| EP | 0331376 A2 | 9/1989 |
| EP | 0407225 A1 | 1/1991 |
| EP | 0495257 A1 | 7/1992 |
| EP | 0531372 B1 | 2/1995 |
| EP | 0531315 B1 | 3/1997 |
| EP | 0624154 B1 | 9/1999 |
| EP | 1867708 A1 | 12/2007 |
| EP | 1876226 A1 | 1/2008 |
| EP | 1921147 A2 | 5/2008 |
| EP | 1921148 A2 | 5/2008 |
| EP | 2169040 A1 | 3/2010 |
| EP | 3088506 A1 | 11/2016 |
| EP | 3309244 A1 | 4/2018 |
| EP | 3330353 A1 | 6/2018 |
| EP | 3034596 B1 | 8/2018 |
| EP | 2516606 B1 | 1/2019 |
| EP | 3533859 A1 | 9/2019 |
| EP | 3647397 A1 | 5/2020 |
| EP | 3647398 A1 | 5/2020 |
| GB | 1296839 A | 11/1972 |
| GB | 1483591 A | 8/1977 |
| JP | H02238885 A | 9/1990 |
| JP | H07143883 A | 6/1995 |
| JP | 2000210081 A | 8/2000 |
| JP | 2005247981 A | 9/2005 |
| WO | 8906279 A1 | 7/1989 |
| WO | 8909259 A1 | 10/1989 |
| WO | 9102792 A1 | 3/1991 |
| WO | 9117243 A1 | 11/1991 |
| WO | 9117244 A1 | 11/1991 |
| WO | 9201046 A1 | 1/1992 |
| WO | 9205249 A1 | 4/1992 |
| WO | 9219729 A1 | 11/1992 |
| WO | 9221760 A1 | 12/1992 |
| WO | 9307263 A2 | 4/1993 |
| WO | 9318140 A1 | 9/1993 |
| WO | 9324618 A1 | 12/1993 |
| WO | 9401541 A1 | 1/1994 |
| WO | 9402597 A1 | 2/1994 |
| WO | 9407998 A1 | 4/1994 |
| WO | 9418314 A1 | 8/1994 |
| WO | 9425578 A1 | 11/1994 |
| WO | 9425583 A1 | 11/1994 |
| WO | 9426859 A1 | 11/1994 |
| WO | 9426860 A1 | 11/1994 |
| WO | 9506720 A1 | 3/1995 |
| WO | 9510602 A1 | 4/1995 |
| WO | 9510603 A1 | 4/1995 |
| WO | 9514783 A1 | 6/1995 |
| WO | 9522615 A1 | 8/1995 |
| WO | 9523221 A1 | 8/1995 |
| WO | 9524471 A1 | 9/1995 |
| WO | 9527046 A2 | 10/1995 |
| WO | 9530744 A2 | 11/1995 |
| WO | 9533836 A1 | 12/1995 |
| WO | 9535381 A1 | 12/1995 |
| WO | 9600292 A1 | 1/1996 |
| WO | 9611262 A1 | 4/1996 |
| WO | 9612012 A1 | 4/1996 |
| WO | 9613580 A1 | 5/1996 |
| WO | 9623873 A1 | 8/1996 |
| WO | 9627002 A1 | 9/1996 |
| WO | 9629397 A1 | 9/1996 |
| WO | 9634946 A1 | 11/1996 |
| WO | 9704079 A1 | 2/1997 |
| WO | 9704102 A1 | 2/1997 |
| WO | 9707202 A1 | 2/1997 |
| WO | 9708325 A2 | 3/1997 |
| WO | 9723606 A1 | 7/1997 |
| WO | 9743424 A1 | 11/1997 |

(56) References Cited

FOREIGN PATENT DOCUMENTS

| | | |
|---|---|---|
| WO | 9808940 A1 | 3/1998 |
| WO | 9812307 A1 | 3/1998 |
| WO | 9815257 A1 | 4/1998 |
| WO | 9817767 A1 | 4/1998 |
| WO | 9820115 A1 | 5/1998 |
| WO | 9820116 A1 | 5/1998 |
| WO | 9850512 A1 | 11/1998 |
| WO | 9901544 A1 | 1/1999 |
| WO | 9911768 A1 | 3/1999 |
| WO | 9919467 A1 | 4/1999 |
| WO | 9932595 A1 | 7/1999 |
| WO | 9957155 A1 | 11/1999 |
| WO | 9957157 A1 | 11/1999 |
| WO | 9964619 A2 | 12/1999 |
| WO | 0001793 A1 | 1/2000 |
| WO | 0034450 A1 | 6/2000 |
| WO | 0060063 A1 | 10/2000 |
| WO | 0116285 A2 | 3/2001 |
| WO | 0144452 A1 | 6/2001 |
| WO | 0162903 A1 | 8/2001 |
| WO | 0166712 A2 | 9/2001 |
| WO | 0179458 A2 | 10/2001 |
| WO | 0179459 A2 | 10/2001 |
| WO | 0179460 A2 | 10/2001 |
| WO | 0179461 A2 | 10/2001 |
| WO | 0192502 A1 | 12/2001 |
| WO | 0210355 A2 | 2/2002 |
| WO | 0216547 A2 | 2/2002 |
| WO | 02099091 A2 | 12/2002 |
| WO | 03006602 A2 | 1/2003 |
| WO | 03040279 A1 | 5/2003 |
| WO | 2004003186 A2 | 1/2004 |
| WO | 2004041979 A2 | 5/2004 |
| WO | 2004061117 A2 | 7/2004 |
| WO | 2004067737 A2 | 8/2004 |
| WO | 2005003274 A1 | 1/2005 |
| WO | 2005003275 A1 | 1/2005 |
| WO | 2005003276 A1 | 1/2005 |
| WO | 2005040372 A1 | 5/2005 |
| WO | 2005052146 A2 | 6/2005 |
| WO | 2005052161 A2 | 6/2005 |
| WO | 2005056782 A2 | 6/2005 |
| WO | 2006031554 A2 | 3/2006 |
| WO | 2006034710 A1 | 4/2006 |
| WO | 2006066594 A2 | 6/2006 |
| WO | 2006108856 A2 | 10/2006 |
| WO | 2006113314 A1 | 10/2006 |
| WO | 2006130575 A2 | 12/2006 |
| WO | 2007006305 A1 | 1/2007 |
| WO | 2007044993 A2 | 4/2007 |
| WO | 2007087242 A2 | 8/2007 |
| WO | 2007087243 A2 | 8/2007 |
| WO | 2007087244 A2 | 8/2007 |
| WO | 2007087257 A2 | 8/2007 |
| WO | 2007087258 A2 | 8/2007 |
| WO | 2007087259 A2 | 8/2007 |
| WO | 2007087508 A2 | 8/2007 |
| WO | 2007138054 A1 | 12/2007 |
| WO | 2008043175 A1 | 4/2008 |
| WO | 2008153815 A2 | 12/2008 |
| WO | 2008157350 A2 | 12/2008 |
| WO | 2009021867 A2 | 2/2009 |
| WO | 2009043709 A1 | 4/2009 |
| WO | 2009061380 A1 | 5/2009 |
| WO | 2009067279 A1 | 5/2009 |
| WO | 2009087523 A2 | 7/2009 |
| WO | 2009102854 A1 | 8/2009 |
| WO | 2009109500 A1 | 9/2009 |
| WO | 2009/121183 A1 | 10/2009 |
| WO | 2010065455 A2 | 6/2010 |
| WO | 2010100028 A2 | 9/2010 |
| WO | 2010104675 A1 | 9/2010 |
| WO | 2010107560 A2 | 9/2010 |
| WO | 2010111143 A2 | 9/2010 |
| WO | 2011036263 A1 | 3/2011 |
| WO | 2011036264 A1 | 3/2011 |
| WO | 2011084412 A1 | 7/2011 |
| WO | 2011084417 A1 | 7/2011 |
| WO | 2011084599 A1 | 7/2011 |
| WO | 2011098531 A1 | 8/2011 |
| WO | 2011150157 A2 | 12/2011 |
| WO | 2011163325 A1 | 12/2011 |
| WO | 2012/129515 A1 | 9/2012 |
| WO | 2012137147 A1 | 10/2012 |
| WO | 2013001078 A1 | 1/2013 |
| WO | 2013001087 A2 | 1/2013 |
| WO | 2013016368 A1 | 1/2013 |
| WO | 2013060621 A1 | 5/2013 |
| WO | 2013087545 A1 | 6/2013 |
| WO | 2013184577 A1 | 12/2013 |
| WO | 2013188331 A1 | 12/2013 |
| WO | 2014110675 A1 | 7/2014 |
| WO | 2014124927 A2 | 8/2014 |
| WO | 2014207227 A1 | 12/2014 |
| WO | 2015014790 A2 | 2/2015 |
| WO | 2015014803 A1 | 2/2015 |
| WO | 2015014804 A1 | 2/2015 |
| WO | 2015040159 A2 | 3/2015 |
| WO | 2015158723 A1 | 10/2015 |
| WO | 2015196299 A1 | 12/2015 |
| WO | 2016001449 A1 | 1/2016 |
| WO | 2016075078 A2 | 5/2016 |
| WO | 2016087617 A1 | 6/2016 |
| WO | 2016096711 A2 | 6/2016 |
| WO | 2016096714 A1 | 6/2016 |
| WO | 2016097350 A1 | 6/2016 |
| WO | 2016097352 A1 | 6/2016 |
| WO | 2016097354 A1 | 6/2016 |
| WO | 2016097357 A1 | 6/2016 |
| WO | 2016174234 A2 | 11/2016 |
| WO | 2016176240 A1 | 11/2016 |
| WO | 2016176241 A1 | 11/2016 |
| WO | 2016176280 A1 | 11/2016 |
| WO | 2017021515 A1 | 2/2017 |
| WO | 2017021516 A1 | 2/2017 |
| WO | 2017021517 A1 | 2/2017 |
| WO | 2017021518 A1 | 2/2017 |
| WO | 2017079751 A1 | 5/2017 |
| WO | 2017097866 A1 | 6/2017 |
| WO | 2017156098 A1 | 9/2017 |
| WO | 2017186936 A1 | 11/2017 |
| WO | 2017186937 A1 | 11/2017 |
| WO | 2017186943 A1 | 11/2017 |
| WO | 2017207770 A1 | 12/2017 |
| WO | 2017210295 A1 | 12/2017 |
| WO | 2017214240 A2 | 12/2017 |
| WO | 2018002194 A1 | 1/2018 |
| WO | 2018085524 A2 | 5/2018 |
| WO | 2018102478 A1 | 6/2018 |
| WO | 2018184816 A1 | 10/2018 |
| WO | 2018184873 A1 | 10/2018 |
| WO | 2019086520 A1 | 5/2019 |
| WO | 2019086521 A1 | 5/2019 |
| WO | 2019086526 A1 | 5/2019 |
| WO | 2019086528 A1 | 5/2019 |
| WO | 2019086530 A1 | 5/2019 |
| WO | 2020007863 A1 | 1/2020 |
| WO | 2020007875 A1 | 1/2020 |
| WO | 2021122117 A1 | 6/2021 |

OTHER PUBLICATIONS

Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Varghese, N., GenBank accession No. SEN27755, published Oct. 29, 2016.*
Wang et al., UniProt accession No. A0A075LPR4_9BACI, published Oct. 29, 2014.*

(56) References Cited

OTHER PUBLICATIONS

International search report from parallel PCT Patent Application PCT/EP2018/079845 dated Feb. 28, 2019, 16 pages (for reference purposes only).
"SubName: Full=Uncharacterized protein {ECO:0000313| EMBL:AIF67972.1}", Uniprot, Oct. 29, 2014, 1 page.
"SubName: Full=Beta-hexosaminidase {ECO:0000313|EMBL: KKI62758.1};", Uniprot, Nov. 11, 2015, 1 page.
Andrew, 2016, Uniprot accession No. A0A0Q5CMZ8.
Andrew, 2016, Uniprot accession No. A0A0Q5KJC4.
Anonymous, 2013, NCBI No. WP_005560708.
Anonymous, 2013, NCBI No. WP_017886882.1.
Anonymous, 2013, NCBI No. WP_018652103.
Anonymous, 2015, NCBI No. WP_051596815.1.
Durkin et al, 2012, EBI Accession No. J4TU99.
Gillaspy et al, 2014, EBI Accession No. X2JMQ1.
Jackson et al, 2011, EBI Accession No. P86956.
Joubert et al, 2012, EBI Accession No. H2A0L6.
Kaplan et al, 2003, J Bacteriol 185(16), 4693-4698.
Kaplan et al, 2004, EBI Accession No. Q6GYA5.
Keeling et al, 2013, Uniprot accession No. U4URB2.
Liu et al, 2010, Int Sys Evol Microbiol 60, 2940-2945.
Macinnes et al, 2012, EBI Accession No. K0G581.
Macinnes et al, 2015, EBI Accession No. A0A0A7IMHS5.
Mckinlay et al, 2016, Uniprot accession No. A6VMN2.
Ramasubbu et al, 2005, J Mol Biol 349(3), 475-486.
Tews et al, 1998, EBI Accession No. Q54468.
Ward et al, 2016, Uniprot accession No. D7N318.
Weinstock et al, 2015, Uniprot accession No. E4HHI5.
Zhan et al, 2015, Uniprot accession No. D9PAB0.
Uniprot Protein Database, protein Accession A0A5D0EMY6_AGGAC, Beta-N-acetylhexosaminidase, accessed on Sep. 8, 2021.
Non-Final Office Action from parallel U.S. Appl. No. 16/760,444 dated Nov. 16, 2020, 37 pages, for information purpose only.
Final Office Action from parallel U.S. Appl. No. 16/760,444 dated Apr. 16, 2021, 30 pages, for information purpose only.
Non-Final Office Action from parallel U.S. Appl. No. 16/760,444 dated Sep. 14, 2021, 22 pages, for information purpose only.
Final Office Action from parallel U.S. Appl. No. 16/760,444 dated Mar. 22, 2022, 12 pages, for information purpose only.
Kurata, N. et al. Surfactant-associated bacteria in the near-surface layer of the ocean., Sci. Rep. 6, 19123; doi: 10.1038/srep19123 (2016).
RapidTables, Percent (%) to ppm conversion calculator, accessed on Sep. 24, 2020.
International search report from parallel PCT Patent Application PCT/EP2018/079836 dated Mar. 29, 2019,15 pages (for reference purposes only).
Yihao Liu et al., Biochemical Characterization and Structural Analysis of a β-N-Acetylglucosaminidase from Paenibacillus barengoltzii for Efficient Production of N-Acetyl-D-glucosamine, J. Agric. Food Chem. 2020, 68, 5648-5657.
Probiotic, New Probiotic liquid laundry detergents with unique ActiveProbiotics technology, published on line May 9, 2017.
Uniprot Protein Database, protein Accesion Q840G9, accessed on Mar. 16, 2022.
Non-Final Office Action from parallel U.S. Appl. No. 16/760,444 dated Sep. 1, 2022, 18 pages, for information purpose only.
Chinese Search Report for Chinese Application No. 202080087502.6, dated Aug. 19, 2023; 9 pages.
European Search Report for European Application 20184733.2, dated Nov. 27, 2020; 7 pages.
German Search Report for German Application No. 102019135349.1, dated Oct. 8, 2020; 7 pages.
German Search Report for German Application No. 102019135352.1, dated Oct. 8, 2020; 7 pages.
German Search Report for German Application No. 102019135357.2, dated Oct. 14, 2020; 7 pages.
German Search Report for German Application No. 102019135361.0, dated Oct. 14, 2020; 6 pages.
International Search Report for International Application PCT/EP2020/084940; International Filing Date: May 4, 2021; 9 pages.
International Search Report for International Application PCT/EP2020/084947; International Filing Date: May 11, 2021; 9 pages.
International Search Report for International Application PCT/EP2020/084950; International Filing Date: Aug. 30, 2021; 10 pages.
International Search Report for International Application PCT/EP2020/084952; International Filing Date: May 4, 2021; 9 pages.
International Search Report for International Application PCT/EP2021/068393; International Filing Date: Oct. 25, 2021; 14 pages.
Needleman, et al.; "A General Method Applicable to the Search for Similarities in the Amino Acid Sequence of Two Proteins"; Journal of Molecular Biology, vol. 48; pp. 443-453 (1970).
Rice, et al.; "EMBOSS: The European Molecular Biology Open Software Suite"; Trends Genetic, vol. 16, Issue No. 6; pp. 276-277 (2000).
Siezen, et al.; "Homology modeling and protein engineering strategy of subtilases, the family of subtilisin-like serine proteinases"; Protein Engineering, vol. 4, Issue No. 7; pp. 719-737 (1993).
Siezen, et al.; "Subtilases: The superfamily of subtilisin-like serine proteinases"; Protein Science, vol. 6; pp. 501-523 (1997).
UniProtKB—A0A075LPR4 (uniprot.org/uniprotkb/A0A075LPR4/entry) (Last sequence update: Oct. 29, 2014) 4 pages.
EP Communication pursuant to Rule 164(2)(b) and Article 94(3) EPC for Application No. 20824151.3 dated Sep. 25, 2024.

* cited by examiner

The mature amino acid sequences with SEQ ID NO 7, SEQ ID NO 8 and SEQ ID NO 9, were aligned using the MUSCLE version 3.8.31 algorithm (Edgar, R. C. (2004). Nucleic Acids Research, 32(5), 1792-1797). From the resulting multiple alignment, a phylogenetic tree (Figure 1) was constructed using FastTree version 2.1.8 (Price et al. (2010). PloS one, 5(3)) and visualized using iTOL (Letunic, I., & Bork, P. (2007). Bioinformatics, 23(1), 127-128).

```
                                                           10         20         30         40
SEQ ID NO 7  Terribacillus saccharophilus  QDQEKGITIDISRKYYSIKTLKAIVDEISANGGDYLQLHFSDNES
SEQ ID NO 8  Terribacillus goriensis       QDQEKGITIDISRKYYSIETLKSILDEISANGGDYLQLHFSDNER
SEQ ID NO 9  Terribacillus saccharophilus  KDQEKGITIDISRKYYSIGTLKAIVDEINANGGDYLQLHFSDNES
SEQ ID NO 10 Terribacillus saccharophilus  QDQEKGITIDISRKHYTVETLKSLVDEISYNGGNYVQLHFSDNEN
SEQ ID NO 11 Terribacillus saccharophilus  KDQEKGISIDISRKYYSIGTLKAIIDEISANGGDYLQLHFSDNES 50         60         70         80         90
SEQ ID NO 7  Terribacillus saccharophilus  YAIASEFLGQNSENPNSAYLTKKELLSLIAYSNDRNIMVIPDIDL
SEQ ID NO 8  Terribacillus goriensis       YAIASEFLGQNGENPNSTYLTKKELLSLIAYSNDRDIMVIPDIDL
SEQ ID NO 9  Terribacillus saccharophilus  YAIASEFLGQNSENPNSTYLTKKELLSLIAYSNDRNIMVIPDIDL
SEQ ID NO 10 Terribacillus saccharophilus  YAIASEVLGCSSENTNNTYLTKMELLSLIAYSNDKDILVIPDIDL
SEQ ID NO 11 Terribacillus saccharophilus  YAIASDYLGCISDTPNNTYLTKNDLLSLIAYSNDRNILIIPDMDL 100        110        120        130
SEQ ID NO 7  Terribacillus saccharophilus  PAHSKGWLNIMKEKDSGLYTDIVTDYSEDTLDYHNNAVALYTANQ
SEQ ID NO 8  Terribacillus goriensis       PAHSRGWLNIMKEKDSGLYTDIVTDYSEDTLDYHNNAAALYTANQ
SEQ ID NO 9  Terribacillus saccharophilus  PAHSKGWLNVMKEKDSGLYTDIVTDYSEDTLDYHNNAAALYTANQ
SEQ ID NO 10 Terribacillus saccharophilus  PAHSKGWLELIKKKDVKLYMDIVTDYSEETLDYYDNRVALDTVNQ
SEQ ID NO 11 Terribacillus saccharophilus  PAHSRGWLELMKVKDRELYTDIVTDYSNETLDYHNNTDALNTANQ 140        150        160        170        180
SEQ ID NO 7  Terribacillus saccharophilus  LLDEVLDLFYQPKFAGKQRIVLGGDEVFGSGAHQTDFIRFMNQIA
SEQ ID NO 8  Terribacillus goriensis       LLDEVLDLFYQPKFAGKQRIVLGGDEVFGSGVHQTDFIRFMNQIA
SEQ ID NO 9  Terribacillus saccharophilus  LLDEVLDLFYQPKFAGKQRIVLGGDEVFGSGAHQTDFIRFMNQID
SEQ ID NO 10 Terribacillus saccharophilus  LLDEVLDLFYQPKFEGKQRIVLGGDEVSGSEVHQLDFIDFMNQIA
SEQ ID NO 11 Terribacillus saccharophilus  LLNDILPLFYQPKFAGKQRIVLGGDEVFGSEIHQLDFIRFINQIA 190        200        210        220
SEQ ID NO 7  Terribacillus saccharophilus  KTAKASNYEPQMVNDSIIPEGIQNLDRSFSILYWKQSTISNGAQS
SEQ ID NO 8  Terribacillus goriensis       ETAKASNYKPQMVNDSITPEGIQNLDRSFSILYWKQSTISNGAQG
SEQ ID NO 9  Terribacillus saccharophilus  ETAKASNYEPQMVNDSITPEGIQNLDRSFSILYWKQSTISSGAQG
SEQ ID NO 10 Terribacillus saccharophilus  STVKESKYEPQMVNDSIISEGIANLDSSFSILYWQQSTISSGEFS
SEQ ID NO 11 Terribacillus saccharophilus  STAKASNYAPQMVNDSIIAEGIQNLDKSFSILYWKQSTISNGAQS 230        240        250        260        270
SEQ ID NO 7  Terribacillus saccharophilus  LDVQDFEEKGLSVYNYNAYSLYFLPSTRFTQEDITEQIDYMKWAY
SEQ ID NO 8  Terribacillus goriensis       LDVQDFEEKGLSVYNYNAYSLYFLPATRFTQEDITEQIDYMKWAY
SEQ ID NO 9  Terribacillus saccharophilus  LDVQNFEEKGFSVYNYNAYSLYFLPSTRFTQEDITEQIDYMKWAY
SEQ ID NO 10 Terribacillus saccharophilus  LNVEDFENWGFSVTNYNAYSLYFLPSNGFTQEDINECMDYMNWAY
SEQ ID NO 11 Terribacillus saccharophilus  LEVQDFEDWDKPVYNYNAYSLYFLPSIRFTDEDITECMNYMKWAY 280        290        300        310
SEQ ID NO 7  Terribacillus saccharophilus  AYNKFFYISDYYKQVDTPNVKGSSLVFWGEHANDLSQEGLLKQEK
SEQ ID NO 8  Terribacillus goriensis       AYNKFFYISDYYKQVDTSNVKGSSLVFWGEHANDLSQEGLLKQEK
SEQ ID NO 9  Terribacillus saccharophilus  AYNKFFYISDYYKQVDTSNVKGSSLVFWGEHANDLSQEGLLEQEK
SEQ ID NO 10 Terribacillus saccharophilus  AENKFFYISDYYHAVETSNVKGSSLTFWGEHATDLSCKKLLKQEL
SEQ ID NO 11 Terribacillus saccharophilus  AYNKFFYISDYYKSVDASNVKGSSLTFWGEHATDLSQESLLEQEL 320
SEQ ID NO 7  Terribacillus saccharophilus  PLIQNFLGL
SEQ ID NO 8  Terribacillus goriensis       PLIQNFLGL
SEQ ID NO 9  Terribacillus saccharophilus  PLIQNFLSL
SEQ ID NO 10 Terribacillus saccharophilus  PLIRHYLNL
SEQ ID NO 11 Terribacillus saccharophilus  PLIKKFLSL
```

Figure 2

CLEANING COMPOSITIONS CONTAINING DISPERSINS III

CROSS-REFERENCE TO RELATED APPLICATIONS

The present application is a national stage entry according to 35 U.S.C. § 371 of PCT application No.: PCT/EP2018/079845 filed on Oct. 31, 2018; which claims priority to German Patent Application Serial No.: 10 2017 125 560.5, which was filed on Nov. 1, 2017; which are incorporated herein by reference in their entirety and for all purposes.

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are NOVOZYMES AS and HENKEL AG and Co KGaA.

REFERENCE TO A SEQUENCE LISTING SUBMITTED VIA EFS-WEB

The content of the ASCII text file of the sequence listing named "P77363US_seq_ST25", which is 58 kb in size was created on Oct. 29, 2018 and electronically submitted via EFS-Web herewith the application is incorporated by reference in its entirety.

TECHNICAL FIELD

The present disclosure relates to specific cleaning compositions comprising polypeptides having hexosaminidase activity. The disclosure further relates to the use of said compositions as well as methods of using said compositions.

BACKGROUND

Polypeptides having hexosaminidase activity include Dispersins such as Dispersin B (DspB), which are described as β-N-acetylglucosamininidases belonging to the Glycoside Hydrolase 20 family WO04061117 A2 (Kane Biotech INC) describe use of compositions comprising DspB for reducing and preventing biofilm caused by poly-N-acetylglucosamine-producing bacteria and Kane et al. describes the use of compositions comprising dispersins for reducing biofilm on medical devises and for wound care. Biofilm may also be present on laundry items, such as fabrics, other hard surfaces, such as dish wash utensils, dish washers and washing machines where they may cause malodor, which is difficult to remove even after wash. The application WO9850512 (Procter and Gamble) disclose laundry or cleaning products comprising one or more hexosaminidase enzymes.

SUMMARY

The present embodiment provides cleaning compositions comprising polypeptides belonging to the *Terribacillus* clade of hexosaminidases from the Glycoside Hydrolase 20 family, as defined herein, uses and methods of use thereof, in particular as defined in the appended claims.

The *Terribacillus* clade is shown in FIGS. 1 and 3. The polypeptides described herein have hexosaminidase activity. The embodiment further provides cleaning compositions comprising polypeptides having hexosaminidase activity and the use thereof for cleaning processes. The polypeptides disclosed herein having hexosaminidase activity have beneficial properties such as removal and/or reduction of biofilm related components such as EPS and/or PNAG in cleaning processes, including laundry and dish wash. The polypeptides disclosed herein belong to the *Terribacillus* clade, which are homologous sequences of a particular clade of the Glycoside Hydrolase 20 family.

The cleaning composition of the invention that contains the polypeptides defined herein (a) is a solid, such as granular, laundry detergent composition and further comprises
  (a1) at least one zeolite builder, such as in an amount of 10 to 50 wt.-%, or 20-30 wt.-%;
  (a2) at least one phosphonate builder, such as in an amount of 0.1 to 5 wt.-%, or 0.4 to 1.5 wt.-%;
  (a3) at least one further enzyme, such as a cellulase, such as in an amount of active enzyme of 100 to 5000 ppb or from 1000 to 2000 ppb; and
  (a4) at least one polymer, such as a polyvinylpyrrolidon polymer, such as in an amount of 0.01 to 1 wt.-%, or from 0.1 to 0.3 wt.-%; or (b) is a solid laundry detergent composition and further comprises
  (b1) at least one silicate builder, such as in an amount of 2 to 20 wt.-%, or from 5-10 wt.-%;
  (b2) optionally carboxymethylcellulose, such as in an amount of 0.1 to 10 wt.-%, or from 0.1 to 4 wt.-%;
  (b3) at least one further enzyme, such as a cellulase, such as in an amount of active enzyme of 0.1 to 100 ppm, or from 0.1 to 10 ppm;
  (b4) optionally at least one soil release polymer, such as a polyvinylpyrrolidon polymer, in an amount of 0.1 to 3 wt.-%, or from 0.1 to 1.0 wt.-%; and
  (b5) at least one bleaching system, comprising a bleaching agent, a bleach activator and a bleach catalyst, such as in an amount of 0.1 to 50 wt.-%, or from 0.1 to 30 wt.-%; or (c) is liquid laundry detergent composition and further comprises
  (c1) at least one surfactant, such as nonionic surfactant, such as in an amount of 1 to 20 wt.-%, or from 3 to 15 wt.-%;
  (c2) optionally at least one phosphonate builder, such as in an amount of 0.1 to 3 wt.-%, or from 0.25 to 1.5 wt.-%
  (c3) optionally at least at least one further enzyme, such as a cellulase, such as in an amount of enzyme composition of 0.001 to 1 wt.-%, or from 0.001 to 0.6 wt.-%; and
  (c4) optionally at least one organic solvent, such as glycerol, such as in an amount of 0.1 to 10 wt.-%, or from 0.1 to 5 wt.-%; or (d) is a liquid laundry detergent in unit dose form, such as a pouch comprising a water-soluble film, and further comprises
  (d1) water in an amount of up to 20 wt.-%, such as 5 to 15 wt.-%;
  (d2) optionally at least one bittering agent, such as Benzyldiethyl(2,6-xylylcarbamoyl)-methylammoniumbenzoate, such as in an amount of 0.00001 to 0.04 wt.-%;
  (d3) optionally at least one optical brightener, such as in an amount of 0.01 to 2 wt.-%, or from 0.01 to 1 wt.-%; and (d4) optionally at least one polymer, such as in an amount of 0.01 to 7 wt.-%, or from 0.1 to 5 wt.-%; or
(e) is a fabric finisher and further comprises
  (e1) at least one softening silicone, such as an amino-functionalized silicone, such as in an amount of 0.1 to 10 wt.-%, or from 0.1 to 2 wt.-%;
  (e2) at least one perfume, such as at least partially encapsulated in microcapsules, or at least partially encapsulated in melamine-formaldehyde microcapsules, such as in an amount of 0.01 to 3 wt.-%, or 0.1 to 1 wt.-%;
  (e3) optionally polyquarternium 10 in an amount of 0.1 to 20 wt.-%, such as 0.1 to 13 wt.-%;
  (e4) optionally polyquarternium 37 in an amount of 0.1 to 20 wt.-%, such as 0.1 to 13 wt.-%;
  (e5) optionally a plant-based esterquat, such as a canola- or palm-based esterquat, in an amount of 0.1 to 20 wt.-%, such as 0.1 to 13 wt.-%; and
  (e6) optionally adipic acid, in an amount of 0.1 to 20 wt.-%, such as 0.1 to 13 wt.-%; or
(f) is an acidic cleaning agent, such as having a pH less than 6, and further comprises
  (f1) plant-based or bio-based surfactants, such as each in an amount of 0.1 to 5, or each in an amount of 0.1 to 2 wt.-%;
  (f2) at least one acidic biocide, such as selected from acids, or HCl and formic acid; and
  (f3) at least one soil release, water repellant or water spreading polymer, such as in an amount of 0.01 to 3 wt.-%, or from 0.01 to 0.5 wt.-%; or
(g) is a neutral cleaning agent, such as having a pH between 6.0 and 7.5, and further comprises
  (g1) plant-based or bio-based surfactants, such as each in an amount of 0.1 to 5, or each in an amount of 0.1 to 2 wt.-%;
  (g2) at least one biocide, such as selected from quaternary ammonium compounds and alcohols; and
  (g3) at least one soil release, water repellant or water spreading polymer, such as in an amount of 0.01 to 3 wt.-%, or from 0.01 to 0.5 wt.-%; or
(h) is an alkaline cleaning agent, such as having a pH of more than 7.5, and further comprises
  (h1) plant-based or bio-based surfactants, such as each in an amount of 0.1 to 5, or each in an amount of 0.1 to 2 wt.-%; or
(i) is a hand dishwashing agent, such as liquid hand dishwashing agent, and further comprises
  (i1) at least one anionic surfactant, such as in an amount of 0.1 to 40 wt.-%, or from 5 to 30 wt.-%;
  (i2) at least one amphoteric surfactant, such as betain, such as in an amount of 0.1 to 25 wt.-%, or from 1 to 15 wt.-%;
  (i3) at least one nonionic surfactant, such as in an amount of 0.1 to 25 wt.-%, or from 2 to 10 wt.-%;
  (i4) at least one further enzyme, such as selected from proteases, amylases and combinations thereof, such as in an amount of enzyme composition of up to 1 wt.-%, or up to 0.6 wt.-%; or
(j) is an automatic dishwashing composition and further comprises
  (j1) at least one builder selected from citrate, aminocarboxylates and combinations thereof, such as in an amount of 5 to 30 wt.-%, or from 10 to 20 wt.-%;
  (j2) at least one phosphonate builder, such as in an amount of 0.1 to 5 wt.-%, or from 0.4 to 1.5 wt.-%;
  (j3) at least one nonionic surfactant, such as in an amount of 0.1 to 10 wt.-%, or 1 to 5 wt.-%;
  (j4) at least one bleaching system, comprising a bleaching agent, a bleach activator and a bleach catalyst, such as in an amount of 0.1 to 50 wt.-%, or from 0.1 to 30 wt.-%; and
  (j5) at least one polymer selected from sulfopolymers, cationic polymers and polyacrylates, such as in an amount of 0.01 to 15 wt. %, or from 2 to 10 wt. %; or
(k) further comprises
  (k1) at least one sulfopolymer, such as in an amount of 1 to 15, or from 2 to 10 wt.-% and is a dishwashing, or an automatic dishwashing composition; or
(l) further comprises at least one adjunct ingredient selected from probiotics, such as microbes, spores or combinations thereof; or
(m) is in unit dose form and comprises at least 2, such as 2, 3, 4 or 5 separate compartments; or
(n) is a phosphate-free composition.

When in the following reference is made to "compositions of the invention" or "compositions as described herein", the above-specified compositions (a)-(n) are meant. Furthermore, if not indicated otherwise, all references to percentages in relation to the disclosed compositions relate to wt % relative to the total weight of the respective composition. It is understood that when reference is made to compositions that contain a polypeptide as defined herein, the respective composition contains at least one of said polypeptides but can also comprise two or more of them.

In one aspect, the polypeptide having hexosaminidase activity is selected from the group consisting of:
  (a) a polypeptide having at least 80% sequence identity to the mature polypeptide of SEQ ID NO 2, 4, 6, 13 or 15;
  (b) a variant of the mature polypeptide of SEQ ID NO 2, 4, 6, 13 or 15 comprising a substitution, deletion, and/or insertion at one or more (e.g., several) positions; and
  (c) a fragment of the polypeptide of (a) or (b) that has hexosaminidase activity.

The above compositions may include polypeptides comprising a catalytic domain belonging to the Glycoside Hydrolase family 20 (GH20) and having at least 60% sequence identity to amino acids 1 to 324 of SEQ ID NO:2; at least 60% sequence identity to amino acids 1 to 324 of SEQ ID NO:4, at least 60% sequence identity to amino acids 1 to 324 of SEQ ID NO: 6, at least 60% sequence identity to amino acids 1 to 324 of SEQ ID NO:13 or at least 60% sequence identity to amino acids 1 to 324 of SEQ ID NO:15. The cleaning methods used in cleaning processes. The invention further relates to a method for cleaning or laundering an item comprising the steps of:
  a. exposing an item to a wash liquor comprising a detergent composition comprising the polypeptides as defined herein;
  b. optionally completing at least one wash cycle; and
  c. optionally rinsing the item,
wherein the item is a textile or a hard surface.

In addition is claimed the use of a composition, as defined above, comprising a polypeptide having hexosaminidase activity selected from the group consisting of the polypeptides of SEQ ID NO 7, 8, 9, 10, 11 or a polypeptide having at least 60% sequence identity for deep cleaning of an item.

A cleaning composition, as defined above, may include at least 0.001 ppm polypeptide having hexosaminidase activity, wherein the polypeptide is selected from the group consisting of polypeptides having at least 60% sequence identity to the mature polypeptide shown in SEQ ID NO 7, 8, 9, 10 and 11. A composition may be used for deep-cleaning of an item, wherein the item is a textile.

A method for cleaning/laundering an item may include: a) expose an item to a wash liquor comprising a detergent composition or to the detergent solution as such; b) optionally completing at least one wash cycle; and optionally rinsing the item, wherein the item is a textile or a hard surface.

The composition may be used:
(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item,
wherein the item is a textile.

BRIEF DESCRIPTION OF THE FIGURES

In the following, the various embodiments described herein are explained in more detail in conjunction with the associated figures.

FIG. 2 An alignment of the polypeptides
FIG. 3 A phylogenetic tree of the polypeptides

OVERVIEW OF SEQUENCES OF THE *TERRIBACILLUS* CLADE

Figure 1:
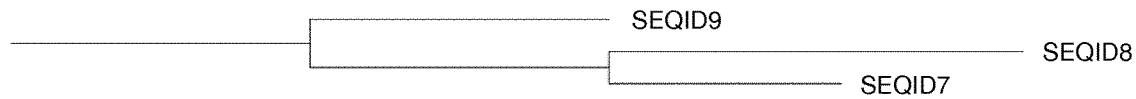
FIG. 1 Phylogenic tree showing the *Terribacillus* clade.

SEQ ID NO 1 is the DNA encoding the full-length polypeptide from *Terribacillus saccharophilus*
SEQ ID NO 2 is the polypeptide derived from SEQ ID NO 1
SEQ ID NO 3 is the DNA encoding the full-length polypeptide from *Terribacillus goriensis*
SEQ ID NO 4 is the polypeptide derived from SEQ ID NO 3
SEQ ID NO 5 is the DNA encoding the full-length polypeptide from *Terribacillus saccharophilus*
SEQ ID NO 6 is the polypeptide derived from SEQ ID NO 5
SEQ ID NO 7 is the mature polypeptide of SEQ ID NO 2
SEQ ID NO 8 is the mature polypeptide of SEQ ID NO 4
SEQ ID NO 9 is the mature polypeptide of SEQ ID NO 6
SEQ ID NO 10 is the mature polypeptide of SEQ ID NO 13
SEQ ID NO 11 is the mature polypeptide of SEQ ID NO 15
SEQ ID NO 12 is the DNA encoding the full-length polypeptide from *Terribacillus saccharophilus*
SEQ ID NO 13 is the polypeptide derived from SEQ ID NO 12
SEQ ID NO 14 is the DNA encoding the full-length polypeptide from *Terribacillus saccharophilus*
SEQ ID NO 15 is the polypeptide derived from SEQ ID NO 14
SEQ ID NO 16 is the *Bacillus clausii* secretion signal
SEQ ID NO 17 is a His-tag sequence
SEQ ID NO 18 is the polypeptide motif GXDE SEQ ID NO 19 is the polypeptide motif [EQ][NRSHA][YVFL][AGSTC][IVLF][EAQYN][SN]
SEQ ID NO 20 is the polypeptide motif [VIM][LIV]G[GAV]DE[VI][PSA]
SEQ ID NO 21 is the polypeptide motif WND[SQR][IVL][TLVM]
SEQ ID NO 22 is the polypeptide motif QSTL
SEQ ID NO 23 is the polypeptide motif NKFFY
SEQ ID NO 24 is the polypeptide motif NLD[DR]S Definitions Dispersin: The term "dispersin" and the abbreviation "Dsp" means a polypeptide having hexosaminidase activity, EC 3.2.1.—that catalyzes the hydrolysis of β-1,6-glycosidic linkages of N-acetyl-glucosamine polymers (poly-N-acetyl-glucosamine) found e.g. in biofilm.

Hexosaminidase: The term "hexosaminidases" means a polypeptide having hexosaminidase activity (hexosaminidases), and includes EC 3.2.1.e.g. that catalyzes the hydrolysis of of N-acetyl-D-hexosamine or N-acetyl-glucosamine polymers found e.g. in biofilm. The term includes dispersins and includes polypeptides having N-acetylglucosaminidase activity and β-N-acetylglucosamininidase activity. The term "polypeptide having hexosaminidase activity" may be used interchangeably with the term hexosaminidases and similar the term "polypeptide having β-N-acetylglucosaminidase activity" may be used interchangeably with the term β-N-acetylglucosamininidases For the purposes, hexosaminidase activity is determined according to the procedure described in Assay 1 or 2. In one aspect, the polypeptides have at least 20%, e.g., at least 40%, at least 50%, at least 60%, at least 70%, at least 80%, at least 90%, at least 95%, or at least 100% of the hexosaminidase activity of the mature polypeptide of SEQ ID NO 2. In one aspect, the polypeptides have at least 20%, e.g., at least 40%, at least 50%, at least 60%, at least 70%, at least 80%, at least 90%, at least 95%, or at least 100% of the hexosaminidase activity of the mature polypeptide of SEQ ID NO 4. In one aspect, the polypeptides have at least 20%, e.g., at least 40%, at least 50%, at least 60%, at least 70%, at least 80%, at least 90%, at least 95%, or at least 100% of the hexosaminidase activity of the mature polypeptide of SEQ ID NO 6. In one aspect, the polypeptides have at least 20%, e.g., at least 40%, at least 50%, at least 60%, at least 70%, at least 80%, at least 90%, at least 95%, or at least 100% of the hexosaminidase activity of the mature polypeptide of SEQ ID NO 13. In one aspect, the polypeptides have at least 20%, e.g., at least 40%, at least 50%, at least 60%, at least 70%, at least 80%, at least 90%, at least 95%, or at least 100% of the hexosaminidase activity of the mature polypeptide of SEQ ID NO 15.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm may be produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry and hard surfaces biofilm producing bacteria can be found among the following species: *Acinetobacter* sp., *Aeromicrobium* sp., *Brevundimonas* sp., *Microbacterium* sp *Micrococcus luteus*, *Pseudomonas* sp., *Streptococcus* sp., *Streptococcus dysgalactiae*, *Staphylococcus epidermidis*, *Staphylococcus aureus*, *Staphylococcus pneumoniae*, *Stenotrophomonas* sp., *Enterobacter* sp., *Xanthomonas* sp., *Yersinia* sp., *Klebsiella* sp., *Burkholderia* sp., *Stenotrophomonas* sp., *Variovorax* sp., *Escherichia* sp., *Ralstonia* sp., *Achromobacter* sp., *Luteibacter* sp., *Citrobacter* sp., *Xanthomonadaceae* sp., *Halomonas* sp., *Bordetella* sp., *Lysobacter* sp., *Serratia* sp., *Escherichia* sp., *Aggregatibacter* sp., *Listeria monocytogenes*, *Clostridium difficile*, *Mycobacterium* sp., *Neisseria gonorrheae*, *H. influenzae*, *Haemophilus ducreyi*, *Helicobacter pylori*, *Campylobacter jejuni* and *Enterococcus faecalis* as well as the fungi *Candida albicans*, *Aspergillus flavus*, *Fusarium solani*, and *Cryptococcus neoformans*. In one aspect, the biofilm component e.g. poly-N-acetylglucosamine comprising strain is *Brevundimonas* sp. In one aspect, the biofilm component e.g. poly-N-acetylglucosamine comprising strain is *Pseudomonas alcaliphila* or *Pseudomonas fluorescens*. In one aspect, the biofilm component e.g. poly-N-acetylglucosamine comprising strain is *Staphylococcus aureus*.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Clade: a group of polypeptides clustered together based on homologous features traced to a common ancestor. Polypeptide clades can be visualized as phylogenetic trees and a clade is a group of polypeptides that consists of a common ancestor and all its lineal descendants (FIG. 1). The polypeptides e.g. all belong to the *Terribacillus* clade, which is illustrated as a phylogenetic tree in FIGS. 1 and 3. The *Terribacillus* clade or clade of *Terribacillus* is a group of enzymes all related to the same ancestor and share common properties. Polypeptides forming a group within the clade (a subclade) of the phylogenetic tree can also share common properties and are more closely related than other polypeptides in the clade.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant reduction or removal of components of biofilm, such as EPS or parts hereof, polysaccharides, PNAG (poly-N-acetylglucosamine), proteins, DNA, soil or other components present in the biofilm.

Detergent adjunct ingredient: The detergent adjunct ingredient is different to the hexosaminidase. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, antifoaming agents, dispersants, processing aids, bittering agents and/or pigments.

Cleaning and/or Detergent Composition: The terms "cleaning composition" and "detergent composition" are used interchangeably herein and refer to compositions that find use in the removal of undesired compounds from items to be cleaned, such as textiles and hard surfaces. The detergent composition may be used to e.g. clean textiles for both household cleaning and industrial cleaning. The terms encompass any materials/compounds selected for the cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners (fabric finishers); and textile and laundry pre-spotters/pretreatment). In addition, the term also includes hand and automatic dishwashing detergents and cleaning detergents for hard surfaces. In addition to containing the polypeptide described herein, the composition may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has hexosaminidase activity. In one aspect, a fragment contains at least 300 amino acid residues (e.g., amino acids 1 to 300 of SEQ ID NO 2), at least 305 amino acid residues (e.g., amino acids 1 to 305 of SEQ ID NO 2), at least 310 amino acid residues (e.g., amino acids 1 to 310 of SEQ ID NO 2), at least 315 amino acid residues (e.g., amino acids 1 to 315 of SEQ ID NO 2), or at least 320 amino acid residues (e.g., amino acids 1 to 320 of SEQ ID NO 2). In one aspect, a fragment contains at least 300 amino acid residues (e.g., amino acids 1 to 300 of SEQ ID NO 4), at least 305 amino acid residues (e.g., amino acids 1 to 305 of SEQ ID NO 4), at least 310 amino acid residues (e.g., amino acids 1 to 310 of SEQ ID NO 4), at least 315 amino acid residues (e.g., amino acids 1 to 315 of SEQ ID NO 4), or at least 320 amino acid residues (e.g., amino acids 1 to 320 of SEQ ID NO 4). In one aspect, a fragment contains at least 300 amino acid residues (e.g., amino acids 1 to 300 of SEQ ID NO 6), at least 305 amino acid residues (e.g., amino acids 1 to 305 of SEQ ID NO 6), at least 310 amino acid residues (e.g., amino acids 1 to 310 of SEQ ID NO 6), at least 315 amino acid residues (e.g., amino acids 1 to 315 of SEQ ID NO 6), or at least 320 amino acid residues (e.g., amino acids 1 to 320 of SEQ ID NO 6). In one aspect, a fragment contains at least 300 amino acid residues (e.g., amino acids 1 to 300 of SEQ ID NO 13), at least 305 amino acid residues (e.g., amino acids 1 to 305 of SEQ ID NO 13), at least 310 amino acid residues (e.g., amino acids 1 to 310 of SEQ ID NO 13), at least 315 amino acid residues (e.g., amino acids 1 to 315 of SEQ ID NO 13), or at least 320 amino acid residues (e.g., amino acids 1 to 320 of SEQ ID NO 13). In one aspect, a fragment contains at least 300 amino acid residues (e.g., amino acids 1 to 300 of SEQ ID NO 15), at least 305 amino acid residues (e.g., amino acids 1 to 305 of SEQ ID NO 15), at least 310 amino acid residues (e.g., amino acids 1 to 310 of SEQ ID NO 15), at least 315 amino acid residues (e.g., amino acids 1 to 315 of SEQ ID NO 15), or at least 320 amino acid residues (e.g., amino acids 1 to 320 of SEQ ID NO 15).

Host cell: The term "host cell" means any cell type that is susceptible to transformation, transfection, transduction, or the like with a nucleic acid construct or expression vector comprising a polynucleotide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide. The fermentation broth from that host cell will comprise the isolated polypeptide.

Improved wash performance: The term "improved wash performance" is defined herein as an enzyme displaying an increased wash performance in a detergent composition relative to the wash performance of same detergent composition without the enzyme e.g. by increased stain removal or less re-deposition. The term "improved wash performance" includes wash performance in laundry.

Laundering: The term "laundering" relates to both household laundering and industrial laundering and means the process of treating textiles with a solution containing a cleaning or detergent composition. The laundering process can for example be carried out using e.g. a household or an industrial washing machine or can be carried out by hand Malodor: By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal Another example of malodor can be the odor from spices, which sticks to items for example curry or other exotic spices which smells strongly.

Mature polypeptide: The term "mature polypeptide" means a polypeptide in its final form following translation and any post-translational modifications, such as N-terminal processing, C-terminal truncation, glycosylation, phosphorylation, etc. In some aspects, the mature polypeptide is amino acids 1 to 324 of SEQ ID NO 2 and amino acids −41 to −1 of SEQ ID NO 2 are a signal peptide. In some aspects, the mature polypeptide is the amino acid sequence having SEQ ID NO 7. In some aspects, the mature polypeptide is amino acids 1 to 324 of SEQ ID NO 4 and amino acids −25 to −1 of SEQ ID NO 4 are a signal peptide. In some aspects, the mature polypeptide is the amino acid sequence having SEQ ID NO 8. In some aspects, the mature polypeptide is amino acids 1 to 324 of SEQ ID NO 6 and amino acids −25 to −1 of SEQ ID NO 6 are a signal peptide. In some aspects, the mature polypeptide is the amino acid sequence having SEQ ID NO 9. In some aspects, the mature polypeptide is amino acids 1 to 324 of SEQ ID NO 13 and amino acids −24 to −1 of SEQ ID NO 13 are a signal peptide. In some aspects, the mature polypeptide is the amino acid sequence having SEQ ID NO 10. In some aspects, the mature polypeptide is amino acids 1 to 324 of SEQ ID NO 15 and amino acids −24 to −1 of SEQ ID NO 15 are a signal peptide. In some aspects, the mature polypeptide is the amino acid sequence having SEQ ID NO 11.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having hexosaminidase activity. In one aspect, the mature polypeptide coding sequence is nucleotides 124 to 1095 of SEQ ID NO 1 and nucleotides 1 to 123 of SEQ ID NO 1 encodes a signal peptide. In one aspect, the mature polypeptide coding sequence is nucleotides 76 to 1047 of
SEQ ID NO 3 and nucleotides 1 to 75 of SEQ ID NO 3 encode a signal peptide. In one aspect, the mature polypeptide coding sequence is nucleotides 76 to 1047 of SEQ ID NO 5 and nucleotides 1 to 75 of SEQ ID NO 5 encode a signal peptide. In one aspect, the mature polypeptide coding sequence is nucleotides 73 to 1044 of SEQ ID NO 12 and nucleotides 1 to 72 of SEQ ID NO 12 encode a signal peptide. In one aspect, the mature polypeptide coding sequence is nucleotides 73 to 1044 of SEQ ID NO 14 and nucleotides 1 to 72 of SEQ ID NO 14 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), such as version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−
Total Number of Gaps in Alignment)

Stringency conditions: The term "very low stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, pre-hybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

Variant: The term "variant" means a polypeptide having hexosaminidase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Nomenclature

For purposes, the nomenclature [IV] or [I/V] means that the amino acid at this position may be isoleucine (Ile, I) or valine (Val, V). Likewise, the nomenclature [LVI] and [L/V/I] means that the amino acid at this position may be a leucine (Leu, L), valine (Val, V) or isoleucine (Ile, I), and so forth for other combinations as described herein. Unless otherwise limited further, the amino acid X is defined such that it may be any of the 20 natural amino acids.

DETAILED DESCRIPTION

Various enzymes have been used in laundry many of which relate to removal of malodor. WO2014/087011 describes the use of a deoxyribonuclease (DNase) for reducing malodor from laundry and/or textile, WO9909143 describes the use of one or more oxidoreductases in combination with a mediator for the reduction of malodor and WO2012/112718 describe a method for inhibiting production of laundry malodor caused by bacteria by using various strains of Bacillus. The present disclosure relates to cleaning e.g. detergent compositions comprising polypeptides from the Terribacillus clade of GH20 family of polypeptides having hexosaminidase activity. Also claimed are laundering methods and the use of the compositions comprising polypeptides with hexosaminidase activity. The polypeptides from the Terribacillus clade of GH20 family with hexosaminidase activity are useful in reducing and preventing staining of items being washed. The inventors have surprisingly found that the polypeptides of the Terribacillus clade of GH20 family having hexosaminidase activity are useful for reduction of laundry associated organic matter e.g. EPS and or PNAG. WO200406117 describes compositions comprising dispersins e.g. DspB. The composition may include a detergent which may be anionic, cationic, or non-ionic. WO9850512 describes enzymes having hexosaminidase activity. The polypeptides have hexosaminidase activity however, these do not belong to the DspB clade or to is related to any of the enzymes described in WO9850512. The polypeptides belong to the Terribacillus clade and are thus distinct from the DspB and from those disclosed in WO9850512. It was therefore surprising that the polypeptide could be used for prevention, reduction and/or removal of organic matter such as biofilm components e.g. polysaccharides e.g. PNAG (poly-N-acetylglucosamine) on hard surfaces as well as in laundry. There is no indication in the art of the use of hexosaminidases in cleaning processes such as laundry or in detergent compositions comprising e.g. builders and/or bleaches. To be useful in cleaning processes the enzymes need to perform its action in detergents under the conditions of cleaning processes such as laundry, which includes stability in the presence of detergent components such as surfactants, builders and bleach components. The components of a detergent may significantly effect on the performance of the enzymes such as the hexosaminidases. The present application surprisingly shows that polypeptides belonging to the Terribacillus clade are particularly stable in the present of surfactant linear alkylbenzenesulfonates (LAS) which is a very common surfactant in detergents. The polypeptides belonging to the Terribacillus are thus particularly useful for deep cleaning e.g. of textiles in washing machines.

An overview of the Terribacillus clade is provided in FIG. 1. The Terribacillus clade comprises homologous sequences. The polypeptides with hexosaminidase activity having the mature amino acid sequences SEQ ID 7, 8 and 9 can be pairwise aligned using the Needleman-Wunsch algorithm (Needleman and Wunsch, 1970, J. Mol. Biol. 48: 443-453). The percent identities resulting from such alignments are shown in Table 1 below.

TABLE 1

| SEQ ID NO 11 | SEQ ID NO 10 | SEQ ID NO 7 | SEQ ID NO 9 | SEQ ID NO 8 | |
|---|---|---|---|---|---|
| 100 | 75.9 | 81.8 | 82.4 | 81.2 | SEQ ID NO 11 |
| 75.9 | 100 | 77.5 | 76.5 | 77.5 | SEQ ID NO 10 |
| 81.8 | 77.5 | 100 | 95.1 | 95.7 | SEQ ID NO 7 |
| 82.4 | 76.5 | 95.1 | 100 | 93.5 | SEQ ID NO 9 |
| 81.2 | 77.5 | 95.7 | 93.5 | 100 | SEQ ID NO 8 |

Table 1 shows that the polypeptides share close sequence relatedness. The polypeptides comprising the amino acids sequences of SEQ ID NO 7, SEQ ID NO 8, SEQ ID NO 9, SEQ ID NO 10 and SEQ ID NO 11 belongs to a subclade of the Dispersin clade. These polypeptides share more than 90% pairwise sequence identity and are closer related to each other compared to e.g. the DspB polypeptides which lies further away (not shown).

One aspect relates to a composition, as defined herein, comprising a polypeptide comprising the amino acid sequence shown in SEQ ID NO 7 or is a polypeptide having at least 99.8% or 100% sequence identity hereto, wherein the polypeptide has hexosaminidase activity.

One aspect relates to a composition, as defined herein, comprising a polypeptide comprising the amino acid sequence shown in SEQ ID NO 8 or is a polypeptide having at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising the amino acid sequence shown in SEQ ID NO 9 or is a polypeptide having at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising the amino acid sequence shown in SEQ ID NO 10 or is a polypeptide having at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

The polypeptides described herein all lie within the same clade, the *Terribacillus* clade, and all have common functional features including deep cleaning properties in the presence of detergents. The inventors have surprisingly found that the polypeptides of the *Terribacillus* clade comprising the mature polypeptides with SEQ ID NO 7, 8, 9, 10, 11 or polypeptides having at least 80% sequence identity hereto, share specific properties, more precisely the polypeptides comprised by this clade all have good deep cleaning effects with a broad range of surfactants such as LAS and are therefore particularly useful in detergents with surfactants, such as in detergent comprising anionic, non-ionic, cationic and/or amphoteric surfactants.

As already described the polypeptides having hexosaminidase activity may comprise the structural domains of Glyco_hydro_20 e.g. GH20. Polypeptides comprising a GH20 domain may comprise several motifs one example is GXDE (SEQ ID NO 18) situated in positions corresponding to positions 158 to 161 in *Terribacillus saccharophilus* (SEQ ID NO 9). Residues D and E are the key catalytic residues of GH20 (pos 160 and 161 in SEQ ID NO 9). The GH20 polypeptides can be separated into multiple distinct sub-clusters, or clades, examples of specific domains are listed below. A further domain, shared by the polypeptides, was identified. This domain has not been described previously, the domain is termed IAS and polypeptides of this domain are in addition to having hexosaminidase activity e.g. PNAG activity, characterized by comprising certain motifs e.g. one or more of the [EQ][NRSHA][YVFL][AGSTC][IVLF][EAQYN][SN] (SEQ ID NO 19), corresponding to ESYAIAS at position 44 to 50 of SEQ ID NO 9. Another domain, shared by the polypeptides, was identified. This domain has not been described previously. The domain is termed WND and polypeptides of this domain comprise GH20 domain, are of bacterial origin and are in addition to having PNAG activity, characterized by comprising certain motifs. The polypeptides of the domain may comprise the motif [VIM][LIV]G[GAV]DE[VI][PSA] (SEQ ID NO: 20), corresponding to pos 156 to 163 of SEQ ID NO 9, where G (corresponding to position 158 of SEQ ID NO 9) is fully conserved in *Terribacillus* clade and residues D and E are the key catalytic residues of GH20 (pos 160 and 161 in SEQ ID NO 9). Another motif which may be comprised by the polypeptides is WND[SQR][IVL][TLVM] (SEQ ID NO: 21), 193 to 198 in SEQ ID NO 9, where W (pos 193 in SEQ ID NO 9) is part of the active site pocket and putatively involved in binding of the N-acetyl group of the PNAG substrate. The polypeptides of the *Terribacillus* clade may be further subdivided in a clade termed QSTL, which comprises WND domain polypeptides of bacterial origin, having PNAG activity. The polypeptides of the clade comprise the motif example QSTL (SEQ ID NO: 22), corresponding to pos 216 to 219 of SEQ ID NO 9, where all four amino are fully conserved in QSTL clade and putatively involved in substrate binding. Another motif which may be comprised by the polypeptides of the QSTL clade is NKFFY (SEQ ID NO: 23), 273 to 277 in SEQ ID NO 9. A further motif which may be comprised by the polypeptides of the QSTL clade is NLD[DR]S (SEQ ID NO: 24), 204 to 208 in SEQ ID NO 9. In one aspect, the polypeptides comprise the GXDE (SEQ ID NO 18) motif. In one aspect, the polypeptides comprise the [EQ][NRSHA][YVFL][AGSTC][IVLF][EAQYN][SN] (SEQ ID NO 19) motif. In one aspect, the polypeptides comprise the motif [VIM][LIV]G[GAV]DE[VI][PSA] (SEQ ID NO: 20). In one aspect, the polypeptides comprise the motif WND[SQR][IVL][TLVM] (SEQ ID NO: 21). In one aspect, the polypeptides comprise the motif QSTL (SEQ ID NO 22). In one aspect, the polypeptides comprise the motif NKFFY (SEQ ID NO: 23). In one aspect, the polypeptides comprise the motif NLD[DR]S (SEQ ID NO: 24). An alignment of the polypeptides comprised in the QSTL clade is shown in FIG. 2.

Some aspect relates to a composition, as defined herein, comprising a polypeptide comprising one or both motif(s) GXDE (SEQ ID NO 18) or [EQ][NRSHA][YVFL][AGSTC][IVLF][EAQYN][SN] (SEQ ID NO 19), wherein the polypeptide comprises an amino acid sequence selected from the polypeptides shown in SEQ ID NOS 7, 8, 9, 10 and 11 or polypeptides having at least 80% sequence identity hereto.

Some aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises an amino acid sequence selected from the polypeptides shown in SEQ ID NOS 7, 8, 9, 10 and 11 or polypeptides having at least 80% sequence identity hereto.

Some aspect relates to a composition, as defined herein, comprising a polypeptide comprising one or more of the motif(s) QSTL (SEQ ID NO 22), NKFFY (SEQ ID NO: 23) or NLD [DR]S (SEQ ID NO: 24), wherein the polypeptide comprises an amino acid sequence selected from the polypeptides shown in SEQ ID NOS 7, 8, 9, 10 and 11 or polypeptides having at least 80% sequence identity hereto.

One aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 7 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 8 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 9 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 10 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or both motif(s) [VIM][LIV]G[GAV]DE[VI][PSA] (SEQ ID NO 20) or WND[SQR][IVL][TLVM] (SEQ ID NO 21), wherein the polypeptide comprises the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 7 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 8 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 9 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 10 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect relates to a composition, as defined herein, comprising a polypeptide comprising one or more of the motif(s) QSTL (SEQ ID NO 22), NKFFY (SEQ ID NO: 23) or NLD[DR]S (SEQ ID NO: 24), wherein the polypeptide comprises the amino acid sequence shown in SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity.

One aspect, relates to the use in a cleaning process of a composition, as defined herein, comprising a polypeptide comprising the amino acid sequence shown in SEQ ID NO 7, SEQ ID NO 8, SEQ ID NO 9, SEQ ID NO 10, SEQ ID NO 11 or is a polypeptide having at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto, wherein the polypeptide has hexosaminidase activity. Some aspects relate to cleaning e.g. detergent compositions as defined herein comprising a) one or more polypeptide selected from the group consisting of SEQ ID NO 7, SEQ ID NO 8, SEQ ID NO 9, SEQ ID NO 10 and SEQ ID NO 11, wherein the polypeptide has hexosaminidase activity.

On aspect relates to a cleaning composition as defined herein comprising at least 0.001 ppm polypeptide having hexosaminidase activity, wherein the polypeptide is selected from the group consisting of polypeptides having at least 60% sequence identity to the mature polypeptide shown in SEQ ID NO 7, 8, 9, 10 and 11.

The amount of polypeptide may be in the range of 0.00004-100 ppm, such as in the range of 0.00008-50 ppm, in the range of 0.00001-20, in the range of 0.0002-20 ppm, in the range of 0.0001-50 ppm, in the range of 0.0002-50, in the range of 0.0004-50, in the range of 0.0008-50, in the range of 0.001-50 ppm, 0.01-50 ppm, such as 0.0001-50 ppm, alternatively 0.0002-20 ppm, e.g. 0.0002-10 ppm, alternatively 0.001-10 ppm, or 0.002-10 ppm. The hexosaminidase may be in an amount corresponding to at least 0.00001 ppm, such as at least 0.00002 ppm, at least 0.0001 ppm, at least 0.0002 ppm, at least 0.0005 ppm, at least 0.001 ppm, at least 0.002 mg ppm, at least 0.005 ppm, at least 0.01 ppm or at least 0.02 ppm. The composition may comprise at least 0.00008%, such as at least 0.0000.1%, 0.00002%, 0.000.1%, 0.0002%, 0.001%, 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% hexosaminidase In a non-limiting embodiment, the polypeptide has N-acetylglucosaminidase activity and/or β-N-acetylglucosamininidase activity e.g. activity to PNAG. In one aspect, the polypeptide comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24). In one aspect, the polypeptide has N-acetylglucosaminidase activity and/or β-N-acetylglucosamininidase activity e.g. activity to PNAG and comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24). In one aspect, the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 7, SEQ ID NO 8, SEQ ID NO 9, SEQ ID NO 10 and SEQ ID NO 11.

In one aspect, the polypeptide has N-acetylglucosaminidase activity and/or β-N-acetylglucosamininidase activity e.g. activity to PNAG and comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO 7, SEQ ID NO 8, SEQ ID NO 9, SEQ ID NO 10 and SEQ ID NO 11.

In one aspect, the polypeptide comprising or consisting of SEQ ID NO 7 or the mature polypeptide of SEQ ID NO 2, comprising or consisting of SEQ ID NO 8 or the mature polypeptide of SEQ ID NO 4, comprising or consisting of SEQ ID NO 9 or the mature polypeptide of SEQ ID NO 6, comprising or consisting of SEQ ID NO 10 or the mature polypeptide of SEQ ID NO 13 or comprising or consisting of SEQ ID NO 11 or the mature polypeptide of SEQ ID NO 15.

The composition is a cleaning composition such as a laundry or dish wash composition. Some aspect relates to a cleaning composition, as defined herein, comprising a polypeptide and a further adjunct ingredient, wherein the adjunct ingredient is selected from one or more of,
 a) at least one builder,
 b) at least one surfactant, and
 c) at least one bleach component.

Some aspects relate to cleaning compositions e.g. detergent compositions, as defined herein, comprising a) one or more polypeptide selected from the group consisting of SEQ ID NO 7, SEQ ID NO 8, SEQ ID NO 9, SEQ ID NO 10 and SEQ ID NO 11 or a polypeptide having at least 80% sequence identity hereto, wherein the polypeptide has hexosaminidase activity.

Some aspect relates to a detergent composition, as defined herein, comprising at least 0.01 ppm of active enzyme polypeptide, wherein the enzyme polypeptide is selected from the group consisting of SEQ ID NO 7, SEQ ID NO 8 or SEQ ID NO 9 or polypeptides having at least 80% sequence identity hereto, wherein the polypeptide has hexosaminidase activity.

Some aspect relates to a detergent composition as defined herein comprising at least 0.0001 ppm of active enzyme polypeptide, wherein the enzyme polypeptide is selected from the group consisting of SEQ ID NO 7, SEQ ID NO 8, SEQ ID NO 9, SEQ ID NO 10 and SEQ ID NO 11 or polypeptides having at least 80% sequence identity hereto, wherein the polypeptide has hexosaminidase activity.

The compositions as defined herein, if not indicated otherwise, may comprise from 0-65 wt %, from about 2 wt % to about 60 wt %, from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactants, amphoteric and/or non-ionic surfactants. "About", as used herein in relation to a numerical value means said value ±10%, such as ±5%. "About 5 wt %" thus means from 4.5 to 5.5 wt %, such as from 4.75 to 5.25 wt %.

If not indicated otherwise, the surfactant may be generally selected among nonionic, anionic and/or amphoteric surfactants. In general, bleach-stable surfactants are useful. Non-limiting anionic surfactants are sulphate surfactants and in particular alkyl ether sulphates, especially C9-C15 alcohol ether sulfates, such as ethoxylates or mixed ethoxylates/propoxylates, such as those with 1 to 30 EO, C12-C15 primary alcohol ethoxylate, such as those with 1 to 30 EO, C8-C16 ester sulphates and C10-C14 ester sulphates, such as mono dodecyl ester sulphates. Non-limiting examples of anionic surfactants include sulfates and sulfonates, in particular, linear alkylbenzenesulfonates (LAS), in particular C12-C13 alkyl benzene sulfonates, isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SD S), fatty alcohol sulfates (FAS), primary alcohol sulfates (PAS), alcohol ether sulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof. The anionic surfactants are added to the detergent in the form of salts. Suitable cations in these salts are alkali metal ions, such as sodium, potassium and lithium and ammonium salts, for example (2-hydroxyethyl) ammonium, bis(2-hydroxyethyl) ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™, Lutensol™ and Pluronic™ range from BASF, Dehypon™ series from Cognis and Genapol™ series from Clariant.

In various embodiments, said surfactant comprises at least one alkyl ether sulfate. Non-limiting alkyl ether sulfates are those of formula (I)

$$R^1-O-(AO)_n-SO_3^-X^+ \quad (I).$$

In formula (I) $R^1$ represents a linear or branched, substituted or unsubstituted alkyl group, such as a linear, unsubstituted alkyl group, or a fatty alcohol moiety. Non-limiting $R^1$ moieties are selected from the group consisting of decyl, undecyl, dodecyl, tridecyl, tetradecyl, pentadecyl, hexadecyl, heptadecyl, octadecyl, nonadecyl, eicosyl moieties and mixtures thereof, wherein those groups with an even number of carbon atoms are useful. Non-limiting $R^1$ moieties are derived from $C_{10}$-$C_{18}$ fatty alcohols, such as those derived from coconut oil alcohols, tallow fatty alcohols, lauryl, myristyl, cetyl or stearyl alcohol or from C10-C20 oxoalcohols.

AO represents an ethyleneoxide (EO) or propyleneoxide (PO) group, such as an ethyleneoxide group. The index n represents an integer from 1 to 50, such as from 1 to 20 or from 1 to 10. In a non-limiting embodiment, n is 1, 2, 3, 4, 5, 6, 7 or 8. X represents a monovalent cation or the n-th part of an n-valent cation, are alkali metal cations, specifically $Na^+$ and $K^+$, such as $Na^+$. Further cations $X^+$ may be selected from $NH_4^+$, ½ $Zn^{2+}$, ½ $Mg^{2+}$ ½ $Ca^{2+}$, ½ $Mn^{2+}$, and combinations thereof.

In various embodiments, the detergent compositions comprise an alkyl ether sulfate selected from fatty alcohol ether sulfates of formula (II)

(II)

wherein k=9 to 19, and n=1, 2, 3, 4, 5, 6, 7 or 8. Non-limiting examples are $C_{10-16}$ fatty alcohol ether sulfates with 1-7 EO (k=9-15, n=1-7), such as the $C_{12-14}$ fatty alcohol ether sulfates with 1-3, particularly 2 EO (k=11-13, n=1-3 or 2), more particularly the sodium salts thereof. One specific embodiment thereof is lauryl ether sulfate sodium salt with 2 EO. The level of ethoxylation is an average value and can, for a specific compound, be an integer or fractional number.

In various embodiments, the surfactant comprises at least one alkyl benzene sulfonate. Said alkyl benzene sulfonate may be present alternatively to the above alkyl ether sulfate or in addition to it.

Exemplary alkyl benzene sulfonates include, but are not limited to linear and branched alkyl benzene sulfonates, such as linear alkyl benzene sulfonates. Exemplary compounds are those of formula (III)

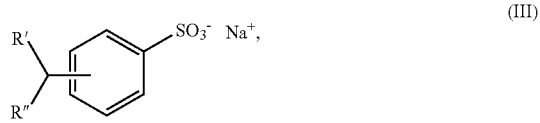

(III)

wherein R' and R" are independently H or alkyl and combined comprise 9 to 19, such as 9 to 15 or 9 to 13 carbon atoms. Non-limiting examples are dodecyl and tridecyl benzene sulfonates, in particular the sodium salts thereof.

In addition or alternatively, the compositions may further comprise one or more nonionic surfactants. Non-limiting nonionic surfactants are those of formula (IV)

$$R^2-O-(AO)_m-H \quad (IV),$$

wherein $R^2$ represents a linear or branched substituted or unsubstituted alkyl moiety, AO represents an ethylene oxide (EO) or propylene oxide (PO) group and m is an integer from 1 to 50.

In formula (IV) $R^2$ represents a linear or branched, substituted or unsubstituted alkyl group, such as a linear, unsubstituted alkyl group, such as a fatty alcohol group. Non-limiting groups are $R^2$ are selected from decyl, undecyl, dodecyl, tridecyl, tetradecyl, pentadecyl, hexadecyl, heptadecyl, octadecyl, nonadecyl, eicosyl groups and combinations thereof, wherein those groups with an even number of carbon atoms are useful. Non-limiting examples are $R^2$ groups derived from $C_{12}$-$C_{18}$ fatty alcohols, such as coconut oil alcohol, tallow oil alcohol, lauryl, myristyl, cetyl or stearyl alcohol or from $C_{10}$-$C_{20}$ oxoalcohols.

AO represents an ethyleneoxide (EO) or propyleneoxide (PO) group, such as an ethyleneoxide group. The index m represents an integer from 1 to 50, such as from 1 to 20 or from 1 to 6. In a non-limiting embodiment, m is 1, 2, 3, 4 or 5, or 3-5, as higher degrees of ethoxylation may negatively influence viscosity and stability.

In various embodiments, the detergent compositions comprise an alkyl ether selected from fatty alcohol ethers of formula (V)

(V)

wherein k=11 to 19, m=1, 2, 3, 4, 5, 6, 7 or 8. Non-limiting examples are $C_{12-18}$ fatty alcohols with 1-6 EO (k=11-17, m=1-5 in formula (V)). Non-limiting examples are $C_{12-14}$ alcohols having 1-5 EO, such as are $C_{12}$-14 alkyl ethers with 3-5 EO, in particular lauryl ether with 5 EO.

The detergent compositions may further include other nonionic surfactants, such as alkyl glucosides of the general formula $RO(G)_x$, where R is a primary linear or 2-methyl-branched aliphatic radical containing 8 to 22 or from 12 to 18 carbon atoms and G stands for a glucose unit. The degree of oligomerization x, which indicates the distribution of monoglucosides and oligoglucosides, is a number of 1 to 10 or a number of 1.2 to 1.4.

In various embodiments, the composition comprises at least two anionic surfactants, e.g. at least one alkyl ether sulfate and at least one alkyl benzene sulfonate, and optionally an alkyl ether.

Suitable amphoteric surfactants comprise betains. Non-limiting examples betaines are the alkylbetaines, the alkylamidobetaines, the imidazolinium betaines, the sulfobetaines (INCI Sultaines) and the phosphobetaines. Examples of suitable betaines and sulfobetaines are the following compounds designated as INCI: almondamidopropyl betaines, apricotam idopropyl betaines, avocadamidopropyl betaines, babassuamidopropyl betaines, behenamide idopropyl betaines, behenyl betaines, betaines, canola idopropyl betaines, caprylic/capram idopropyl betaines, carnitines, cetyl betaines, Cocamidoethyl betaines, cocamidopropyl betaines, cocam idopropyl hydroxysultaines, cocobetaines, coco-hydroxysultaines, coco/oleam idopropyl betaines, coco-sultaines, decyl betaines, dihydroxyethyl oleyl glycinates, dihydroxyethyl soy glycinates, dihydroxyethyl stearyl glycinates, dihydroxyethyl tallow glycinates, dimethicones propyl PG Betaines, erucam idopropyl hydroxysultaines, hydrogenated tallow betaines, isostearam idopropyl betaines, lauram idopropyl betaines, lauryl betaines, lauryl hydroxysultaine, lauryl sultaines, milkamidopropyl betaines, minkam idopropyl betaines, myristamine idopropyl betaines, myristyl betaines, oleam idopropyl betaines, oleam idropy Hydroxysultain, Oleyl Betaine, Olivamidopropyl Betaine, Palmam Idopropyl Betaine, Palm Itam Idopropyl Betaine, Palmitoyl Carnitine, Palm Kernelamidopropyl Betaine, Polytetrafluoroethylene Acetoxypropyl Betaine, Ricinoleam Idopropyl Betaine, Sesamidopropyl Betaine, Soyamidopropyl Betaine, Stearam Idopropyl Betaine, Stearyl Betaine, Tallowam Idopropyl Betaine, Tallowamidopropyl Hydroxysultaine, Tallow Betaine, Tallow Dihydroxyethyl Betaine, Undecylenamidopropyl Betaine and Wheat Germamidopropyl Betaine. A betaine is, for example, cocamidopropyl betaine (cocoamidopropylbetaine). The betaines are for dishwashing compositions, such as hand dishwashing detergent compositions.

Further suitable surfactants include the amine oxides. The amine oxides suitable include alkylamine oxides, in particular alkyldimethylamine oxides, alkylamidoamine oxides and alkoxyalkylamine oxides. Examples of suitable amine oxides are the following compounds designated as INCI: Almond amidopropylamine oxides, Babassu amidopropylamine oxides, Behenamine oxides, Cocamidopropyl Amine oxides, Cocamidopropylamine oxides, Cocamine oxides, Coco-Morpholine oxides, Decylamine oxides, Decyltetradecylamine oxides, Diaminopyrimidine oxides, Dihydroxyethyl C8-10 alkoxypropylamines oxides, Dihydroxyethyl C9-11 alkoxypropylamines oxides, dihydroxyethyl C12-15 alkoxypropylamines oxides, dihydroxyethyl cocamine oxides, dihydroxyethyl lauramine oxides, dihydroxyethyl stearamines oxides, dihydroxyethyl tallowamine oxides, hydrogenated palm kernel amine oxides, hydrogenated tallowamine oxides, hydroxyethyl hydroxypropyl C12-15 alkoxypropylamines oxides, isostearamidopropylamines Oxides, isostearamidopropyl morpholine oxides, lauram idopropylamine oxides, lauramine oxides, methyl morpholine oxides, milkamidopropyl amine oxides, mincamidopropylamine oxides, myristamine idopropylamine oxides, myristamine oxides, myristyl/cetyl amines Oxides, Oleam idopropylamine oxides, Oleamine oxides, Ol ivam idopropylamine oxides, Palmitamidopropylamine oxides, Palmitamine oxides, PEG-3 Lauramine oxides, Potassium dihydroxyethyl Cocamine oxides phosphates, Potassium Trisphosphonomethylamine oxides, Sesamidopropylamine oxides, Soyamidopropylamine oxides, Stearam idopropylam ine oxides, stearamines Oxides, Tallowam idopropylam ine oxides, Tallowamine oxides, Undecylenamidopropylamine oxides and Wheat Germam idopropylam ine oxides. A amine oxide is, for example, cocamidopropylamine oxides (cocoamidopropylamine oxide).

For automatic dishwashing applications, low-foaming nonionic surfactants are used, in particular alkoxylated, especially ethoxylated, low-foaming nonionic surfactants. With particular preference, the automatic dishwashing detergents contain nonionic surfactants from the group of the alkoxylated alcohols. Particular preference is given to nonionic surfactants which have a melting point above room temperature. Nonionic surfactants having a melting point above 20° C., such as above 25° C., alternatively between 25 and 60° C. and especially between 26.6 and 43.3° C., are useful. Non-limiting surfactants are those from the groups of alkoxylated nonionic surfactants, in particular the ethoxylated primary alcohols and mixtures of these surfactants with structurally more complex surfactants such as polyoxypropylene/polyoxyethylene/polyoxypropylene ((PO/EO/PO) surfactants). Such (PO/EO/PO) nonionic surfactants are also characterized by good foam control. Non-limiting examples nonionic surfactants are those containing alternating ethylene oxide and different alkylene oxide units. Among these, in turn, surfactants with EO-AO-EO-AO blocks are useful, with one to ten EO or AO groups before one block from the other group follows. Exemplary nonionic surfactants are those having a C9-alkyl group with 1 to 4 ethylene oxide units followed by 1 to 4 propylene oxide units, followed by 1 to 4 ethylene oxide units followed by 1 to 4 propylene oxide units. Preference is given in particular to end-capped, poly (oxyalkylated) nonionic surfactants with the end-cap being a linear or branched, saturated or unsaturated, aliphatic or aromatic hydrocarbon radical R having 1 to 30 carbon atoms. The alkyl groups may also comprise hydroxyl groups. The group of these nonionic surfactants include, for example, the C4-22 fatty alcohol $(EO)_{10-50}$-2-hydroxyalkyl ethers, in particular also the C8-12 fatty alcohol $(EO)_{22}$-2-hydroxydecyl ethers and the C4-22 fatty alcohol $(EO)_{40-80}$-2-hydroxyalkyl ethers. The composition, as defined herein, may comprise, if not indicated otherwise, from 0-65 wt %, for example about 1 wt % to about 65 wt %, from about 5 wt % to about 50 wt %, such as from about 40 wt % to 65 wt %, such as 50-65 wt %, particularly about 20 wt % to about 65 wt %, particularly from 10 wt % to 50 wt % of at least one builder.

Generally and if not indicated otherwise, the builder may be selected from citrate, carbonate, silicate, aluminosilicate (zeolite) and combinations thereof. Suitable builders also include phosphonates, polyphosphonates, bicarbonates, borates, and further polycarboxylates. Citrate builders, e.g., citric acid and soluble salts thereof (particularly sodium salt), are particularly suitable water-soluble organic builders. Citrates can be used in combination with zeolite, silicates like the BRITESIL types, and/or layered silicate builders. The builder and/or co-builder may be any chelating agent that forms water-soluble complexes with Ca and Mg. Any builder and/or co-builder known in the art for use in cleaning detergents may be utilized. Non-limiting examples of builders include zeolites, in particular zeolite A or P or X, carbonates such as sodium carbonate, soluble silicates such as sodium metasilicate, layered silicates (e.g., SKS-6 from Hoechst), and (carboxymethyl)inulin (CMI), and combinations thereof. Further non-limiting examples of builders include aminocarboxylates, aminopolycarboxylates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid- N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonic acid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP). Non-limiting examples are HEDP and DTPMP.

Suitable silicates are crystalline, layered sodium silicates of the general formula $NaMSi_xO_{2+1}*yH_2O$, wherein M is sodium or H, x a number of from 1.9 to 4 and y a number of from 0 to 20 and x is 2, 3 or 4. Such silicates are for example disclosed in EP-A-0 164 514. Non-limiting examples are silicates in which M is sodium and is 2 or 3. Non-limiting examples are β- and δ-sodium disilicate $Na_2Si_2O_5*yH_2O$.

The compositions may also comprise phosphates, diphosphates (pyrophosphates) and/or triphosphates such as sodium triphosphate (STP or STPP). In a non-limiting embodiment, all compositions disclosed herein are phosphate-free, i.e. do not contain deliberately added phosphate, in particular the phosphate content is below 1 wt %, such as less than 0.5 wt %, or less than 0.1 wt %, relative to the total weight of the composition. In alternative embodiments, the composition also relates to phosphate-free cleaning compositions in general that contain the polypeptides. In one aspect, the composition thus features a phosphate-free cleaning composition comprising any one or more of the polypeptides having hexosaminidase activity disclosed herein.

If not indicated otherwise, the composition may also contain 0-50% by weight, such as about 5% to about 30%, of a detergent co-builder. The composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid. Further exemplary builders and/or co-builders are described in, e.g., WO 09/102854, U.S. Pat. No. 5,977,053.

Non-limiting examples as co-builders are acrylate-containing water-soluble polymers, such as alkali metal salts of polyacrylic acid or polymethacrylic acid, for example those having a molecular weight $M_w$ in the range of 600 to 750,000 g/mol, as determined by gel permeation chromatography (GPC) according to DIN 55672-1:2007-08 with THF as an eluent.

Non-limiting polymers are polyacrylates with a molecular weight $M_w$ of 1,000 to 15,000 g/mol, alternatively, due to their solubility, are short-chain polyacrylates with a molecular weight $M_w$ of 1,000 to 10,000 g/mol, or from 1,000 to 5,000 g/mol.

Non-limiting acrylates are alkali metal salts of polymers of acrylic acid, such as the sodium salts, in particular those with molecular weights in the range of 1,000 to 10,000 g/mol or 1,000 to 5,000 g/mol. Suitable acrylates are commercially available, for example under the tradename Acusol® from Dow Chemical. Suitable are also copolymers of acrylates, in particular those of acrylic acid and methacrylic acid, and acrylic acid or methacrylic acid and maleic acid.

In embodiments, the compositions comprise a sulfopolymer, such as a copolymer comprising an ethylenically unsaturated sulfonate/sulfonic acid as a co-monomer. Particularly suitable are monomers of allyl sulfonic acids, such as allyloxybenzene sulfonic acid and methallyl sulfonic acid. Non-limiting sulfonic acid group-containing monomers are 1-acrylamido propane sulfonic acid-1,2-acylamido-2-propanesulfonic acid, 2-acrylamido-2-methyl-1-propanesulfonic acid, 2-methacrylamido-2-methyl-1-propanesulfonic acid, 3-methacrylamdo-2-hydroxypropanesulfonic acid, allylsulfonic acid, methallylsulfonic acid, allyloxybenzenesulfonic acid, methallyloxybenzolsulfonsäure, 2-hydroxy-3-(2-propenyloxy)propanesulfonic acid, 2-methyl-2-propenl-sulfonic acid, styrenesulfonic acid, vinylsulfonic acid, 3-sulfopropyl, 3-sulfo-propyl, sulfomethacrylamide, sulfomethylmethacrylamide and mixtures of said acids or their water-soluble salts.

The sulfopolymers are copolymers of the afore-described monomers with unsaturated carboxylic acids. Non-limiting unsaturated carboxylic acids are acrylic acid, methacrylic acid, ethacrylic acid, chloroacrylic acid, alpha-canoacrylic acid, crotomc acid, alpha-phenyl-acrylic acid, maleic acid, maleic anhydride, fumaric acid, itaconic acid, citraconic acid, methylenemalonic acid, sorbic acid, cinnamic acid or mixtures thereof. Usable are of course also the unsaturated dicarboxylic acids. Non-limiting examples are copolymers with acrylates, in particular with acrylic acid and methacrylic acid, and acrylic acid or methacrylic acid and maleic acid.

Such polymers are, for example, commercially available under the trade names Acusol®590 or Acusol® 588 from Dow Chemical.

In one aspect, the cleaning compositions comprise a polypeptide as defined herein and at least one sulfopolymer, as defined above. Such compositions are dishwashing compositions.

In one embodiment, the builder is a non-phosphorus based builder such as citric acid and/or methylglycine-N,N-diacetic acid (MGDA) and/or glutamic-N,N-diacetic acid (GLDA) and/or salts thereof. The compositions disclosed herein may, if not indicated otherwise, contain 0-30% by weight, such as about 1% to about 20%, such as about 1% to about 10%, such as about 1% to about 5%, such as about 10% to about 30%, such as about 5% to about 10% or such as about 10% to about 20% by weight (wt %) of a bleaching system. Any bleaching system comprising components known in the art for use in cleaning detergents may be utilized. Suitable bleaching system components include sources of hydrogen peroxide; sources of peracids; and bleach catalysts or boosters.

Suitable sources of hydrogen peroxide are inorganic persalts, including alkali metal salts such as sodium percarbonate and sodium perborates (usually mono- or tetrahydrate), and hydrogen peroxide-urea (1/1).

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4[(3,5,5-trimethylhexanoyl) oxy] benzene-1-sulfonate (ISONOBS), sodium 4-(dodecanoyloxy) benzene-1-sulfonate (LOBS), sodium 4-(decanoyloxy) benzene-1-sulfonate, 4-(decanoyloxy) benzoic acid (DOBA), sodium 4-(nonanoyloxy) benzene-1-sulfonate (NOBS), and/or those disclosed in WO98/17767 A family of bleach activators of interest was disclosed in EP624154 and in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

The bleaching system may also include a bleach catalyst or booster.

Some non-limiting examples of bleach catalysts that may be used in the compositions include manganese oxalate, manganese acetate, manganese-collagen, cobalt-amine catalysts and manganese triazacyclononane (MnTACN) catalysts; non-limiting are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

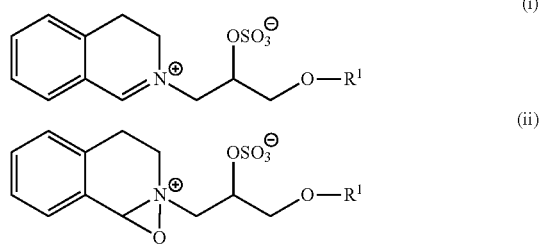

(iii) and mixtures thereof; wherein each R1 is independently a branched alkyl group containing from 9 to 24 carbons or linear alkyl group containing from 11 to 24 carbons, such as each R1 is independently a branched alkyl group containing from 9 to 18 carbons or linear alkyl group containing from 11 to 18 carbons, or each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

One aspect relates to the use of a composition as described above for deep-cleaning of an item, such as a textile.

The polypeptides having hexosaminidase activity may be used in the described compositions for deep cleaning of items such as hard surfaces, textiles and/or fabric. In some aspects the polypeptides e.g. the polypeptides having at least at least 60%, such as at least 70%, such as at least 80% or such as at least 90% sequence identity the mature polypeptides of SEQ ID NO 2, SEQ ID NO 4, SEQ ID NO 6, SEQ ID NO 13 and SEQ ID NO 15 or to the mature polypeptide with SEQ ID NO 7, SEQ ID NO 8, SEQ ID NO 9, SEQ ID NO 10 and SEQ ID NO 11, have β-N-acetylglucosamininidase activity and in some aspects the hexosaminidase activity is β-N-acetylglucosamininidase activity and the polypeptide are β-N-acetylglucosamininidases One aspect relates to the use of a composition, as defined herein, comprising a polypeptide of the *Terribacillus* clade, wherein the polypeptide has hexosaminidase activity, such as N-acetylglucosaminidase activity and/or β-N-acetylglucosamininidase activity in a cleaning process, such as laundry and/or dish wash.

One aspect relates to the use of a composition, as defined herein, comprising a polypeptide comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).

One aspect relates to the use of a composition, as defined herein, comprising a polypeptide of the *Terribacillus* clade, wherein the polypeptide has hexosaminidase activity, such as N-acetylglucosaminidase activity and/or β-N-acetylglucosamininidase activity in a cleaning process, such as laundry and/or dish wash wherein the polypeptide comprises one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).

One aspect relates to the use of a composition, as defined herein, comprising a polypeptide of the *Terribacillus* clade e.g. comprising one or both of the motifs GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide has hexosaminidase activity and wherein the polypeptide is a polypeptide having at least 60% e.g. 80%, 85%, 90% or 95% sequence identity to the mature polypeptides shown in SEQ ID NO 7, SEQ ID NO 8, SEQ ID NO 9, SEQ ID NO 10 or SEQ ID NO 11 for deep cleaning of an item, wherein the item is a textile. In one aspect the polypeptide of the *Terribacillus* clade having hexosaminidase activity is used for preventing, reducing or removing the stickiness of an item. In one aspect the polypeptide of the *Terribacillus* clade having hexosaminidase activity can further be used for pre-treating stains on textile such as textile.

One aspect relates to the use of a composition, as defined herein, comprising a polypeptide of the *Terribacillus* clade having hexosaminidase activity for preventing, reducing or removing re-deposition of soil during a wash cycle.

Further, one aspect relates to the use of a composition, as defined herein, comprising a polypeptide of the *Terribacillus* clade having hexosaminidase activity for preventing, reducing or removing the adherence of soil to an item. In one embodiment, the item is textile. When the soil does not adhere to the item, the item appears cleaner. Thus, Thus, the use of a composition, as defined herein, may include a polypeptide of the *Terribacillus* clade having hexosaminidase activity for maintaining or improving the whiteness of the item.

When items like T-shirts or sportswear are used, they are exposed to bacteria from the body of the user and from the rest of the environment in which they are used. This may cause malodor on the item even after the item is washed. The present composition therefore also concerns removal or reduction of malodor on textile. The malodor may be caused by bacteria producing compounds with an unpleasant smell. One example of such unpleasant smelling compounds is E-2-nonenal. The malodor can be present on newly washed textile which is still wet. Or the malodor can be present on newly washed textile, which has subsequently been dried. The malodor may also be present on textile, which has been stored for some time after wash. The present composition relates to reduction or removal of malodor such as E-2-nonenal from wet or dry textile.

One aspect relates to the use of a composition, as defined herein, comprising a polypeptide of the *Terribacillus* clade e.g. comprising one or more motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO 24), wherein the polypeptide has hexosaminidase activity, such as N-acetylglucosaminidase activity and/or β-N-acetylglucosamininidase activity and wherein the polypeptide is a polypeptide having at 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptides shown in SEQ ID NO 7, SEQ ID NO 8, SEQ ID NO 9, SEQ ID NO 10 or SEQ ID NO 11,
 (i) for preventing, reducing or removing stickiness of the item;
 (ii) for pretreating stains on the item;
 (iii) for preventing, reducing or removing redeposition of soil during a wash cycle;
 (iv) for preventing, reducing or removing adherence of soil to the item;
 (v) for maintaining or improving whiteness of the item;
 (vi) for preventing, reducing or removal malodor from the item,
 wherein the item is a textile.

A cleaning e.g. detergent composition may further comprise one or more additional components, such as at least one adjunct ingredient e.g. a detergent adjunct. The detergent adjunct ingredient may include surfactants and builders and/or chelators such as those described above. The adjunct ingredients may also be any of the following flocculating aid, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, bittering agents and/or pigments.

In various embodiments, cleaning compositions may include the polypeptides having hexosaminidase activity, as described herein, and any one or more of an adjunct ingredient selected from bittering agents and organic solvents, such as glycerol and 1,2-propane diol. In one embodiment, the detergent adjunct ingredient is a builder or a clay soil removal/anti-redeposition agent.

In one embodiment, detergent adjunct ingredient is an enzyme. The one or more enzymes may be selected from the group consisting of proteases, lipases, cutinases, amylases, carbohydrases, cellulases, pectinases, mannanases, arabinases, galactanases, xylanases and oxidases.

In addition to the polypeptides having hexosaminidase activity comprising the polypeptides of SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition may further comprise cellulases. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase polypeptides such as those described in WO 94/07998, EP 0 531 315, U.S. Pat. Nos. 5,457,046, 5,686,593, 5,763,254, WO 95/24471, WO 98/12307 and PCT/DK98/00299. Example of cellulases exhibiting endo-beta-1,4-glucanase activity (EC 3.2.1.4) are those having described in WO02/099091. Other examples of cellulases include the family 45 cellulases described in WO96/29397, and especially polypeptides thereof having substitution, insertion and/or deletion at one or more of the positions corresponding to the following positions in SEQ ID NO 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, such as selected among P19A, G20K, Q44K, N48E, Q119H or Q146R. Commercially available cellulases include Celluzyme™, Celluclean and Carezyme™ (Novozymes A/S), Clazinase™, and Puradax HA™ (Genencor International Inc.), and KAC-500(B)™ (Kao Corporation).

In addition to the polypeptides having hexosaminidase activity comprising SEQ ID NO 7, SEQ ID NO 8, SEQ ID NO 9 SEQ ID NO 10, SEQ ID NO 11 or a polypeptide having hexosaminidase activity and having at least 60% sequence identity hereto the cleaning composition may further comprise proteases. Suitable proteases include those of bacterial, fungal, plant, viral or animal origin e.g. vegetable or microbial origin. Microbial origin is useful. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from e g family M4 or other metalloprotease such as those from M5, M7 or M8 families. The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family Examples of subtilases are those derived from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146. A further non-limiting protease is the alkaline protease from *Bacillus lentus* DSM 5483, as described for example in WO95/23221, and variants thereof which are described in WO92/21760, WO95/23221, EP1921147 and EP1921148 Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/01176 8, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 compared to SEQ ID NO 1 of WO2016/001449, wherein the positions correspond to the positions of the *Bacillus lentus* protease shown in SEQ ID NO 1 of WO2016/001449. Non-limiting subtilase variants may comprise any of the the mutations: S3T, V4I, S9R, S9E, A15T, S24G, S24R, K27R, N42R, S55P, G59E, G59D, N60D, N60E, V66A, N74D, N85S, N85R,G96S, G96A, S97G, S97D, S97A, S97SD, S99E, S99D, S99G, S99M, S99N, S99R, S99H, S101A, V102I, V102Y, V102N, S104A, G116V, G116R, H118D, H118N,N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A or R269H. The protease variants are variants of the *Bacillus lentus* protease (Savinase®) shown in SEQ ID NO 1 of WO2016/001449 or the *Bacillus amylolichenifaciens* protease (BPN') shown in SEQ ID NO 2 of WO2016/001449. The protease variants have at least 80% sequence identity to SEQ ID NO 1 or SEQ ID NO 2 of WO2016/001449.

A protease variant comprising a substitution at one or more positions corresponding to positions 171, 173, 175, 179, or 180 of SEQ ID NO 1 of WO2004/067737, wherein said protease variant has a sequence identity of at least 75% but less than 100% to SEQ ID NO 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000', Excellenz P1250', Eraser®, Preferenz P100™, Purafect Prime®, Preferenz P110™, Effectenz P1000', Purafect®™, Effectenz P1050', Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

In addition to the polypeptides having hexosaminidase activity comprising the polypeptides of SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition may further comprise lipases and cutinases which include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147). Other examples are lipase polypeptides such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500. Non-limiting commercial lipase products include Lipolase™, Lipex™; Lipolex™ and Lipoclean™ (Novozymes A/S), Lumafast (originally from Genencor) and Lipomax (originally from Gist-Brocades). Yet other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and polypeptides of the *M. smegmatis* perhydrolase in particular the S54V variant used in the commercial product Gentle Power Bleach from Huntsman Textile Effects Pte Ltd (WO10/100028).

In addition to the polypeptides having hexosaminidase activity comprising SEQ ID NO 7, SEQ ID NO 8, SEQ ID NO 9, SEQ ID NO 10, SEQ ID NO 11 or a polypeptide having hexosaminidase activity and having at least 60% sequence identity hereto the cleaning composition may further comprise amylases which can be used together with a polypeptide. The amylase may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839. Suitable amylases include amylases having SEQ ID NO 3 in WO 95/10603 or polypeptides having 90% sequence identity to SEQ ID NO 3 thereof. Non-limiting polypeptides are described in WO 94/02597, WO 94/18314, WO 97/43424 and SEQ ID NO 4 of WO 99/019467, such as polypeptides with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO 6 in WO 02/010355 or polypeptides thereof having 90% sequence identity to SEQ ID NO 6. Non-limiting polypeptides of SEQ ID NO 6 are those having a deletion in positions 181 and 182 and a substitution in position 193. Other amylases which are suitable are hybrid alpha-amylase comprising residues 1-33 of the alpha-amylase derived from B. amyloliquefaciens shown in SEQ ID NO 6 of WO 2006/066594 and residues 36-483 of the B. licheniformis alpha-amylase shown in SEQ ID NO 4 of WO 2006/066594 or polypeptides having 90% sequence identity thereof. Non-limiting polypeptides of this hybrid alpha-amylase are those having a substitution, a deletion or an insertion in one of more of the following positions: G48, T49, G107, H156, A181, N190, M197, I201, A209 and Q264. Non-limiting polypeptides of the hybrid alpha-amylase comprising residues 1-33 of the alpha-amylase derived from B. amyloliquefaciens shown in SEQ ID NO 6 of WO 2006/066594 and residues 36-483 of SEQ ID NO 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO 6 in WO 99/019467 or polypeptides thereof having 90% sequence identity to SEQ ID NO 6. Non-limiting polypeptides of SEQ ID NO 6 are those having a substitution, a deletion or an insertion in one or more of the following positions: R181, G182, H183, G184, N195, I206, E212, E216 and K269. Non-limiting amylases are those having deletion in positions R181 and G182, or positions H183 and G184. Additional amylases which can be used are those having SEQ ID NO 1, SEQ ID NO 3, SEQ ID NO 2 or SEQ ID NO 7 of WO 96/023873 or polypeptides thereof having 90% sequence identity to SEQ ID NO 1, SEQ ID NO 2, SEQ ID NO 3 or SEQ ID NO 7. Non-limiting polypeptides of SEQ ID NO 1, SEQ ID NO 2, SEQ ID NO 3 or SEQ ID NO 7 are those having a substitution, a deletion or an insertion in one or more of the following positions: 140, 181, 182, 183, 184, 195, 206, 212, 243, 260, 269, 304 and 476. Non-limiting polypeptides are those having a deletion in positions 181 and 182 or positions 183 and 184. Non-limiting amylase polypeptides of SEQ ID NO 1, SEQ ID NO 2 or SEQ ID NO 7 are those having a deletion in positions 183 and 184 and a substitution in one or more of positions 140, 195, 206, 243, 260, 304 and 476. Other amylases which can be used are amylases having SEQ ID NO 2 of WO 08/153815, SEQ ID NO 10 in WO 01/66712 or polypeptides thereof having 90% sequence identity to SEQ ID NO 2 of WO 08/153815 or 90% sequence identity to SEQ ID NO 10 in WO 01/66712. Non-limiting polypeptides of SEQ ID NO 10 in WO 01/66712 are those having a substitution, a deletion or an insertion in one of more of the following positions: 176, 177, 178, 179, 190, 201, 207, 211 and 264.

Further suitable amylases are amylases having SEQ ID NO 2 of WO 09/061380 or polypeptides having 90% sequence identity to SEQ ID NO 2 thereof. Non-limiting polypeptides of SEQ ID NO 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. Non-limiting polypeptides of SEQ ID NO 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Non-limiting amylase polypeptides of SEQ ID NO 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the polypeptides are C-terminally truncated and optionally further comprises a substitution at position 243 and/or a deletion at position 180 and/or position 181.

Other suitable amylases are the alpha-amylase having SEQ ID NO 12 in WO01/66712 or a variant having at least 90% sequence identity to SEQ ID NO 12. Non-limiting amylase polypeptides are those having a substitution, a deletion or an insertion in one of more of the following positions of SEQ ID NO 12 in WO01/66712: R28, R118, N174; R181, G182, D183, G184, G186, W189, N195, M202, Y298, N299, K302, 5303, N306, R310, N314; R320, H324, E345, Y396, R400, W439, R444, N445, K446, Q449, R458, N471, N484. Non-limiting amylases include polypeptides having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, such as a variant that additionally has substitutions in all these positions.

Other examples are amylase polypeptides such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

In addition to the polypeptides having hexosaminidase activity comprising the polypeptides of SEQ ID NO 7, SEQ ID NO 8, SEQ ID NO 9, or a polypeptide having hexosaminidase activity and having at least 60% sequence identity hereto the cleaning composition may further comprise peroxidases/oxidases including those of plant, bacterial or fungal origin. Chemically modified or protein engineered mutants are included. Examples of useful peroxidases include peroxidases from Coprinus, e.g., from C. cinereus, and polypeptides thereof as those described in WO 93/24618, WO 95/10602, and WO 98/15257. Commercially available peroxidases include Guardzyme™ (Novozymes A/S).

The cleaning composition enzyme(s) may be included in e.g. a detergent composition by adding separate additives containing one or more enzymes, or by adding a combined additive comprising these enzymes. A detergent additive, i.e., a separate additive or a combined additive, can be formulated, for example, as a granulate, liquid, slurry, etc. Non-limiting detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The cleaning/detergent compositions may, if not indicated otherwise, also contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), (carboxymethyl)inulin (CMI), and polycarboxylates such as PAA, PAA/PMA, polyaspartic acid, and lauiyl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The cleaning compositions may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light if subjected to ultraviolet light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially true when the composition is in the form of a unit dose pouch. Suitable hueing agents are also disclosed in, e.g. WO 2007/087257 and WO2007/087243.

The composition may further contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The cleaning compositions can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The cleaning composition may also include one or more dye transfer inhibiting agents. Suitable polymeric dye transfer inhibiting agents include, but are not limited to, polyvinylpyrrolidone polymers, polyamine-N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The cleaning compositions may also contain additional components that may tint articles being cleaned, such as fluorescent whitening agent or optical brighteners. Where present the brightener is at a level of about 0.01% to about 0.5%. Any fluorescent whitening agent suitable for use in a laundry detergent composition may be used in a laundry composition. The most commonly used fluorescent whitening agents are those belonging to the classes of diaminostilbene-sulfonic acid derivatives, diarylpyrazoline derivatives and biphenyl-distyryl derivatives. Examples of the diaminostilbene-sulfonic acid derivative type of fluorescent whitening agents include the sodium salts of: 4,4'-bis[(4-anilino-6-diethanolamino-s-triazin-2-yl)amino]stilbene-2,2'-disulfonate, 4,4'-bis[(4,6-dianilino-s-triazin-2-yl)amino]stilbene-2,2'-disulfonate, 4,4'-bis{4-anilino-6-[methyl(2-hydroxyethyl)amino]-s-triazin-2-ylamino}stilbene-2,2'-disulfonate, 4,4'-bis(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Non-limiting fluorescent whitening agents are Tinopal DMS and Tinopal CBS available from BASF. Tinopal DMS is the disodium salt of 4,4'-bis[(4-anilino-6-morpholino-s-triazin- 2-yl)amino]stilbene-2,2'-disulfonate. Tinopal CBS is the disodium salt of 2,2'-[biphenyl-4,4'-di(2,1-ethenediyl)]dibenzene-1-sulfonate. Another non-limiting example is the commercially available Parawhite KX, supplied by Paramount Minerals and Chemicals, Mumbai, India Other fluorescers suitable for use include the 1-3-diarylpyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The cleaning composition may also include one or more soil-release polymers which aid the removal of soils from fabrics such as cotton and polyester-based fabrics, in particular the removal of hydrophobic soils from polyester-based fabrics. The soil release polymers may for example be nonionic or anionic terephthalate-based polymers, polyvinylcaprolactam and related copolymers, vinyl graft copolymers or polyester polyamides; see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil-release polymers. Suitable graft co-polymers are described in more detail in WO 2007/138054, WO 2006/108856 and WO 2006/113314 (hereby incorporated by reference). Other soil-release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof.

The cleaning compositions may also include one or more anti-redeposition agents such as (carboxymethyl) cellulose (CMC), poly(vinyl alcohol) (PVA), homopolymers of acrylic acid, copolymers of acrylic acid and maleic acid, and ethoxylated polyethyleneimines. The cellulose based polymers described under soil-release polymers above may also function as anti-redeposition agents.

The cleaning composition may also contain one or more alternative or additional adjunct materials. Suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

The cleaning composition may be in any convenient form, e.g., a bar, a homogenous tablet, a tablet having two or more layers, a pouch having one or more compartments, such as 2 or more, such as 2, 3, 4 or 5 compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Non-limiting films are polymeric materials polymers which are formed into a film or sheet. Non-limiting polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, or polyvinyl alcohol copolymers and, hydroxypropyl methyl cellulose (HPMC). In a non-limiting embodiment, the level of polymer in the film for example PVA is at least about 60%. An average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

Methods for using the compositions in laundering of textile and fabrics, such as house hold laundry washing and industrial laundry washing are also disclosed.

One aspect relates to a method for laundering an item comprising:
 a) expose of an item to a wash liquor comprising a detergent composition or the detergent composition as such;
 b) optionally completing at least one wash cycle; and
 c) optionally rinsing the item, wherein the item is a textile.

The compositions, as defined herein, may include the polypeptides in cleaning hard surfaces such as floors, tables, walls, roofs etc. as well as surfaces of hard objects such as cars (car wash) and dishes (dish wash).

One aspect relates to the use of a composition, as defined herein, comprising a polypeptide having hexosaminidase activity optionally comprising one or more motif(s) selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide is selected from the group consisting of SEQ ID NO 7, SEQ ID NO 8, SEQ ID NO 9, SEQ ID NO 10, SEQ ID NO 11 and polypeptides having at least 60% sequence identity hereto having hexosaminidase activity in a cleaning process such as laundering and/or hard surface cleaning.

Thus, one aspect relates to the use of a composition, as defined herein, comprising a polypeptide having hexosaminidase activity, optionally comprising one or more motif(s) selected from the group consisting of GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24), wherein the polypeptide is selected from the group consisting of SEQ ID NO 7, SEQ ID NO 8, SEQ ID NO 9, SEQ ID NO 10, SEQ ID NO 11 and polypeptides having at least 60% sequence identity in a cleaning process such as laundering and/or hard surface cleaning and wherein the polypeptide has improved deep cleaning properties, relative to a reference enzyme.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, a process may include laundering of fabrics and/or garments where the process comprises treating fabrics with a washing solution containing a cleaning composition, and at least one polypeptide. The cleaning process or a textile care process can for example be carried out in a machine washing process or in a manual washing process. The washing solution can for example be an aqueous washing solution containing a detergent composition.

The polypeptides comprised in the *Terribacillus* clade are thus particularly useful in composition comprising surfactants such as detergent compositions and the polypeptides may be used in cleaning processes such as laundry and dish wash.

In some aspects, compositions, as defined herein, may include one or more polypeptides of the clade of *Terribacillus* having a sequence identity to the mature polypeptide of SEQ ID NO 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 7.

In some aspects, compositions, as defined herein, may include one or more polypeptides of the clade of *Terribacillus* having a sequence identity to the mature polypeptide of SEQ ID NO 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 8.

In some aspects, compositions, as defined herein, may include one or more polypeptides of the clade of *Terribacillus* having a sequence identity to the mature polypeptide of SEQ ID NO 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 9.

In some aspects, compositions, as defined herein, may include one or more polypeptides of the clade of *Terribacillus* having a sequence identity to the mature polypeptide of SEQ ID NO 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 10.

In some aspects, compositions, as defined herein, may include one or more polypeptides of the clade of *Terribacillus* having a sequence identity to the mature polypeptide of SEQ ID NO 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have hexosaminidase activity. In one aspect, the polypeptides differ by up to 10 amino acids, e.g., 1, 2, 3, 4, 5, 6, 7, 8, 9, or 10, from the mature polypeptide shown in SEQ ID NO 11.

In an embodiment, the polypeptide has been isolated. A polypeptide used in the compositions comprises or consists of the amino acid sequence of SEQ ID NO 7 or an allelic variant thereof; or is a fragment thereof having hexosaminidase activity. In another aspect, the polypeptide comprises or consists of the mature polypeptide of SEQ ID NO 2. In another aspect, the polypeptide comprises or consists of amino acids 1 to 324 of SEQ ID NO 2.

In an embodiment, the polypeptide has been isolated. A polypeptide used in the compositions comprises or consists of the amino acid sequence of SEQ ID NO 8 or an allelic variant thereof; or is a fragment thereof having hexosaminidase activity. In another aspect, the polypeptide comprises or consists of the mature polypeptide of SEQ ID NO 4. In another aspect, the polypeptide comprises or consists of amino acids 1 to 324 of SEQ ID NO 4.

In an embodiment, the polypeptide has been isolated. A polypeptide used in the compositions comprises or consists of the amino acid sequence of SEQ ID NO 9 or an allelic variant thereof; or is a fragment thereof having hexosaminidase activity. In another aspect, the polypeptide comprises or consists of the mature polypeptide of SEQ ID NO 6. In another aspect, the polypeptide comprises or consists of amino acids 1 to 324 of SEQ ID NO 6.

In an embodiment, the polypeptide has been isolated. A polypeptide used in the compositions comprises or consists of the amino acid sequence of SEQ ID NO 10 or an allelic variant thereof; or is a fragment thereof having hexosaminidase activity. In another aspect, the polypeptide comprises or consists of the mature polypeptide of SEQ ID NO 13. In another aspect, the polypeptide comprises or consists of amino acids 1 to 324 of SEQ ID NO 13.

In an embodiment, the polypeptide has been isolated. A polypeptide used in the compositions comprises or consists of the amino acid sequence of SEQ ID NO 11 or an allelic variant thereof; or is a fragment thereof having hexosaminidase activity. In another aspect, the polypeptide comprises or consists of the mature polypeptide of SEQ ID NO 15. In another aspect, the polypeptide comprises or consists of amino acids 1 to 324 of SEQ ID NO 15.

In another embodiment, compositions, as defined herein, may include a polypeptide having hexosaminidase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO 1, 3, 5, 12 or 14 or (ii) the full-length complement of (i) (Sambrook et al., 1989, *Molecular Cloning, A Laboratory Manual*, 2d edition, Cold Spring Harbor, N.Y.). In an embodiment, the polypeptide has been isolated.

The polynucleotide of SEQ ID NO 1, SEQ ID NO 3, SEQ ID NO 5, SEQ ID NO 12 or SEQ ID NO 14 or a subsequence thereof, as well as the mature polypeptide of SEQ ID NO 2, SEQ ID NO 4, SEQ ID NO 6, SEQ ID NO 13, SEQ ID NO 15 or a fragment thereof may be used to design nucleic acid probes to identify and clone DNA encoding polypeptides having hexosaminidase activity from strains of different genera or species according to methods well known in the art. Such probes can be used for hybridization with the genomic DNA or cDNA of a cell of interest, following standard Southern blotting procedures, to identify and isolate the corresponding gene therein. Such probes can be considerably shorter than the entire sequence, but should be at least 15, e.g., at least 25, at least 35, or at least 70 nucleotides in length. In a non-limiting embodiment, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a polypeptide having hexosaminidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. To identify a clone or DNA that hybridizes with SEQ ID NO 1, 3, 5, 12 or 14 or a subsequence thereof, the carrier material is used in a Southern blot.

For purposes herein, hybridization indicates that the polynucleotide hybridizes to a labeled nucleic acid probe corresponding to (i) SEQ ID NO 1, SEQ ID NO 3, SEQ ID NO 5, SEQ ID NO 12 or SEQ ID NO 14; (ii) the mature polypeptide coding sequence of SEQ ID NO 1, SEQ ID NO 3, SEQ ID NO 5, SEQ ID NO 12 or SEQ ID NO 14; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, a composition, as defined herein, may include a polypeptide having hexosaminidase activity encoded by a polynucleotide having a sequence identity to the mature polypeptide coding sequence of SEQ ID NO 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, a composition, as defined herein, may include a polypeptide having hexosaminidase activity encoded by a polynucleotide having a sequence identity to the mature polypeptide coding sequence of SEQ ID NO 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, a composition, as defined herein, may include a polypeptide having hexosaminidase activity encoded by a polynucleotide having a sequence identity to the mature polypeptide coding sequence of SEQ ID NO 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, a composition, as defined herein, may include a polypeptide having hexosaminidase activity encoded by a polynucleotide having a sequence identity to the mature polypeptide coding sequence of SEQ ID NO 12 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, a composition, as defined herein, may include a polypeptide having hexosaminidase activity encoded by a polynucleotide having a sequence identity to the mature polypeptide coding sequence of SEQ ID NO 14 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to compositions, as defined herein, comprising variants of the mature polypeptide of SEQ ID NO 2, SEQ ID NO 4, SEQ ID NO 6, SEQ ID NO 13 or SEQ ID NO 15 comprising a substitution, deletion, and/or insertion at one or more (e.g., several) positions. In an embodiment, the number of amino acid substitutions, deletions and/or insertions introduced into the mature polypeptide of SEQ ID NO 7, SEQ ID NO 8, SEQ ID NO 9, SEQ ID NO 10 or SEQ ID NO 11 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for hexosaminidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. The polypeptides are hexosaminidase e.g. dispersins belonging to the *Terribacillus* clade. *Terribacillus* dispersins are β-hexosaminidases that specifically hydrolyzes β-1,6-glycosidic linkages of N-acetylglucosamine polymers, which may be found e.g. in biofilm. Dispersin B which belongs to a different clade than the polypeptides (hexosaminidases) contains three highly conserved acidic residues: an aspartic acid at residue 183 (D183), a glutamic acid at residue 184 (E184), and a glutamic acid at residue 332 (E332). Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage Dsplay (e.g., Lowman et al., 1991, *Biochemistry* 30: 10832-10837; U.S. Pat. No. 5,223, 409; WO 92/06204), and region-directed mutagenesis (Derbyshire et al., 1986, *Gene* 46: 145; Ner et al., 1988, *DNA* 7: 127). Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide. The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide. A fusion polypeptide is produced by fusing a polynucleotide encoding another polypeptide to a polynucleotide. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, 1 Ind. *Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Hexosaminidase Activity

A polypeptide having hexosaminidase activity may be obtained from microorganisms of any genus. The term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide is a *Terribacillus* polypeptide, e.g., a polypeptide obtained from *Terribacillus saccharophilus*. In a non-limiting aspect, the polypeptide is a polypeptide having at least 80% sequence identity to SEQ ID NO 7 and is obtained from *Terribacillus* e.g. *Terribacillus saccharophilus*.

In another aspect, the polypeptide is a *Terribacillus* polypeptide, e.g., a polypeptide obtained from *Terribacillus goriensis*. In a non-limiting aspect, the polypeptide is a polypeptide having at least 80% sequence identity to SEQ ID NO 8 and is obtained from *Terribacillus* e.g. *Terribacillus goriensis*.

In another aspect, the polypeptide is a *Terribacillus* polypeptide, e.g., a polypeptide obtained from *Terribacillus saccharophilus*. In a non-limiting aspect, the polypeptide is a polypeptide having at least 80% sequence identity to SEQ ID NO 9 and is obtained from *Terribacillus* e.g. *Terribacillus saccharophilus*.

In another aspect, the polypeptide is a *Terribacillus* polypeptide, e.g., a polypeptide obtained from *Terribacillus saccharophilus*. In a non-limiting aspect, the polypeptide is a polypeptide having at least 80% sequence identity to SEQ ID NO 10 and is obtained from *Terribacillus* e.g. *Terribacillus saccharophilus*.

In another aspect, the polypeptide is a *Terribacillus* polypeptide, e.g., a polypeptide obtained from *Terribacillus saccharophilus*. In a non-limiting aspect, the polypeptide is a polypeptide having at least 80% sequence identity to SEQ ID NO 11 and is obtained from *Terribacillus* e.g. *Terribacillus saccharophilus*.

It will be understood that for the aforementioned species, the the composition encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present disclosure also relates to nucleic acid constructs comprising a polynucleotide described herein operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used.

Non-limiting terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Non-limiting terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor. Non-limiting terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra. The control sequence may also be an mRNA stabilizer region downstream of a promoter and upstream of the coding sequence of a gene which increases expression of the gene. Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471). The control sequence may also be a leader, a nontranslated region of an mRNA that is important for translation by the host cell. The leader is operably linked to the 5'-terminus of the polynucleotide encoding the polypeptide. Any leader that is functional in the host cell may be used. Non-limiting leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP). The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used. Non-limiting polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease. Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137. Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase. Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present disclosure also relates to recombinant expression vectors comprising a polynucleotide as described herein, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. A non-limiting example for use in an *Aspergillus* cell are *Aspergillus nidulans* or *Aspergillus oryzae* amdS and pyrG genes and a *Streptomyces hygroscopicus* bar gene. For use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present disclosure also relates to recombinant host cells, comprising a polynucleotide as described herein operably linked to one or more control sequences that direct the production of a polypeptide as described herein. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis,*

*Bacillus amyloliquefaciens*, *B. amyloliquefaciens* subsp. *plantarum*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus methylotrophicus*, *Bacillus pumilus*, *Bacillus safensis*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells. The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecta (Blastomycetes). Since the classification of yeast may change in the future, yeast shall be defined as described in Biology and Activities of Yeast (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present disclosure also relates to methods of producing a polypeptide as described herein, comprising (a) cultivating a cell, which in its wild-type form produces the polypeptide, under conditions conducive for production of the polypeptide; and optionally, (b) recovering the polypeptide. In one aspect, the cell is a *Terribacillus* cell. In another aspect, the cell is a *Terribacillus saccharophilus* cell. In one aspect, the cell is a *Terribacillus* cell. In another aspect, the cell is a *Terribacillus goriensis* cell.

The present disclosure also relates to methods of producing a polypeptide as described herein, comprising (a) cultivating a recombinant host cell as described herein under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having hexosaminidase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell expressing the polypeptide is used as a source of the polypeptide.

Formulation of Detergent Products

The cleaning composition may be in any convenient form, e.g., a bar, a homogenous tablet, a tablet having two or more layers, a pouch having one or more compartments, a regular or compact powder, a granule, a paste, a gel, or a regular, compact or concentrated liquid. Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Non-limiting films are polymeric materials polymers which are formed into a film or sheet. Non-limiting polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, such as polyvinyl alcohol copolymers and, hydroxypropyl methyl cellulose (HPMC). In a non-limiting embodiment, the level of polymer in the film for example PVA is at least about 60%. An average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The polypeptides disclosed herein may be added to laundry soap bars and used for hand washing laundry, fabrics and/or textiles. The term laundry soap bar includes laundry bars, soap bars, combo bars, syndet bars and detergent bars, with the term "cleaning composition" or "detergent composition", as used herein, also including such soap bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval. The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate. The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art. The laundry soap bar may be processed in conventional laundry soap bar making equipment such as but not limited to: mixers, plodders, e.g. a two stage vacuum plodder, extruders, cutters, logo-stampers, cooling tunnels and wrappers. The method may include preparing the laundry soap bars. The premix may be added to the soap at different stages of the process. For example, the premix containing a soap, hexosaminidase, optionally one or more additional enzymes, a protease inhibitor, and a salt of a monovalent cation and an organic anion may be prepared and the mixture is then plodded. The hexosaminidase and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The polypeptides disclosed herein may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D. Another example of formulation of enzymes using co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. The multi-enzyme co-granule may comprise a hexosaminidase and one or more enzymes selected from the group consisting of lipases, cellulases, xyloglucanases, perhydrolases, peroxidases, lipoxygenases, laccases, hemicellulases, proteases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The disclosure is further summarized in the following paragraphs:

1. Use of a cleaning composition, as defined herein, comprising polypeptide having hexosaminidase activity comprising one or more of the motif(s) GXDE (SEQ ID NO 18), [EQ][NRSHA][YVFL][AGSTC][IVLF] [EAQYN][SN] (SEQ ID NO 19), [VIM][LIV]G[GAV] DE[VI][PSA] (SEQ ID NO: 20), WND[SQR][IVL] [TLVM] (SEQ ID NO: 21), QSTL (SEQ ID NO 22), NKFFY (SEQ ID NO: 23) or NLD [DR]S (SEQ ID NO: 24) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, Cotton/Polyester, Polyester, Polyamide, Polyacryl and/or silk.
10. Use according to any of the preceding paragraphs, wherein the polypeptide is a polypeptide of paragraphs 47-61.
11. A composition comprising a polypeptide having hexosaminidase activity comprising one or more of the motif(s) GXDE (SEQ ID NO 18), [EQ][NRSHA][YVFL][AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23) or NLD[DR]S (SEQ ID NO: 24) and an adjunct ingredient.
12. Composition according to paragraph 11, wherein the polypeptide is the polypeptide of paragraphs 47-61.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, bittering agents and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

15. Composition according to any of the preceding composition paragraphs wherein the composition comprises from about 10 wt % to about 50 wt % of at least one builder, such as selected from citric acid, methyl-glycine-N, N-diacetic acid (MGDA) and/or glutamic acid-N, N-diacetic acid (GLDA) and mixtures thereof 16. Composition according to any of the preceding composition paragraphs wherein the polypeptide having hexosaminidase activity is selected from the group consisting of polypeptides having the amino acid sequence of SEQ ID NO 7, SEQ ID NO 8, SEQ ID NO 9, SEQ ID NO 10, SEQ ID NO 11 and polypeptides having at least 60% e.g. 80%, 85%, 90%, 95%, 98% or 99% sequence identity hereto.

17. Composition according to any of the preceding composition paragraphs wherein the polypeptide having hexosaminidase activity is the amino acid sequence of SEQ ID NO 7 or polypeptides having at least 60% e.g. 80%, 85%, 90%, 95%, 98% or 99% sequence identity hereto.

18. Composition according to any of the paragraphs 11 to 16, wherein the polypeptide having hexosaminidase activity is the amino acid sequence of SEQ ID NO 8 or polypeptides having at least 60% e.g. 80%, 85%, 90%, 95%, 98% or 99% sequence identity hereto.

19. Composition according to any of the paragraphs 11 to 16, wherein the polypeptide having hexosaminidase activity is the amino acid sequence of SEQ ID NO 9 or polypeptides having at least 60% e.g. 80%, 85%, 90%, 95%, 98% or 99% sequence identity hereto.

20. Composition according to any of the paragraphs 11 to 16, wherein the polypeptide having hexosaminidase activity is the amino acid sequence of SEQ ID NO 10 or polypeptides having at least 60% e.g. 80%, 85%, 90%, 95%, 98% or 99% sequence identity hereto.

21. Composition according to any of the paragraphs 11 to 16, wherein the polypeptide having hexosaminidase activity is the amino acid sequence of SEQ ID NO 11 or polypeptides having at least 60% e.g. 80%, 85%, 90%, 95%, 98% or 99% sequence identity hereto 22. Composition according to any of the preceding paragraphs comprising from about 5 wt % to about 40 wt % nonionic surfactants, and from about 0 wt % to about 5 wt % anionic surfactants.

23. Composition according to paragraph 22, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof 24. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

25. Composition according to any of the preceding composition paragraphs, wherein the enzyme is a protease, which is of animal, vegetable or microbial origin.

26. Composition according to any of the preceding composition paragraphs, wherein the protease is chemically modified or protein engineered.

27. Composition according to any of the preceding composition paragraphs, wherein the protease is a serine protease or a metalloprotease, such as an alkaline microbial protease or a trypsin-like protease.

28. Composition according to any of the preceding composition paragraphs, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

29. Composition according to any of the preceding composition paragraphs, wherein the composition is capable of reducing adhesion of EPS from bacteria selected from the group consisting of *Acinetobacter* sp., Aeromicrobium sp., *Brevundimonas* sp., *Microbacterium* sp., *Micrococcus luteus*, *Pseudomonas* sp., *Staphylococcus epidermidis*, *Staphylococcus aureus* and *Stenotrophomonas* sp. to a surface, or releasing the bacteria from a surface to which they adhere.

30. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

31. Composition according to any of the preceding composition paragraphs, wherein the composition is a cleaning composition selected from liquid detergent, powder detergent and granule detergent compositions.

32. A method for laundering an item comprising the steps of:
a. Exposing an item to a wash liquor comprising a polypeptide of paragraphs 46-56 or a composition according to any of paragraphs 11-31;
b. Completing at least one wash cycle; and
c. Optionally rinsing the item,
wherein the item is a textile.

33. A method for deep cleaning of an item, wherein the item is a textile, said method comprising; exposing an item to a wash liquor comprising a polypeptide, such as comprising one or more of the motif(s) GXDE (SEQ ID NO 18), [EQ][NRSHA][YVFL][AGSTC][IVLF][EA-QYN][SN] (SEQ ID NO 19), [VIM][LIV]G[GAV]DE [VI][PSA] (SEQ ID NO: 20), WND[SQR][IVL] [TLVM] (SEQ ID NO: 21), QSTL (SEQ ID NO 22), NKFFY (SEQ ID NO: 23) or NLD [DR]S (SEQ ID NO: 24), wherein the polypeptide is selected from the group consisting of polypeptides having at least 60% e.g. 80%, 85%, 90%, 95%, 98%, 99% or 100% sequence identity to the polypeptide shown in SEQ ID NO 7, SEQ ID NO 8, SEQ ID NO 9, SEQ ID NO 10 and SEQ ID NO 11.

34. Method according to paragraph 32 or 33, wherein the pH of the wash liquor is in the range of 1 to 11.
35. Method according to any of the preceding method paragraphs, wherein the pH of the wash liquor is in the range 5.5 to 11, such as in the range of 7 to 9, in the range of 7 to 8 or in the range of 7 to 8.5.
36. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.
37. Method according to any of the preceding method paragraphs, wherein the temperature of the wash liquor is from about 20° C. to about 40° C.
38. Method according to any of the preceding method paragraphs, wherein the temperature of the wash liquor is from about 15° C. to about 30° C.
39. Method according to any of the preceding method paragraphs, wherein stains present on the item is pretreated with a polypeptide of paragraphs 46-60 or a detergent composition according to any of paragraphs 11-31.
40. Method according to any of the preceding method paragraphs, wherein stickiness of the item is reduced.
41. Method according to any of the preceding method paragraphs, wherein redeposition of soil is reduced.
42. Method according to any of the preceding method paragraphs, wherein adherence of soil to the item is reduced or removed.
43. Method according to any of the preceding method paragraphs, wherein whiteness of the item is maintained or improved.
44. Method according to any of the preceding method paragraphs, wherein malodor is reduced or removed from the item.
45. Method according to any of the preceding method paragraphs, wherein the concentration of the polypeptide having hexosaminidase activity in the wash liquor is at least 0.001 mg of polypeptide, such as at least 0.05 mg of protein, or at least 1.0 mg of protein, or at least 1.5 mg of protein per liter of wash liquor, optionally the concentration of polypeptide in the wash liquor is in the range 0.0002 mg/L to 2 mg/L, such as 0.002 mg/L to 2 mg/L, such as 0.2 mg/L to 2 mg/L or in the range of 0.00001 mg/L to 10 mg/L or in the range of in the range of 0.0001 mg/L to 10 mg/L, or in the range of 0.001 mg/L to 10 mg/L, or in in the range of 0.01 mg/L to 10 mg/L per liter of wash liquor, optionally the concentration of the polypeptide is 0.00001% to 2 wt %, such as 0.0001 to 0.1 wt %, such as 0.0005 to 0.1 wt %, such as 0.001 to 0.1 wt %, such as 0.001 to 0.5 wt %, such as 0.002 to 0.5 wt % or 0.0002 to 0.09 wt % in the total detergent concentration.
46. A polypeptide having hexosaminidase activity, selected from the group consisting of:
   a. a polypeptide having at least 60% e.g. 80%, 85%, 90%, 95%, 98%, 99% or 100% sequence identity to the mature polypeptide shown in SEQ ID NO 7, 8, 9, 10 or 11;
   b. a polypeptide encoded by a polynucleotide that hybridizes under low stringency conditions with
      i. the mature polypeptide coding sequence of SEQ ID NO 1, 3, 5, 12 or 14,
      ii. the cDNA sequence thereof, or
      iii. the full-length complement of (i) or (ii);
   c. a polypeptide encoded by a polynucleotide having at least 60% e.g. 80%, 85%, 90%, 95%, 98%, 99% or 100% sequence identity to the mature polypeptide coding sequence of SEQ ID NO 1, 3, 5, 12 or 14 or the cDNA sequence thereof;
   d. a variant of the mature polypeptide of SEQ ID NO 7, SEQ ID NO 8, SEQ ID NO 9, SEQ ID NO 10 or SEQ ID NO 11 comprising a substitution, deletion, and/or insertion at one or more positions; and
   e. a fragment of the polypeptide of (a), (b), (c), or (d) that has hexosaminidase activity; and
   f. a polypeptide comprising one or more of the motif(s) GXDE (SEQ ID NO 18), [EQ][NRSHA][YVFL] [AGSTC][IVLF][EAQYN][SN] (SEQ ID NO 19), [VIM][LIV]G[GAV]DE[VI][PSA] (SEQ ID NO: 20), WND[SQR][IVL][TLVM] (SEQ ID NO: 21), QSTL (SEQ ID NO 22), NKFFY (SEQ ID NO: 23), NLD[DR]S (SEQ ID NO: 24).
47. The polypeptide of paragraph 46, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2, SEQ ID NO 4, SEQ ID NO 6, SEQ ID NO 13 or SEQ ID NO 15, or to the polypeptide shown in SEQ ID NO 7, SEQ ID NO 8, SEQ ID NO 9, SEQ ID NO 10 or SEQ ID NO 11.
48. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 2 or to the mature polypeptide shown in SEQ ID NO 7.
49. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 4 or to the mature polypeptide shown in SEQ ID NO 8.
50. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 6 or to the mature polypeptide shown in SEQ ID NO 9.
51. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 13 or to the mature polypeptide shown in SEQ ID NO 10.
52. The polypeptide of paragraph 46 or 47, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO 15 or to the mature polypeptide shown in SEQ ID NO 11

53. The polypeptide according to paragraph 46 to 52, which is encoded by a polynucleotide that hybridizes under low stringency conditions, low-medium stringency conditions, medium stringency conditions, medium-high stringency conditions, high stringency conditions, or very high stringency conditions with
  ii. the mature polypeptide coding sequence of SEQ ID NO 1, 3, 5, 12 or 14,
  iii. the cDNA sequence thereof, or
  iv. the full-length complement of (i) or (ii).
54. The polypeptide according to any of paragraphs 46-53, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, 3, 5, 12, 14 or the cDNA sequence thereof
55. The polypeptide according to any of paragraphs 46 to 54, comprising or consisting of the amino acids sequence shown in SEQ ID NO 7, SEQ ID NO 8, SEQ ID NO 9, SEQ ID NO 10 or SEQ ID NO 11 or the mature polypeptide of SEQ ID NO 2, SEQ ID NO 4, SEQ ID NO 6, SEQ ID NO 13 or SEQ ID NO 15.
56. The polypeptide according to any of paragraphs 46 to 55, which is a variant of SEQ ID NO 7, SEQ ID NO 8, SEQ ID NO 9, SEQ ID NO 10 or SEQ ID NO 11 comprising a substitution, deletion, and/or insertion at one or more positions.
57. A polynucleotide encoding the polypeptide according to any of paragraphs 46-56.
58. A nucleic acid construct or expression vector comprising the polynucleotide of paragraph 57 operably linked to one or more control sequences that direct the production of the polypeptide in an expression host.
59. A recombinant host cell comprising the polynucleotide of paragraph 57 operably linked to one or more control sequences that direct the production of the polypeptide.
60. A method of producing the polypeptide of any of paragraphs 46-56, comprising cultivating a cell, which in its wild-type form produces the polypeptide, under conditions conducive for production of the polypeptide.
61. The method of paragraph 60, further comprising recovering the polypeptide.
62. A method of producing a polypeptide according to any of paragraphs 46-56, comprising cultivating the host cell of paragraph 59 under conditions conducive for production of the polypeptide.
63. The method of paragraph 62, further comprising recovering the polypeptide.
64. A nucleic acid construct or expression vector comprising a gene encoding a protein operably linked to the polynucleotide of paragraph 57, wherein the gene is foreign to the polynucleotide encoding the signal peptide.
65. A recombinant host cell comprising a gene encoding a protein operably linked to the polynucleotide of paragraph 57, wherein the gene is foreign to the polynucleotide encoding the signal peptide.
66. A method of producing a protein, comprising cultivating a recombinant host cell comprising a gene encoding a protein operably linked to the polynucleotide of paragraph 62, wherein the gene is foreign to the polynucleotide encoding the signal peptide, under conditions conducive for production of the protein.
67. The method of paragraph 66, further comprising recovering the protein.
68. The recombinant host cell of paragraph 65 further comprising a polynucleotide encoding a second polypeptide of interest; such as an enzyme of interest; alternatively a secreted enzyme of interest; e.g. a hydrolase, isomerase, ligase, lyase, oxidoreductase, or a transferase; or the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase
69. The recombinant host cell of paragraph 65, wherein the second polypeptide of interest is heterologous or homologous to the host cell.
70. The recombinant host cell of paragraph 65 or 68, which is a fungal host cell; such as a filamentous fungal host cell; alternatively an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell; or an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.
71. The recombinant host cell of paragraph 65 or 68, which is a bacterial host cell; such as a prokaryotic host cell; alternatively a Gram-positive host cell; e.g. a *Bacillus, Clostridium, Enterococcus, Geobacillus, Lac-*

*tobacillus*, *Lactococcus*, *Oceanobacillus*, *Staphylococcus*, *Streptococcus*, or *Streptomyces* host cell; or a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* host cell.

72. Item laundered according to the method of any of paragraphs 32-45.

Some embodiments are summarized in the following paragraphs:

1. A cleaning composition, as defined herein, comprising at least 0.01 mg of active enzyme per gram of composition, wherein the polypeptide having hexosaminidase activity is selected from the group consisting of a polypeptide having at least 60% sequence identity to the mature polypeptide of SEQ ID NO: 2, 4 and 6.
2. The composition of paragraph 1, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 and 6.
3. The composition of any of paragraphs 1 or 2, comprising or consisting of SEQ ID NO: 7 or the mature polypeptide of SEQ ID NO: 2, SEQ ID NO: 8 or the mature polypeptide of SEQ ID NO: 4 or SEQ ID NO: 9 or the mature polypeptide of SEQ ID NO: 6.
4. The composition according to any of paragraphs 1 to 3 wherein the composition is a laundry or dish wash composition
5. The composition according to paragraphs 1-4, wherein the composition comprises up to about 50 wt %, from about 5 wt % to about 40 wt %, from about 5 wt % to about 30 wt %, from about 5 wt % to about 20 wt %, from about 5 wt % to about 10 wt % anionic surfactant.
6. The composition according to paragraph 5, wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % nonionic surfactant.
7. Use of a composition of any of paragraphs 1 to 6 for deep-cleaning of an item, wherein the item is a textile.
8. A laundering method for laundering an item comprising the steps of:
   Exposing an item to a wash liquor comprising a polypeptide selected from the group consisting of a polypeptide having at least 60% sequence identity to the mature polypeptide of SEQ ID NO: 2, 4 and 6 or a detergent composition according to any of paragraphs 1 to 6;
   Completing at least one wash cycle; and
   Optionally rinsing the item,
   wherein the item is a textile.
9. Use of a cleaning composition as defined herein comprising a polypeptide of the *Terribacillus* clade, wherein the polypeptide has hexosaminidase activity in a cleaning process, such as laundry and/or dish wash
10. Use of a cleaning composition as defined herein comprising a polypeptide of the *Terribacillus* clade, wherein the polypeptide has hexosaminidase activity for deep cleaning of an item, wherein the item is a textile.
11. Use according to paragraph 9 for preventing, reducing or removing stickiness of the item.
12. Use according to any of paragraphs 9 or 10 for preventing, reducing or removing redeposition of soil during a wash cycle.
13. Use according to any of the preceding paragraphs, wherein the polypeptide is selected from the group consisting of a polypeptide having at least 60% sequence identity to the mature polypeptide of SEQ ID NO: 2, 4 and 6 and at least one adjunct ingredient.
14. The use of paragraph 13, wherein the polypeptide has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 and 6.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Assays

Wash Assays

Mini Launder-O-Meter (MiniLOM) Model Wash System

MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.

Terg-O-toMeter (TOM) Wash Assay

The Terg-O-toMeter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines. Equipment: The water bath with 12 steel beakers and 1 rotating arm per beaker with capacity of 500 or 1200 mL of detergent solution. Temperature ranges from 5 to 80° C. The water bath must be filled up with deionised water. Rotational speed can be set up to 70 to 120 rpm/min. Set temperature in the Terg-O-toMeter and start the rotation in the water bath. Wait for the temperature to adjust (tolerance is +/−0.5° C.). All beakers shall be clean and without traces of prior test material. The wash solution with desired amount of detergent, temperature and water hardness is prepared in a bucket. The detergent is allowed to dissolve during magnet stirring for 10 min. Wash solution shall be used within 30 to 60 min after preparation. 800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

The following examples should not be construed as limiting the scope of the non-limiting embodiments.

Assays

Assay 1: Hexosaminidase Activity

The hexosaminidase activity of the mature polypeptides with SEQ ID NO 7, SEQ ID NO 8, and SEQ ID NO 9, was determined using 4-nitrophenyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 50 mM 2-(N-morpholino) ethanesulfonic acid pH 6 buffer, 1.5 mg/ml 4-nitrophenyl N-acetyl-β-D-glucosaminide and 20 µg/ml purified enzyme sample in a total reaction volume of 100 µl. Blank samples without enzyme were run in parallel. The reactions were carried out at 37° C. in a Thermomixer comfort (Eppendorf). After 10 minutes of incubation, 5 µl 1 M NaOH was added to each reaction mixture to stop the enzymatic reaction. The absorbance was read at 405 nm using a POLARstar Omega plate reader (BMG LABTECH) to estimate the formation of 4-nitrophenolate ion released because of enzymatic hydrolysis of the 4-nitrophenyl N-acetyl-β-D-glucosaminide substrate. The results are summarized in the table below. The table shows the average absorbance measured at 405 nm for each reaction performed in triplicates. It is seen that the absorbance is higher for the reaction carried out with SEQ ID NO 7, SEQ ID NO 8, SEQ ID NO 9, compared to blank without enzyme which demonstrates that SEQ ID NO 7, SEQ ID NO 8, SEQ ID NO 9 exhibit hexosaminidase activity.

TABLE 2

Hexosaminidase activity of SEQ ID NO 7, SEQ ID NO 8 and SEQ ID NO 9.

| Enzyme | Enzyme concentration | A405 nm | ΔA405 nm (A405 nm$_{sample}$ − A405 nm$_{blank}$) |
|---|---|---|---|
| Blank | 0 µg/ml | 0.158 | — |
| SEQ ID NO 7 | 50 µg/ml | 1.978 | 1.820 |
| SEQ ID NO 8 | 50 µg/ml | 1.715 | 1.557 |
| SEQ ID NO 9 | 50 µg/ml | 2.455 | 2.297 |

Assay 2: Hexosaminidase Activity

The hexosaminidase activity of the mature polypeptides with SEQ ID NO 7, SEQ ID NO 8, SEQ ID NO 9, and SEQ ID NO 10, was determined using 4-Methylumbeliferyl N-acetyl-β-D-glucosaminide (Sigma-Aldrich) as substrate. The enzymatic reaction was performed in triplicates in a 96 well flat bottom polystyrene microtiter plate (Thermo Scientific) with the following conditions: 20 mM 3-morpholinopropane-1-sulfonic acid pH 7 buffer, 5 mM 4-Methylumbeliferyl N-acetyl-β-D-glucosaminide and 20 nM purified enzyme sample in a total reaction volume of 200 Blank samples without enzyme were run in parallel. The reactions were carried out at ambient temperature 20-25° C. The reaction kinetics was followed immediately after mixing of enzyme and substrate using a SpectraMax M2e plate reader. Excitation wavelength was set to 368 nm and fluorescence emission reading was done at 448 nm. The reaction was followed for 30 min with 60 second intervals. Increase in fluorescence signal was used to estimate the formation of 4-Methylumbeliferyl ion released because of enzymatic hydrolysis of the 4-Methylumbeliferyl N-acetyl-β-D-glucosaminide substrate. The results are summarized in the table below. The table shows the average initial rate of reaction measured as relative fluorescence units per minute (RFU/min) using excitation at 368 nm and fluorescence emission at 448 nm for each reaction performed in triplicates. It is seen that the reaction initial rate is higher for the reaction carried out with SEQ ID NO 7, SEQ ID NO 8, SEQ ID NO 9, and SEQ ID NO 10 compared to blank without enzyme which demonstrates that SEQ ID NO 7, SEQ ID NO 8, SEQ ID NO 9, and SEQ ID NO 10 exhibit hexosaminidase activity.

TABLE 3

Hexosaminidase activity of SEQ ID NO 7, SEQ ID NO 8, SEQ ID NO 9, and SEQ ID NO 10. Δ Reaction initial rate (RFU/min) = (Reaction initial rate$_{sample}$ − Reaction initial rate$_{blank}$)

| Enzyme | Enzyme concentration | Reaction initial rate (RFU/min) | Δ Reaction initial rate (RFU/min) |
|---|---|---|---|
| Blank | 0 nM | 0.6 | — |
| SEQ ID NO 7 | 20 nM | 18.5 | 17.9 |
| SEQ ID NO 8 | 20 nM | 10.1 | 9.5 |
| SEQ ID NO 9 | 20 nM | 13.1 | 12.5 |
| SEQ ID NO 10 | 20 nM | 82.6 | 82.1 |

EXAMPLES

Example 1 Expression and Cloning of Hexosaminidases

The DNA encoding the hexosaminidase having the polypeptide comprised in SEQ ID NO 2 was isolated from a

*Terribacillus saccharophilus* strain obtained from ATCC in 1969 (ATCC12327). The DNA encoding the hexosaminidase having the polypeptide comprised in SEQ ID NOS 4 and 6 were isolated from a *Terribacillus goriensis* and a *Terribacillus saccharophilus* bacterial strains respectively, isolated from an environmental soil sample collected in USA. The DNA encoding the hexosaminidase having the polypeptide comprised in SEQ ID NOS 13 and 15 were isolated later from two *Terribacillus saccharophilus* strains, isolated from environmental samples collected in USA. Chromosomal DNA from the four *Terribacillus saccharophilus* strains and the *Terribacillus goriensis* strain was isolated by QIAamp DNA Blood Mini Kit (Qiagen, Hilden, Germany) and subjected to full genome sequencing using Illumina technology. The genome sequence was analyzed for protein sequences that have glycosyl hydrolase domains (GH20, www.cazy.org). Three GH20 genes and corresponding sequences SEQ ID NOS: 1, 3, 5, 12 and 14 were identified from *Terribacillus saccharophilus* and *Terribacillus goriensis* strains. The codon optimized synthetic DNA encoding the mature peptide sequences of the hexosaminidases were ordered from the company Geneart. The mature polypeptides are shown in SEQ ID NO 7, 8, 9 10 and 11.

TABLE 4

| enzyme | Donor |
|---|---|
| SEQ ID NO 7 | *Terribacillus saccharophilus* |
| SEQ ID NO 8 | *Terribacillus goriensis* |
| SEQ ID NO 9 | *Terribacillus saccharophilus* |
| SEQ ID NO 10 | *Terribacillus saccharophilus* |
| SEQ ID NO 11 | *Terribacillus saccharophilus* |

Example 2: Cloning and Expression of the Hexosaminidases

The codon optimized synthetic genes encoding the mature peptide sequences of the hexosaminidases or the polypeptides having hexosaminidase activity is shown in SEQ ID NO 7, 8, 9, 10 and 11. The sequences were inserted into a *Bacillus* expression vector as described in WO 12/025577. Briefly, the DNA encoding the mature peptide of the hexosaminidase gene was cloned in frame to a *Bacillus clausii* secretion signal (BcSP; with the following amino acid sequence: MKKPLGKIVASTALLISVAFSSSIASA (SEQ ID NO 16). BcSP replaced the native secretion signal in the gene. Downstream of the BcSP sequence, an affinity tag sequence was introduced to ease the purification process (His-tag; with the following amino acid sequence: HHHHHHPR (SEQ ID NO 17) The gene that was expressed therefore comprised the BcSP sequence followed by the His-tag sequence followed by the mature wild type GH20 sequence i.e. the polypeptides with SEQ ID NO 7, SEQ ID NO 8, SEQ ID NO 9, SEQ ID NO 10 and SEQ ID NO 11. The final expression plasmid (BcSP-His-tag-GH20) was transformed into a *Bacillus subtilis* expression host. The GH20 BcSP-fusion gene was integrated by homologous recombination into the *Bacillus subtilis* host cell genome upon transformation.

The gene construct was expressed under the control of a triple promoter system (as described in WO 99/43835). The gene coding for chloramphenicol acetyltransferase was used as maker as described in (Diderichsen et al., 1993, *Plasmid* 30: 312-315)). Transformants were selected on LB media agar supplemented with 6 micrograms of chloramphenicol per ml. One recombinant *Bacillus subtilis* clone containing the GH20 expression construct was selected and was cultivated on a rotary shaking table in 500 ml baffled Erlenmeyer flasks each containing 100 ml yeast extract-based media. After 3-5 days' cultivation time at 30° C. to 37° C., the enzyme containing supernatant was harvested by centrifugation and the enzymes was purified by His-tag purification.

Example 3: His Tag Purification Method

The His-tagged GH20 hexosaminidase enzymes were purified by immobilized metal chromatography (IMAC) using $Ni^{2+}$ as the metal ion on 5 mL HisTrap Excel columns (GE Healthcare Life Sciences). The purification took place at pH 7 and the bound proteins were eluted with imidazole. The purity of the purified enzyme was checked by SDS-PAGE and the concentration of the enzyme determined by Absorbance 280 nm after a buffer exchange in 50 mM HEPES, 100 mM NaCl pH7.0

Example 4: Biofilm Assay

*Staphylococcus aureus* was kindly provided by Hugo Lasa (Valle et al., Mol Microbiol. 2003 May; 48 (4):1075-87). The strain was grown on trypticase soy agar (TSA) at 37° C. overnight. Next day, a single colony was transferred to 15 ml trypticase soy broth (TSB) and incubated 5 hours at 37° C. under shaking. The culture was diluted 1:100 in TSB+1% glucose and 100 µL of the bacterial suspension was transferred to each well of a 96-well microtiter plates (Thermo Scientific, Nunclon Delta Surface, cat #167008) and incubated 24 hours at 37° C. without shaking. Supernatant was aspirated and wells were washed with 100 µL of 0.9% sodium chloride and filled with 100 µL of either hard water or 3.3 gr/L Model detergent A containing 0 (control) or 20, 10, 5, 2.5, 1.25, 0.62, 0.31, 0.16, 0.08, 0.04, 0.02 and 0.01 µg/mL of enzyme (the mature polypeptides having SEQ ID NO 7, SEQ ID NO 8, SEQ ID NO 9, SEQ ID NO 10 and SEQ ID NO 11). After incubation at 37° C. for 1 hour, wells were washed with water and stained for 15 min with 100 µL of 0.095% crystal violet solution (SIGMA V5265). Wells were then rinsed twice with 100 µL water, dried and the plates were scanned.

The lowest concentration of each enzyme that could reduce the visible formation of *S. aureus* biofilm after 1 hour incubation, in the presence and absence of detergent was determined (see Table 5). All enzymes were assayed per duplicate with similar results.

TABLE 5

Minimal concentration of enzyme that can reduce the visible formation of *S. aureus* after 1 hour incubation in either hard water or Model detergent A.

| Enzyme | Minimal concentration for biofilm reduction in Model A µg/mL | Minimal concentration for biofilm reduction in Hard water µg/mL |
|---|---|---|
| SEQ ID NO 7 | 2.5 | 0.08 |
| SEQ ID NO 8 | 2.5 | 0.16 |
| SEQ ID NO 9 | 2.5 | 0.16 |
| SEQ ID NO 10 | 0.31 | <0.01 |
| SEQ ID NO 11 | 10 | 0.02 |

Example 5: Deep-Cleaning of Hexosaminidases in Liquid Model Detergent

*Staphylococcus aureus* 15981 (kind gift from Hugo Lasa (Valle et al., Mol Microbiol. 2003 May; 48 (4):1075-87) was used as model microorganism in the present example. *S. aureus* was restreaked on Tryptone Soya Agar (TSA) (pH 7.3) (CM0131; Oxoid Ltd, Basingstoke, UK) and incubated for 1 day at 37° C. A single colony was inoculated into 10 mL of TSB and the culture was incubated for 16 hours at 37° C. with shaking (200 rpm). After propagation, the *S. aureus* culture was diluted (1:100) in fresh TSB+1% glucose (24563; Roquette Freres) and 2 mL aliquots were added to the wells of 12-well polystyrene flat-bottom microplates (3512; Costar, Corning Incorporated, Corning, N.Y., USA), in which round swatches (diameter 2 cm) of sterile polyester (WFK30A) had been placed. Sterile TSB+1% glucose was added to control wells. After 48 h at 37° C. (static incubation), the swatches were rinsed twice with 15° dH water. Five rinsed swatches (sterile or with *S. aureus*) were placed in 50 mL test tubes and 10 mL of wash liquor (15° dH water with 0.2 g/L iron(III) oxide nanopowder (544884; Sigma-Aldrich) with 3.33 g/L liquid model A detergent) and 0.2 ppm enzyme (mature polypeptide with SEQ ID NO 7, 8 and 9) were added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night.

The color difference (L) values were measured using a Handheld Minolta CR-300, and are displayed in table 6. Delta values ($L_{(swatch\ washed\ with\ enzyme)} - L_{(swatch\ washed\ without\ enzyme)}$) are also indicated.

TABLE 6

Deep-cleaning effects of hexosaminidases in model detergent A

| Enzyme | Enzyme concentration (ppm) | L values | ΔT (Lwith enzyme-Lwithout enzyme) |
|---|---|---|---|
| No enzyme | 0 | 102.9 | |
| SEQ ID NO 7 | 0.2 | 115.1 | 12.3 |
| SEQ ID NO 8 | 0.2 | 115.5 | 12.7 |
| SEQ ID NO 9 | 0.2 | 115.2 | 12.3 |

The results show that the hexosaminidases display deep-cleaning properties in model detergent A.

Example 6: Deep-Cleaning Effects of Hexosaminidases in Liquid Model Detergent

*Staphylococcus aureus* biofilms were grown on textile swatches (wfk30A) as described in example 5. Swatches incubated with sterile medium were included as controls. For testing the deep-cleaning properties of the hexosaminidases, five rinsed swatches (sterile or with *S. aureus*) were placed in 50 mL conical centrifuge tubes and 10 mL of wash liquor (15° dH water with 0.2 g/L iron(III) oxide nanopowder (544884; Sigma-Aldrich) with 3.33 g/L liquid model A detergent) and 0.2 ppm (or 2 ppm) enzyme was added to each tube. No enzymes were added to the controls. The test tubes were placed on a Stuart rotator and incubated for 1 hour at 37° C. at 20 rpm. The wash liquor was then removed, and the swatches were rinsed twice with 15° dH water and dried on filter paper over night.

The color difference (L) values were measured using a Handheld Minolta CR-300, and the relative wash efficiencies were calculated (($L_{With\ enzyme} - L_{No\ enzyme}$)/($L_{Sterile\ swatch} - L_{No\ enzyme}$)*100) and are indicated in table 7.

TABLE 7

Percentage wash efficiency in liquid model detergent on *S. aureus* biofilm swatches

| Swatch | Enzyme | Enzyme concentration (ppm) | % Wash efficiency |
|---|---|---|---|
| *S. aureus* biofilm | | 0 | 0.0 |
| *S. aureus* biofilm | SEQ ID NO 9 | 0.2 | 83.7 |
| *S. aureus* biofilm | SEQ ID NO 10 | 0.2 | 82.1 |
| *S. aureus* biofilm | SEQ ID NO 11 | 0.2 | 62.5 |
| *S. aureus* biofilm | SEQ ID NO 11 | 2 | 89.1 |

Combined with the previous examples, the results show that all the polypeptides have deep cleaning properties when compared to samples comprising no enzyme.

Example 7: Deep-Cleaning Effects of Hexosaminidases on *Pseudomonas fluorescens* Biofilm Swatches A *Pseudomonas fluorescens* isolate from Iceland, was used as model microorganism in the present example. *Pseudomonas fluorescens* was restreaked on Tryptone Soya Agar (TSA) (pH 7.3) (CM0131; Oxoid Ltd, Basingstoke, UK) and incubated for 3 days at ambient temperature. A single colony was inoculated into 10 mL of TSB and the culture was incubated for 16 hours at ambient temperature with shaking (Tetramax 1000, 460 rpm). After propagation, the culture was diluted (1:100) in fresh TSB and 1.65 mL aliquots were added to the wells of 12-well polystyrene flat-bottom microplates (3512; Costar, Corning Incorporated, Corning, N.Y., USA), in which round swatches (diameter 2 cm) of sterile textile (WFK20A) had been placed. Sterile TSB was added to control wells. After 48 h incubation at ambient temperature (statically), the swatches were rinsed twice with 0.9% (w/v) NaCl. Five rinsed swatches (sterile or with *P. fluourescens* biofilm) were placed in 50 mL test tubes and 10 mL of wash liquor (15° dH water with 0.2 g/L iron(III) oxide nanopowder (544884; Sigma-Aldrich) with 3.33 g/L liquid model A detergent) and 0.2 ppm or 2 ppm enzyme(s) was added to each tube. Washes without enzyme were included as controls. The test tubes were placed in a Stuart rotator and incubated for 1 hour at 30° C. at 20 rpm. The wash liquor was then removed, and the swatches were rinsed twice with 15° dH water and dried on filter paper over night.

The tristimulus light intensity (Y) values were measured using a DigiEYE colour measurement and imaging system (VeriVide) equipped with a Nikon D90 digital camera, and are displayed in table 8. Delta values ($Y_{(swatches\ washed\ with\ enzyme)} - Y_{(swatches\ washed\ without\ enzyme)}$) are also indicated.

TABLE 8

Deep-cleaning effects of the hexosaminidases on *P. fluorescens* biofilms on textile

| Swatch | Enzyme | Enzyme concentration (ppm) | Average Y values | ΔY |
|---|---|---|---|---|
| *P. fluorescens* biofilm | | 0 | 58.3 | |
| *P. fluorescens* biofilm | SEQ ID NO 7 | 0.2 | 66.1 | 7.8 |
| *P. fluorescens* biofilm | SEQ ID NO 7 | 2 | 66.2 | 7.8 |
| *P. fluorescens* biofilm | SEQ ID NO 8 | 0.2 | 66.7 | 8.4 |
| *P. fluorescens* biofilm | SEQ ID NO 8 | 2 | 66.7 | 8.4 |
| *P. fluorescens* biofilm | SEQ ID NO 9 | 0.2 | 67.0 | 8.6 |
| *P. fluorescens* biofilm | SEQ ID NO 9 | 2 | 67.2 | 8.9 |

TABLE 8-continued

Deep-cleaning effects of the hexosaminidases on
P. fluorescens biofilms on textile

| Swatch | Enzyme | Enzyme concentration (ppm) | Average Y values | ΔY |
|---|---|---|---|---|
| P. fluorescens biofilm | SEQ ID NO 10 | 0.2 | 67.7 | 9.4 |
| P. fluorescens biofilm | SEQ ID NO 10 | 2 | 67.6 | 9.3 |
| P. fluorescens biofilm | SEQ ID NO 11 | 0.2 | 63.0 | 4.6 |
| P. fluorescens biofilm | SEQ ID NO 11 | 2 | 66.9 | 8.6 |

Example 8 Deep-Cleaning Effects of Hexosaminidases in Liquid Model Detergent Against EPS from Different Microorganisms Crude extracts of biofilm extracellular polymeric substances (EPS) were prepared from Staphylococcus aureus 15981 (kind gift from Iñugo Lasa (Valle, J., A. Toledo-Arana, C. Berasain, J. M. Ghigo, B. Amorena, J. R. Penades, and I. Lasa. 2003, Mol. Microbiol. 48:1075-1087), Staphylococcus cohnii (textile isolate, Denmark, 0437F4), Pseudomonas fluorescens (Isolate from Iceland) and Acinetobacter iwoffi (textile isolate from Denmark. For S. aureus, the extract was made as follows: The strain was restreaked on Tryptone Soya Agar (TSA) (pH 7.3) (CM0131; Oxoid Ltd, Basingstoke, UK) and incubated for 3 days at 37° C. 500 mL of TSB+1% glucose (24563; Roquette Freres) was then inoculated, aliquoted into 50 ml conical centrifuge tubes (339652; Thermo Scientific Nunc) (33 ml in each), and incubated for 24 hours at 37° C. with shaking (200 rpm). The cells were subsequently pelleted by centrifugation (10 min, 6000 g, 25° C.), pooled and resuspended in a total of 5 ml 3M NaCl. The suspension was vortexed vigorously and incubated for 15 min at ambient temperature to extract the surface-associated EPS. The cells were then re-pelleted (10 min, 5000 g, 25° C.) and the EPS-containing supernatant was retrieved. The supernatant was sterile filtered twice (0.45 μm followed by 0.2 μm), tested for sterility and stored at −20° C. until further use.

The S. cohnii isolate was restreaked on TSA, incubated for 3 days at 37° C., and used to inoculate an overnight culture (10 ml TSB+1% glucose, incubated at 37° C., 200 rpm). This culture was then diluted (1:100) into 250 ml fresh medium (TSB+1% glucose) in a Corning® CellBIND® 225 cm² Angled Neck Cell Culture Flasks with Vent Cap (Product #3293), and the flask was incubated at 37° C. for 2 days. The biofilm culture was pelleted by centrifugation (10 min, 8000 g, 25° C.), resuspended in 2.5 ml 3M NaCl and incubated for 30 min at room temperature. The cells were then re-pelleted (10 min, 5000 g, 25° C.), and the EPS-containing supernatant was retrieved, sterile filtered (0.20 μm, 16534-K, Minisart, Sartorius Stedim) and stored at −20° C. until use.

P. fluorescens was restreaked on TSA and incubated for 1 day at 20° C. The strain was inoculated into 10 mL of TSB and the culture was incubated statically for 16 hours at 20° C. After propagation, the culture was diluted (1:100) in 400 ml M63 supplemented medium (15 mM $(NH_4)_2SO_4$, 100 mM $KH_2PO_4$, 1.8 μM $FeSO_4$, 1 mM $MgSO_4 \cdot 0.7H_2O$, 0.4% (w/v) glycerol, 0.2% (w/v) Casamino acids and 0.0001% (w/v) Thiamine), added to a Corning® CellBIND® 225 cm² Angled Neck Cell Culture Flasks with Vent Cap and incubated statically for 3 days at 20° C. The biofilm culture was subsequently pelleted by centrifugation (10 min, 8000 g, 25° C.), and the cells resuspended in 4 ml 3M NaCl and incubated for 30 min at 30° C. to extract the surface-associated EPS. The EPS-containing supernatant obtained after centrifugation (10 min, 5000 g, 25° C.) was then sterile filtered and stored at −20° C. until further.

A crude EPS extract from A. iwoffi was prepared as follows: The strain was restreaked on a TSA plate and incubated for 3 days at 30° C. 10 ml LB medium (L3152, Fluka) was then inoculated with a single colony, and incubated at 30° C., 200 rpm for 48h. The culture was diluted (1:100) in 300 ml fresh LB, added to Corning® CellBIND® 225 cm² Angled Neck Cell Culture Flasks with Vent Cap and incubated statically for 4 days at 30° C. The biofilm culture was subsequently pelleted by centrifugation (10 min, 8000 g, 25° C.), and the pellet was resuspended in a total of 3 ml 3M NaCl and incubated for 30 min at room temperature. The EPS-containing supernatant obtained after centrifugation (10 min, 5000 g, 25° C.) was sterile filtered (0.20 μm, 16534-K, Minisart, Sartorius Stedim) and stored at −20° C. until use.

For wash performance testing, 50 ul aliquots of the different crude EPS extracts were spotted on sterile textile swatches (WFK20A) and incubated for 15 min at ambient temperature. The swatches (sterile or with EPS) were placed in 50 mL test tubes and 10 mL of wash liquor (15° dH water with 0.2 g/L iron(III) oxide nano-powder (544884; Sigma-Aldrich) with 3.33 g/L liquid model A detergent) and 0.2 mg/ml or 2 μg/ml enzyme was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night. The tristimulus light intensity (Y) values were measured using a DigiEYE colour measurement and imaging system (VeriVide) equipped with a Nikon D90 digital camera, and are displayed in table 9.

Delta values ($Y_{(swatches\ washed\ with\ enzyme)} - Y_{(swatches\ washed\ without\ enzyme)}$) and relative wash efficiency values ($L_{With\ enzyme} - L_{No\ enzyme}$)/($L_{Sterile\ swatch} - L_{No\ enzyme}$)*100)) are also indicated.

TABLE 9

Deep-cleaning effects of the hexosaminidase shown in SEQ ID NO 9 in liquid model detergent on EPS from different microorganisms

| Origin of EPS | Enzyme concentration (ppm) | Average Y values | ΔY | Wash efficiency (%) |
|---|---|---|---|---|
| Clean textile, no EPS | 0 | 85.4 | | |
| S. aureus | 0 | 41.7 | | |
| S. aureus | 0.2 | 82.7 | 41.1 | 93.8 |
| S. aureus | 2 | 84.3 | 42.6 | 97.4 |
| S. cohnii | 0 | 73.3 | | |
| S. cohnii | 0.2 | 84.6 | 11.3 | 93.0 |
| S. cohnii | 2 | 84.7 | 11.4 | 93.8 |
| P. fluorescens | 0 | 54.4 | | |
| P. fluorescens | 0.2 | 86.0 | 31.6 | 101.8 |
| P. fluorescens | 2 | 85.5 | 31.1 | 100.1 |
| A. lwoffii | 0 | 76.3 | | |
| A. lwoffii | 0.2 | 84.9 | 8.6 | 94.0 |
| A. lwoffii | 2 | 84.7 | 8.4 | 91.8 |

The data clearly shows that the hexosaminidases show deep-cleaning properties against biofilm EPS from various microorganisms, including both gram-positive and gram-negative bacteria.

Example 9: Malodor Reduction of Hexosaminidase in Liquid Model Detergent

EPS were purified as described in e.g. example 8. After purification, 50 μL aliquots of EPS were added to the wells of 12-well polystyrene flat-bottom microplates (3512; Costar, Corning Incorporated, Corning, N.Y., USA), in which round swatches (diameter 2 cm) of sterile polyester (WFK30A) had been placed. The swatches were incubated for 15 min (static incubation) before proceeding Six swatches were placed in 50 mL test tubes and 10 mL of wash liquor (15° dH water with 3.33 g/L liquid model A detergent) and 0.2 ppm, 2.0 ppm or 20.0 ppm enzyme (SEQ ID NO 9) were added to each tube. Washes without enzyme were included as controls. The test tubes were placed in a Stuart rotator and incubated for 1 hour at 37° C. at 20 rpm. The wash liquor was then removed, and the swatches were rinsed twice with 20 mL 15° dH water and dried on filter paper over night. Odor chamber setup and analysis of volatiles on textile using an electronic nose To test for the binding of gaseous volatiles, all dried swatches were randomly distributed in a square plastic box (30.7 cm×21.9 cm×6.0 cm—inside measurements). In a 10 mL glass beaker position in the center, 5 mL of a mixture of various aldehydes (Pentanal 160 mM, Hexanal 40 mM, Heptanal 80 mM, (E)-2-Heptenal 20 mM, Octanal 30 mM, Nonanal 10 mM, Decanal 8 mM, (E)-2-Decenal 10 mM and (E,E)-2-Decadienal 12 mM—all chemical purchased from Sigma-Aldrich) were added. The odor chamber was closed with a lid and wrapped in Parafilm®. The swatches were incubated at room temperature for 16h, before individually being placed in the bottom of 20 mL GC-MS vials (Mikrolab Aarhus A/S, Aarhus, Denmark) and capped with silicone screw top lids (Mikrolab Aarhus A/S, Aarhus, Denmark). From each sample 5 mL headspace was analyzed in a:

Heracles II Electronic nose from Alpha M.O.S., France (double column gas chromatograph with 2 FIDs, column 1: Restek MXT-5 10 m×0.18 mm×0.2 μm and column 2: Restek MXT-1701 10 m×0.18 mm×0.2 μm) after 20 minutes incubation at 40° C. Samples were run in a randomized order.

TABLE 10

Malodor removal by hexosaminidase in Model A model detergent.

| Volatile compound | 0.2 ppm hexosaminidase (SEQ ID NO 9) (Relative intensity) | Without enzyme (Relative intensity) | Odor reduction with 0.2 ppm hexosaminidase (SEQ ID NO 9) Reduction in % |
|---|---|---|---|
| Pentanal | 917323 | 1128853 | 19 |
| Hexanal | 207470 | 280177 | 26 |
| Heptanal | 398361 | 621542 | 33 |
| (E)-2-Heptenal | 59477 | 91362 | 35 |
| Octanal | 103164 | 172130 | 37 |
| Nonanal | 88695 | 130790 | 32 |
| Decanal | 26768 | 44650 | 40 |
| (E)-2-Decenal | 18097 | 36608 | 51 |
| (E,E)-2-Decadienal | 49063 | 101721 | 52 |

The results show that hexosaminidase display malodor reduction properties in model detergent A.

Example 10: Deep-Cleaning of Hexosaminidases in Different Detergents

A crude EPS (extracellular polymeric substances) extract was prepared from *Pseudomonas fluorescens* (Isolate from Iceland) as described in example 8. For wash performance testing, 50 ul aliquots of this extract were spotted on sterile textile swatches (WFK20A) and left to soak for 15 min at ambient temperature. The swatches (sterile or with EPS) were placed in 50 mL conical centrifuge tubes and 10 mL of wash liquor (15° dH water with 0.2 g/L iron(III) oxide nano-powder (544884; Sigma-Aldrich) and with detergent (3.33 g/L liquid model A detergent, 2.0 g/L model N or 4.6 g/L Persil Universal Gel®) was added. The enzyme was added to a final concentration of 0.2 μg/ml. Tubes without enzymes were included as controls. The test tubes were placed in a Stuart rotator and incubated for 1 hour at 37° C. at 20 rpm. The wash liquor was then removed, and the swatches were rinsed twice with 15° dH water and dried on filter paper over night. The tristimulus light intensity (Y) values were measured using a DigiEYE colour measurement and imaging system (VeriVide) equipped with a Nikon D90 digital camera, and are displayed in table 11.

Delta values ($Y_{(swatch\ washed\ with\ enzyme)} - Y_{(swatch\ washed\ without\ enzyme)}$) are also indicated.

TABLE 11

Deep-cleaning of hexosaminidases in different detergents on *P.fluorescens* EPS swatches

| Swatch | Enzyme | Enzyme conc. (ppm) | Model A Y values | ΔY | Model N Y values | ΔY | Persil Universal Gel (commercial detergent) Y values | ΔY |
|---|---|---|---|---|---|---|---|---|
| No EPS | — | 0 | 85.6 | | 61.7 | | 84.4 | |
| EPS | — | 0 | 49.7 | | 51.9 | | 55.2 | |
| EPS | Seq ID NO. 7 | 0.2 | 85.1 | 35.5 | 74.1 | 22.2 | 82.8 | 27.6 |
| EPS | Seq ID NO. 8 | 0.2 | 83.5 | 33.8 | 75.3 | 23.4 | 83.5 | 28.3 |
| EPS | Seq ID NO. 9 | 0.2 | 85.0 | 35.3 | 73.4 | 21.5 | 81.8 | 26.5 |
| EPS | Seq ID NO. 10 | 0.2 | 86.0 | 36.3 | 74.8 | 22.9 | 84.7 | 29.5 |
| EPS | Seq ID NO. 11 | 0.2 | 81.5 | 31.8 | 72.4 | 20.5 | 77.5 | 22.2 |

Example 11: Wash Performance in TOM

A crude EPS extract was prepared from *Pseudomonas fluorescens* (Isolate from Iceland,) as described in example 8. The extract was sterile filtered prior to use, and 100)E1 aliquots were spotted on textile swatches (wfk20A (Polyester/Cotton mix (65%/35%)), 50 mm×50 mm), and incubated at room temperature for 10 min. The Terg-o-tometer wash was performed at follows; 0.4 g/L iron(III) oxide nano-powder (544884; Sigma-Aldrich) and 3.33 g/L liquid model detergent A was weighed out and left to soak for 1 h prior to the wash. The dirty detergent was then added to 1000 ml pre-warmed water hardness (15° dH) in the TOM beakers, and allowed to dissolve for 10 min (maximum agitation). The agitation level was then reduced to 90 rpm, and the textile swatches (two EPS swatches as well as ballast material (wfk10A, wfk30A) to reach a total of 10 g textile/beaker) were added and washed with or without enzyme (0.2 ppm) for 35 min at 30° C. After wash, all swatches were rinsed twice in tap water and dried on filter paper over night.

The remisssion (REM$^{460\ nm}$) values were measured using a Macbeth Color-Eye 7000 (CE7000), and are displayed in table 12.

Delta values (REM$^{460\ nm}_{(swatches\ washed\ with\ enzyme)}$−REM$^{460\ nm}_{(swatches\ washed\ without\ enzyme)}$) are also indicated.

TABLE 12

Deep-cleaning properties of hexosamidases on EPS swatches, washed in TOM

| Swatch | Enzyme | Enzyme concentration (ppm) | Average Remission (460 nm) values | ΔRem(460 nm) |
|---|---|---|---|---|
| Clean textile, no EPS | | | 60.4 | |
| P. fluorescens EPS | SEQ ID NO 9 | 0 | 47.1 | |
| P. fluorescens EPS | SEQ ID NO 9 | 0.2 | 65.3 | 18.2 |

Example 12: Wash Performance in Full-Scale Wash

A crude EPS extract was prepared from *Pseudomonas fluorescens* (Isolate from Iceland) as described in example 8. The extract was spotted (200 µl aliquots) on a prewashed T-shirt (Anvil sustainable t-shirt (50% polyester/50% cotton)) that had been cut down the middle, and the spots were left to dry at room temperature for 30 min prior to the wash. The two halves of the T-shirt were washed independently in a Miele Laundry Washing Machine (Miele Softtronic, W2245) using tap water and 0.16 g/L iron(III) oxide nanopowder (544884; Sigma-Aldrich) in 3.33 g/L liquid model A detergent. The 40° C. Color program was used (run time 1 h, 26 min). After wash, the two halves of the T-shirt were hang-dried at room temperature overnight. The remisssion (REM$^{460\ nm}$) values were measured using a Macbeth Color-Eye 7000 (CE7000), and are displayed in table 13. Delta values (REM$^{446\ nm}_{(swatches\ washed\ with\ enzyme)}$−REM$^{460\ nm}_{(swatches\ washed\ without\ enzyme)}$) are also indicated.

TABLE 13

Deep-cleaning of hexosaminidases in full-scale washing machine

| EPS spotted on T-shirt | Enzyme | Enzyme concentration (ppm) | Average Rem$^{460nm}$ values | ΔRem$^{460nm}$ |
|---|---|---|---|---|
| P. fluorescens EPS | SEQ ID NO 9 | 0 | 22.4 | |
| P. fluorescens EPS | SEQ ID NO 9 | 0.2 | 45.7 | 23.3 |

Example 13: EPS Hydrolysis Measurements Using Fluorescent WGA-Alexafluor488 Assay The *Pseudomonas fluorescens* strain isolated from Iceland was used as model microorganisms in the present example. The *Pseudomonas fluorescens* strain was restreaked on Tryptone Soya Agar (TSA) (pH 7.3) (CM0131; Oxoid Ltd, Basingstoke, UK) and incubated for 1 day at 23° C. The strain was inoculated into 10 mL of TSB and the culture was incubated with shaking for 16 hours at 23° C. The overnight culture was diluted (1:100) in 200 ml M63 supplemented medium (15 mM (NH4)2SO4, 100 mM KH2PO4, 1.8 µM FeSO4, 1 mM MgSO4.7H20, 0.4% (w/v) glycerol, 0.2% (w/v) Casamino acids and 0.0001% (w/v) Thiamine) added to a Corning® CellBIND® 225 cm² Angled Neck Cell Culture Flask with Vent Cap (Product #3293) and incubated statically for 5 days at 23° C. Each biofilm culture was subsequently transferred to four 50 ml falcon tubes (Corning #430820) and pelleted by centrifugation (10 min, 8000 g, 25° C.), and the supernatants were discarded completely. The residual pellets from each of the four falcons were resuspended in 0.450 ml 3M NaCl to extract the surface-associated EPS (extracellular polymeric substances) and pooled in one test tube (5 ml, Eppendorf #0030119401). The suspension was centrifuged at 5000 g for 10 min at 25° C. and the 1.8 ml supernatant was transferred to a new test tube as EPS fraction and stored at −20° C. until further use (termed crude EPS). 150 ul aliquots of the crude EPS were dispensed in three Eppendorf tubes and mixed with 150 ul of an enzyme solution containing 80 ppm of either SEQ ID NO 9 or 50 mM Hepes100 mM NaCl buffer alone and incubated 1 hr at room temperature. 50 ul aliquot samples were retrieved from each tube and then added to the wells of a nunc Maxisorp black microtiter plate (Thermo Scientific #437111) in which round swatches of sterile prewashed swatches (wfk 20A, polyester/cotton 65%/35%) had been placed. The plate was incubated at room temperature for 15 minutes. Supernatants were then removed from each well and swatches were washed with 100 ul water. Next, 50 ul of WGA-Alexa fluor488 dye (10 ug/ml; excitation/emission maxima 495/519 nm; Thermo Fischer Scientific, #W11261) was added to each well. Alexa Fluor® 488 WGA binds to sialic acid and N-acetylglucosaminyl residues. The plate was incubated at room temperature for 15 min. Samples were finally washed with 100 ul water and measured in the SpectraMax M3 instrument. Each of the three samples corresponding to the crude EPS mixed with the enzyme solutions and buffer control, were tested on 8 swatches placed in 8 wells. The measurements obtained including the standard deviations are listed below in table 14.

TABLE 14

Fluorescent measurements with WGA-Alexa Fluor488 dye of crude EPS from P. fluorescens strain treated with either buffer or SEQ ID NO 9.

| sample | average measurement |
|---|---|
| Buffer control | 416 |
| SEQ ID NO 9 | 121 |

Results from the fluorescent measurements show that the EPS extract from the *P. fluorescens* strain is labelled with WGA-Alexa Fluor488 suggesting that the EPS contains N-acetylglucosaminyl residues and is sensitive to hexosaminidase (SEQ ID NO 9) hydrolysis.

Example 14: Wheat-Germ Agglutinin (WGA)-Staining of Washed EPS Swatches

A crude EPS extract was prepared from *Staphylococcus aureus* 15981 (kind gift from Iñigo Lasa (Valle, J., A. Toledo-Arana, C. Berasain, J. M. Ghigo, B. Amorena, J. R. Penades, and I. Lasa. 2003, Mol. Microbiol. 48:1075-1087) as described in example 8 with minor modifications: The culture was incubated for 24 h at 37° C. in TSB+1% glucose prior to EPS extraction. For washing, 100 ul aliquots of the EPS were spotted on sterile textile swatches (prewashed wfk20A textile, 65% Polyester/35% Cotton) and incubated for 20 min at ambient temperature. The swatches (sterile or with EPS) were placed in 50 mL test tubes and 10 mL of wash liquor (15° dH water with 3.33 g/L liquid model A detergent) and 20 µg/ml enzyme was added to each tube.

Washes without enzyme were included as controls. The test tubes were placed in a Stuart rotator and incubated for 1 hour at 37° C. at 20 rpm. The wash liquor was then removed, and the swatches were rinsed twice with 15° dH water and placed in a 12-well polystyrene flat-bottom microplate (3512; Costar, Corning Incorporated, Corning, N.Y., USA). The swatches were then stained with Alexa Fluor® 488 Conjugated Wheat Germ Agglutinin (WGA) (10 µg/ml in 1×PBS) for 30 min at room temperature, rinsed twice with 1×PBS and measured by well-scanning in a BMG CLAR-IOstar microplate reader (Excitation at 488 nm, emission at 525 nm). The fluorescence intensity values are shown in table 15.

The relative substrate removal compared to the control ($FIU_{with\ enzyme}$–$FIU_{without\ enzyme}$) is also shown.

TABLE 15

Wheat-germ agglutinin (WGA)-staining of EPS swatches washed with or without hexosaminidase (SEQ ID NO 9).

| Swatch | Enzyme concentration (ppm) | Fluorescent signal intensity (488 nm(Ex), 525 nm(Em), background subtracted) | % remaining substrate |
|---|---|---|---|
| S. aureus EPS | 0 | 49082 | 100 |
| S. aureus EPS | 20 | 3258 | 6.6 |

When WGA lectin has affinity for N-acetylglucosaminyl residues, the results shows that the hexosaminidase treatment improves substrate removal from the textile during the wash.

Example 15: Construction of Clades and Phylogenetic Trees

The Glyco_hydro_20 domain includes the polypeptides having hexosaminidase e.g. PNAG activity and comprises the WND domain as well as the clusters such as the clades.
A phylogenetic tree was constructed, of polypeptide sequences containing a Glyco_hydro_20 domain, as defined in PFAM (PF00728, Pfam version 31.0 Finn (2016). Nucleic Acids Research, Database Issue 44:D279-D285).

The phylogenetic tree was constructed from a multiple alignment of mature polypeptide sequences containing at least one Glyco_hydro_20 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128). The polypeptide sequences containing a Glyco_hydro_20 domain comprises several motifs; one example is GXDE (SEQ ID NO 18), situated in positions 158 to 161 in *Terribacillus saccharophilus* (SEQ ID NO 9). Residues D and E are the key catalytic residues of Glyco_hydro_20 enzymes (position 160 to 161 in SEQ ID NO 9).

Figure 3:
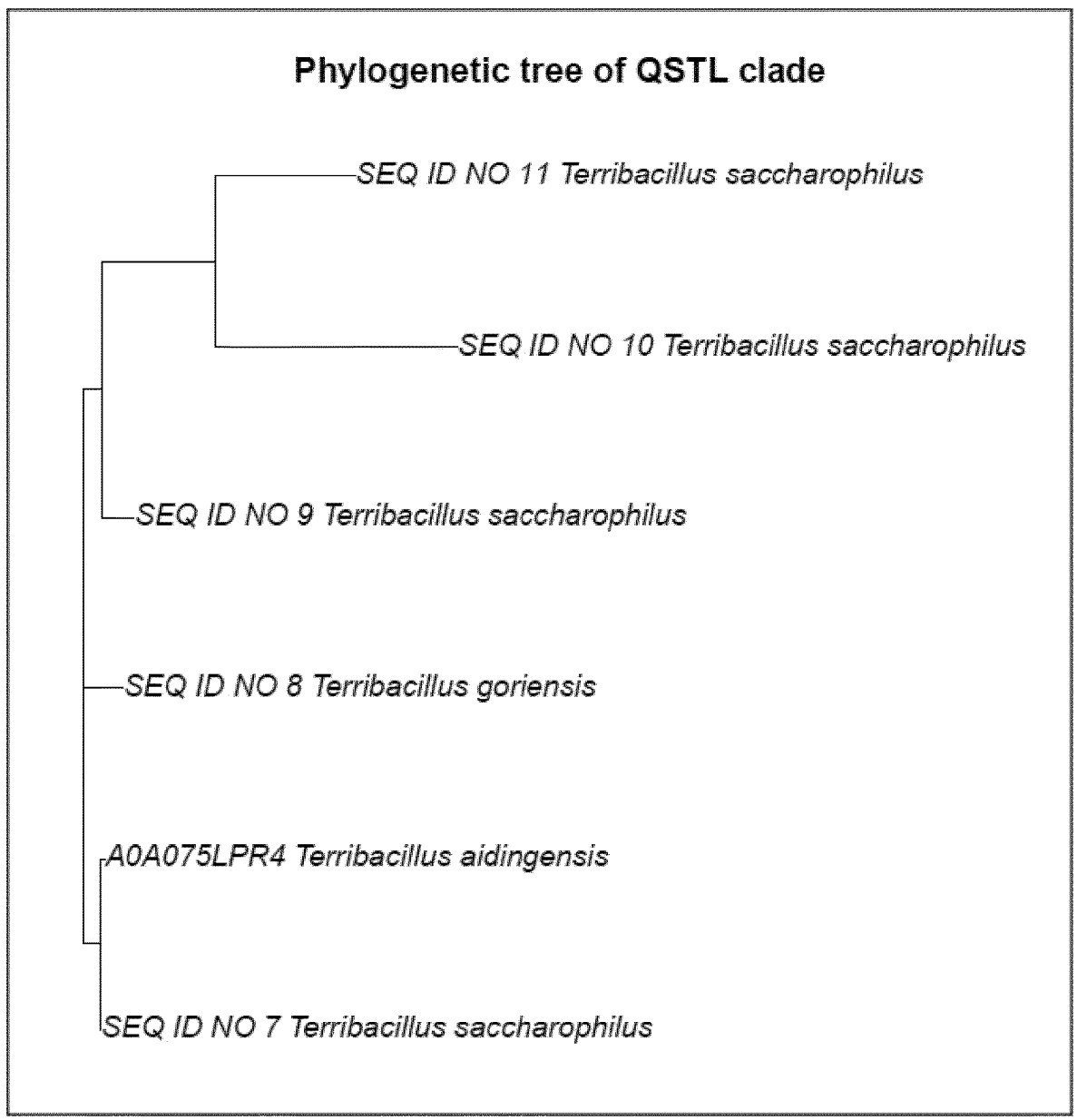

The polypeptides in Glyco_hydro_20 can be separated into multiple distinct sub-clusters, or clades as listed below. The distinct motifs for each clade are described in details below.
Generation of IAS Domain
A domain, shared by the polypeptides, was identified. This domain has not been described previously. The domain is termed IES and polypeptides of this domain comprises Glyco_hydro_20 domain polypeptides of bacterial origin and are in addition to having PNAG activity, characterized by comprising certain motifs. The polypeptides of the domain comprise the motif example [EQ][NRSHA][YVFL] [AGSTC][IVLF][EAQYN][SN] (SEQ ID NO 19), corresponding to ESYAIAS at position 44 to 50 of SEQ ID NO 9.
Generation of WND Domain
A domain, shared by the polypeptides, was identified. This domain has not been described previously. The domain is termed WND and polypeptides of this domain comprise Glyco_hydro_20 domain polypeptides of bacterial origin and are in addition to having PNAG activity, characterized by comprising certain motifs. The polypeptides of the domain comprise the motif example [VIM][LIV]G[GAV] DE[VI][PSA] (SEQ ID NO 20), corresponding to pos 156 to 163 of SEQ ID NO 9, where G and DE (corresponding to positions 158 and 160-161 of SEQ ID NO 9) are fully conserved in DSP3 clade and part of the active site. Residues D and E are the key catalytic residues of Glyco_hydro_20 enzymes (position 160 to 161 in SEQ ID NO 9). Another motif which may be comprised by the polypeptides of the WND domain is WND[SQR][IVL][TLVM] (SEQ ID NO 21), 193 to 198 in SEQ ID NO 9, where W (pos 193 in SEQ ID NO 9) is part of the active site pocket and putatively involved in binding of the N-acetyl group of the PNAG substrate.
Generation of QSTL Clade
The QSTL clade comprises WND domain polypeptides of bacterial origin, having hexosaminidase e.g. PNAG activity. The polypeptides of the clade comprise the motif example QSTL (SEQ ID NO 22), corresponding to pos 216 to 219 of SEQ ID NO 9, where all four amino are fully conserved in QSTL clade. The motif is part of a putative "lid" of the enzymes' TIM barrel structure and putatively involved in substrate binding. Another motif which may be comprised by the polypeptides of the QSTL clade is NKFFY (SEQ ID NO 23), 273 to 277 in SEQ ID NO 9. A further motif which may be comprised by the polypeptides of the QSTL clade is NLD[DR]S (SEQ ID NO 24), corresponding to amino acids 204 to 208 in SEQ ID NO 9.
An alignment of the polypeptides is shown in FIG. 2. A phylogenetic tree of the polypeptides is shown in FIG. 3.

Example 16: Graying Test with Different Detergents

The liquid detergent (Persil Universal Gel 2017 formulation, Henkel) was used in a concentration of 0.5 wt.-% in deionized water. The enzyme used had the amino acid sequence of SEQ ID NO:10 and was added in a concentration of 0.5 mg/L. Different textiles, including cotton, as well as textiles soiled with bacterial biofilms were washed with the prepared wash liquour in a Launder O Meter (LOM). for 30 min at 30° C. By spectral photometry the whiteness and graying, respectively, were determined as the difference (y value) between a reference example without the enzyme vs. examples with the enzyme after 1, 2, 3 and 4 washes. The results were as followed (higher values indicate less graying)

| 1. wash | 2. wash | 3. wash | 4. wash |
|---|---|---|---|
| 2.3 | 4.6 | 3.5 | 4.7 |

The same experiment was repeated with other liquid detergents (Persil Power Mix Caps; Spee Gel and Dixan, all of Henkel)

The results were as follows:

Persil Power Mix Caps

| 1. wash | 2. wash | 3. wash | 4. wash |
|---------|---------|---------|---------|
| 3.9     | 3.1     | 3.1     | 4.8     |

Spee Gel

| 1. wash | 2. wash | 3. wash | 4. wash |
|---------|---------|---------|---------|
| 3.6     | 5.3     | 4.9     | 3.0     |

Dixan

| 1. wash | 2. wash | 3. wash | 4. wash |
|---------|---------|---------|---------|
| 2.8     | 3.4     | 3.8     | 4.5     |

The tested enzyme showed significant improvement with respect to graying of the textiles in all detergent matrices tested.

Joint Research Agreement

The material in the present disclosure was conceived and developed under a joint research agreement by Henkel AG & Co. KGaA and Novozymes A/S as executed on 12 Oct. 2012. Ownership between the parties is governed per the terms of said agreement and reflected in the assignment records held by the relevant records holder.

The invention claimed is:

1. A cleaning composition comprising:
one or more polypeptide variants having hexosaminidase activity, wherein the one or more polypeptide variants having hexosaminidase activity have at least 90% sequence identity to the polypeptide of SEQ ID NO: 10; and,
wherein the amount of the one or more polypeptide variants ranges from 0.00004 ppm to 100 ppm in the cleaning composition.

2. The composition according to claim 1 wherein the polypeptide variant has N-acetylglucosaminidase activity and/or β-N-acetylglucosamininidase activity.

3. The composition according to claim 1, wherein the polypeptide variant further comprises one or more of the motifs GXDE (SEQ ID NO: 18), [EQ][NRSHA][YVFL][AGSTC][IVLF][EAQYN][SN] (SEQ ID NO: 19), [VIM][LIV]G [GAV]DE [VI][PSA] (SEQ ID NO: 20), WND[SQR][IVL][TLVM] (SEQ ID NO: 21), QSTL (SEQ ID NO: 22), NKFFY (SEQ ID NO: 23), or NLD[DR]S (SEQ ID NO: 24).

4. The composition according to claim 1, wherein the polypeptide variant has at least 99% sequence identity to the protein of SEQ ID NO: 10.

5. The composition of claim 1, wherein the polypeptide variant comprises or consists of SEQ ID NO: 10.

6. The composition according to claim 1, wherein the composition is a laundry or dishwashing composition.

7. The composition according to claim 1, further comprising up to 50 wt % of one or more surfactants, wherein the one or more surfactants are anionic and/or nonionic.

8. The cleaning composition of claim 1, wherein the cleaning composition is selected from the group comprising a solid laundry detergent composition, a liquid laundry detergent composition, a fabric finisher, an acidic cleaning agent, a neutral cleaning agent, an alkaline cleaning agent, a hand dishwashing agent, and an automatic dishwashing composition.

9. The cleaning composition of claim 1, further comprising at least one zeolite builder, at least one phosphonate builder, at least one further enzyme, at least one polymer, at least one silicate builder, carboxymethylcellulose, at least one soil release polymer, at least one bleaching system, at least one surfactant, at least one organic solvent, at least one bittering agent, at least one optical brightener, at least one softening silicone, at least one perfume, polyquaternium 10, polyquaternium 37, a plant-based esterquat, an adipic acid, at least one acidic biocide, at least one sulfopolymer, a probiotic, a spore, or combinations thereof.

10. The cleaning composition of claim 1, wherein the composition is in unit dose form.

11. The cleaning composition of claim 1, wherein the composition is a phosphate-free composition.

\* \* \* \* \*

SEQUENCE LISTING

```
<160> NUMBER OF SEQ ID NOS: 24

<210> SEQ ID NO 1
<211> LENGTH: 1095
<212> TYPE: DNA
<213> ORGANISM: Terribacillus saccharophilus
<220> FEATURE:
<221> NAME/KEY: sig_peptide
<222> LOCATION: (1)..(123)
<220> FEATURE:
<221> NAME/KEY: CDS
<222> LOCATION: (1)..(1095)
<220> FEATURE:
<221> NAME/KEY: mat_peptide
<222> LOCATION: (124)..(1095)

<400> SEQUENCE: 1 atg gta tct cgc acg atg ctt ttc atc aag cgc gag aag ggc aag acg         48
Met Val Ser Arg Thr Met Leu Phe Ile Lys Arg Glu Lys Gly Lys Thr
    -40                 -35                 -30 gtt ctt atc aag ttc ctt tct atc acg aca gta tct atc ctt ctt ttc         96
Val Leu Ile Lys Phe Leu Ser Ile Thr Thr Val Ser Ile Leu Leu Phe
-25                 -20                 -15                 -10 ctt acg atg gcg aac act gcg caa gcg caa gac caa gag aag ggc atc        144
Leu Thr Met Ala Asn Thr Ala Gln Ala Gln Asp Gln Glu Lys Gly Ile
                 -5                  -1   1               5 aca atc gac atc tct cgc aag tac tac agc atc aag acg ctt aag gcg        192
Thr Ile Asp Ile Ser Arg Lys Tyr Tyr Ser Ile Lys Thr Leu Lys Ala
        10                  15                  20 atc gtt gac gag atc tca gcg aat ggt ggc gac tac ctt caa ctt cac        240
Ile Val Asp Glu Ile Ser Ala Asn Gly Gly Asp Tyr Leu Gln Leu His
    25                  30                  35 ttc tct gac aac gag agc tac gcg atc gcg tct gag ttc ctt ggc caa        288
Phe Ser Asp Asn Glu Ser Tyr Ala Ile Ala Ser Glu Phe Leu Gly Gln
40                  45                  50                  55 aac tct gag aac cca aac tct gcg tac ctt aca aag aag gag ctt ctt        336
Asn Ser Glu Asn Pro Asn Ser Ala Tyr Leu Thr Lys Lys Glu Leu Leu
                60                  65                  70 tca ctt atc gcg tac tct aac gac cgc aac atc atg gtt atc ccg gac        384
Ser Leu Ile Ala Tyr Ser Asn Asp Arg Asn Ile Met Val Ile Pro Asp
            75                  80                  85 atc gac ctt cct gcg cac tca aag ggc tgg ctt aac atc atg aag gag        432
Ile Asp Leu Pro Ala His Ser Lys Gly Trp Leu Asn Ile Met Lys Glu
        90                  95                  100
```

-continued

| | |
|---|---|
| aag gac tct ggc ctt tac aca gac atc gta act gac tac tca gaa gac<br>Lys Asp Ser Gly Leu Tyr Thr Asp Ile Val Thr Asp Tyr Ser Glu Asp<br>105                     110                     115 | 480 |
| act ctt gac tac cac aac aac gcg gtt gcg ctt tac acg gcg aac caa<br>Thr Leu Asp Tyr His Asn Asn Ala Val Ala Leu Tyr Thr Ala Asn Gln<br>120                     125                   130                     135 | 528 |
| ctt ctt gac gag gtt ctt gac ctt ttc tac caa cct aag ttt gct ggc<br>Leu Leu Asp Glu Val Leu Asp Leu Phe Tyr Gln Pro Lys Phe Ala Gly<br>              140                     145                     150 | 576 |
| aag caa cgc atc gtt ctt ggt ggc gac gag gtt cct ggc tct ggt gcg<br>Lys Gln Arg Ile Val Leu Gly Gly Asp Glu Val Pro Gly Ser Gly Ala<br>                     155                     160                     165 | 624 |
| cac caa act gac ttc atc cgc ttc atg aac cag atc gcg aag aca gcg<br>His Gln Thr Asp Phe Ile Arg Phe Met Asn Gln Ile Ala Lys Thr Ala<br>170                     175                     180 | 672 |
| aag gcg tct aac tac gag cca caa atg tgg aac gac agc atc act cct<br>Lys Ala Ser Asn Tyr Glu Pro Gln Met Trp Asn Asp Ser Ile Thr Pro<br>185                     190                     195 | 720 |
| gag ggc atc caa aac ctt gac cgc tct ttc tct atc ctt tac tgg aag<br>Glu Gly Ile Gln Asn Leu Asp Arg Ser Phe Ser Ile Leu Tyr Trp Lys<br>200                     205                     210                     215 | 768 |
| caa tca acg ctt tca aat ggt gcg caa tct ctt gac gta caa gac ttc<br>Gln Ser Thr Leu Ser Asn Gly Ala Gln Ser Leu Asp Val Gln Asp Phe<br>                     220                     225                     230 | 816 |
| gag gag aac ggc ctt tca gtt tac aac tac aac gct tac agc ctt tac<br>Glu Glu Asn Gly Leu Ser Val Tyr Asn Tyr Asn Ala Tyr Ser Leu Tyr<br>                     235                     240                     245 | 864 |
| ttc ctt cct agc act cgc ttc acg caa gag gac atc acg gag caa atc<br>Phe Leu Pro Ser Thr Arg Phe Thr Gln Glu Asp Ile Thr Glu Gln Ile<br>250                     255                     260 | 912 |
| gac tac atg aag tgg gcg tat gcg tac aac aag ttc ttc tac atc tct<br>Asp Tyr Met Lys Trp Ala Tyr Ala Tyr Asn Lys Phe Phe Tyr Ile Ser<br>265                     270                     275 | 960 |
| gac tac tac aag caa gta gac aca cca aac gta aag ggc tca tct ctt<br>Asp Tyr Tyr Lys Gln Val Asp Thr Pro Asn Val Lys Gly Ser Ser Leu<br>280                     285                     290                     295 | 1008 |
| gta ttc tgg ggt gag cac gcg aac gac ctt tct caa gag ggc ctt ctt<br>Val Phe Trp Gly Glu His Ala Asn Asp Leu Ser Gln Glu Gly Leu Leu<br>                     300                     305                     310 | 1056 |
| aag caa gag aag cca ctt atc caa aac ttc ctt ggc ctt<br>Lys Gln Glu Lys Pro Leu Ile Gln Asn Phe Leu Gly Leu<br>315                     320 | 1095 |

<210> SEQ ID NO 2
<211> LENGTH: 365
<212> TYPE: PRT
<213> ORGANISM: Terribacillus saccharophilus

<400> SEQUENCE: 2

Met Val Ser Arg Thr Met Leu Phe Ile Lys Arg Glu Lys Gly Lys Thr
          -40                  -35                  -30

Val Leu Ile Lys Phe Leu Ser Ile Thr Thr Val Ser Ile Leu Leu Phe
-25                    -20                  -15                  -10

Leu Thr Met Ala Asn Thr Ala Gln Ala Gln Asp Gln Glu Lys Gly Ile
              -5                     -1  1                  5

Thr Ile Asp Ile Ser Arg Lys Tyr Tyr Ser Ile Lys Thr Leu Lys Ala
          10                  15                  20

Ile Val Asp Glu Ile Ser Ala Asn Gly Gly Asp Tyr Leu Gln Leu His
     25                  30                  35

-continued

```
Phe Ser Asp Asn Glu Ser Tyr Ala Ile Ala Ser Glu Phe Leu Gly Gln
 40                  45                  50                  55
Asn Ser Glu Asn Pro Asn Ser Ala Tyr Leu Thr Lys Lys Glu Leu Leu
                 60                  65                  70
Ser Leu Ile Ala Tyr Ser Asn Asp Arg Asn Ile Met Val Ile Pro Asp
             75                  80                  85
Ile Asp Leu Pro Ala His Ser Lys Gly Trp Leu Asn Ile Met Lys Glu
         90                  95                 100
Lys Asp Ser Gly Leu Tyr Thr Asp Ile Val Thr Asp Tyr Ser Glu Asp
    105                 110                 115
Thr Leu Asp Tyr His Asn Asn Ala Val Ala Leu Tyr Thr Ala Asn Gln
120                 125                 130                 135
Leu Leu Asp Glu Val Leu Asp Leu Phe Tyr Gln Pro Lys Phe Ala Gly
                140                 145                 150
Lys Gln Arg Ile Val Leu Gly Gly Asp Glu Val Pro Gly Ser Gly Ala
            155                 160                 165
His Gln Thr Asp Phe Ile Arg Phe Met Asn Gln Ile Ala Lys Thr Ala
        170                 175                 180
Lys Ala Ser Asn Tyr Glu Pro Gln Met Trp Asn Asp Ser Ile Thr Pro
    185                 190                 195
Glu Gly Ile Gln Asn Leu Asp Arg Ser Phe Ser Ile Leu Tyr Trp Lys
200                 205                 210                 215
Gln Ser Thr Leu Ser Asn Gly Ala Gln Ser Leu Asp Val Gln Asp Phe
                220                 225                 230
Glu Glu Asn Gly Leu Ser Val Tyr Asn Tyr Asn Ala Tyr Ser Leu Tyr
            235                 240                 245
Phe Leu Pro Ser Thr Arg Phe Thr Gln Glu Asp Ile Thr Glu Gln Ile
        250                 255                 260
Asp Tyr Met Lys Trp Ala Tyr Ala Tyr Asn Lys Phe Phe Tyr Ile Ser
    265                 270                 275
Asp Tyr Tyr Lys Gln Val Asp Thr Pro Asn Val Lys Gly Ser Ser Leu
280                 285                 290                 295
Val Phe Trp Gly Glu His Ala Asn Asp Leu Ser Gln Glu Gly Leu Leu
                300                 305                 310
Lys Gln Glu Lys Pro Leu Ile Gln Asn Phe Leu Gly Leu
            315                 320
```

<210> SEQ ID NO 3
<211> LENGTH: 1047
<212> TYPE: DNA
<213> ORGANISM: Terribacillus goriensis
<220> FEATURE:
<221> NAME/KEY: sig_peptide
<222> LOCATION: (1)..(75)
<220> FEATURE:
<221> NAME/KEY: CDS
<222> LOCATION: (1)..(1047)
<220> FEATURE:
<221> NAME/KEY: mat_peptide
<222> LOCATION: (76)..(1047)

<400> SEQUENCE: 3

```
atg ctt atc aag ttc ctt tct atc acg aca gtt tca atc ctt ctt ttc      48
Met Leu Ile Lys Phe Leu Ser Ile Thr Thr Val Ser Ile Leu Leu Phe
-25                 -20                 -15                 -10 ctt acg atg tct aac act gcg caa gcg caa gac caa gag aag ggc atc      96
Leu Thr Met Ser Asn Thr Ala Gln Ala Gln Asp Gln Glu Lys Gly Ile
                 -5              -1   1                   5
```

| | | |
|---|---|---|
| aca atc gac atc tct cgc aag tac tac tct atc gag aca ctt aag tct<br>Thr Ile Asp Ile Ser Arg Lys Tyr Tyr Ser Ile Glu Thr Leu Lys Ser<br>         10                       15                    20 | | 144 |
| atc atc gac gag atc tca gcg aat ggt ggc gac tac ctt caa ctt cat<br>Ile Ile Asp Glu Ile Ser Ala Asn Gly Gly Asp Tyr Leu Gln Leu His<br> 25                   30                        35 | | 192 |
| ttc tct gac aac gag cgc tac gcg atc gcg tca gag ttc ctt ggc caa<br>Phe Ser Asp Asn Glu Arg Tyr Ala Ile Ala Ser Glu Phe Leu Gly Gln<br>40                  45                    50                55 | | 240 |
| aac ggc gag aac cca aac tct act tac ctt aca aag aag gag ctt ctt<br>Asn Gly Glu Asn Pro Asn Ser Thr Tyr Leu Thr Lys Lys Glu Leu Leu<br>                 60                      65                    70 | | 288 |
| tct ctt atc gcg tac tct aac gac cgc gac atc atg gta atc cca gac<br>Ser Leu Ile Ala Tyr Ser Asn Asp Arg Asp Ile Met Val Ile Pro Asp<br>              75                    80                    85 | | 336 |
| atc gac ctt cca gcg cat tct cgt ggc tgg ctt aac atc atg aag gag<br>Ile Asp Leu Pro Ala His Ser Arg Gly Trp Leu Asn Ile Met Lys Glu<br>         90                      95                  100 | | 384 |
| aag gac tca ggc ctt tac act gac atc gta acg gac tac tct gag gac<br>Lys Asp Ser Gly Leu Tyr Thr Asp Ile Val Thr Asp Tyr Ser Glu Asp<br>105                   110                    115 | | 432 |
| aca ctt gac tac cat aac aac gct gta gcg ctt tac aca gca aac caa<br>Thr Leu Asp Tyr His Asn Asn Ala Val Ala Leu Tyr Thr Ala Asn Gln<br>120                   125                    130                135 | | 480 |
| ctt ctt gac gag gta ctt gac ctt ttc tac caa ccg aag ttt gct ggc<br>Leu Leu Asp Glu Val Leu Asp Leu Phe Tyr Gln Pro Lys Phe Ala Gly<br>                 140                    145                    150 | | 528 |
| aag cag cgc atc gta ctt ggt ggc gac gag gtt cct ggc tct ggc gta<br>Lys Gln Arg Ile Val Leu Gly Gly Asp Glu Val Pro Gly Ser Gly Val<br>             155                    160                    165 | | 576 |
| cac cag act gac ttc atc cgc ttc atg aac caa atc gcg gag act gcg<br>His Gln Thr Asp Phe Ile Arg Phe Met Asn Gln Ile Ala Glu Thr Ala<br>                 170                    175                    180 | | 624 |
| aag gct tct aac tac aag cca caa atg tgg aac gac tct atc aca cct<br>Lys Ala Ser Asn Tyr Lys Pro Gln Met Trp Asn Asp Ser Ile Thr Pro<br>185                   190                    195 | | 672 |
| gag ggc atc caa aac ctt gac cgc tca ttc tct atc ctt tac tgg aag<br>Glu Gly Ile Gln Asn Leu Asp Arg Ser Phe Ser Ile Leu Tyr Trp Lys<br>200                   205                    210                215 | | 720 |
| caa tct aca ctt agc aat ggt gcg caa ggc ctt gac gta caa gac ttc<br>Gln Ser Thr Leu Ser Asn Gly Ala Gln Gly Leu Asp Val Gln Asp Phe<br>                 220                    225                    230 | | 768 |
| gag gag aac ggc ctt agc gtt tac aac tac aat gcg tac tca ctt tac<br>Glu Glu Asn Gly Leu Ser Val Tyr Asn Tyr Asn Ala Tyr Ser Leu Tyr<br>             235                    240                    245 | | 816 |
| ttc ctt cct gcg aca cgc ttc act caa gag gac atc act gag caa atc<br>Phe Leu Pro Ala Thr Arg Phe Thr Gln Glu Asp Ile Thr Glu Gln Ile<br>         250                      255                  260 | | 864 |
| gac tac atg aag tgg gcg tat gcg tac aac aag ttc ttc tac atc tct<br>Asp Tyr Met Lys Trp Ala Tyr Ala Tyr Asn Lys Phe Phe Tyr Ile Ser<br>265                   270                    275 | | 912 |
| gac tac tac aag caa gta gac aca agc aac gtt aag ggc tct tct ctt<br>Asp Tyr Tyr Lys Gln Val Asp Thr Ser Asn Val Lys Gly Ser Ser Leu<br>280                   285                    290                295 | | 960 |
| gta ttc tgg ggt gag cat gcg aac gac ctt agc caa gag ggc ctt ctt<br>Val Phe Trp Gly Glu His Ala Asn Asp Leu Ser Gln Glu Gly Leu Leu<br>                 300                    305                    310 | | 1008 |
| aag caa gag aag cca ctt atc caa aac ttc ctt ggc ctt<br>Lys Gln Glu Lys Pro Leu Ile Gln Asn Phe Leu Gly Leu<br>315                   320 | | 1047 |

```
<210> SEQ ID NO 4
<211> LENGTH: 349
<212> TYPE: PRT
<213> ORGANISM: Terribacillus goriensis

<400> SEQUENCE: 4

Met Leu Ile Lys Phe Leu Ser Ile Thr Thr Val Ser Ile Leu Leu Phe
-25                 -20                 -15                 -10

Leu Thr Met Ser Asn Thr Ala Gln Ala Gln Asp Gln Glu Lys Gly Ile
                -5                  -1  1                   5

Thr Ile Asp Ile Ser Arg Lys Tyr Tyr Ser Ile Glu Thr Leu Lys Ser
            10                  15                  20

Ile Ile Asp Glu Ile Ser Ala Asn Gly Gly Asp Tyr Leu Gln Leu His
        25                  30                  35

Phe Ser Asp Asn Glu Arg Tyr Ala Ile Ala Ser Glu Phe Leu Gly Gln
40                  45                  50                  55

Asn Gly Glu Asn Pro Asn Ser Thr Tyr Leu Thr Lys Lys Glu Leu Leu
                60                  65                  70

Ser Leu Ile Ala Tyr Ser Asn Asp Arg Asp Ile Met Val Ile Pro Asp
            75                  80                  85

Ile Asp Leu Pro Ala His Ser Arg Gly Trp Leu Asn Ile Met Lys Glu
        90                  95                  100

Lys Asp Ser Gly Leu Tyr Thr Asp Ile Val Thr Asp Tyr Ser Glu Asp
    105                 110                 115

Thr Leu Asp Tyr His Asn Asn Ala Val Ala Leu Tyr Thr Ala Asn Gln
120                 125                 130                 135

Leu Leu Asp Glu Val Leu Asp Leu Phe Tyr Gln Pro Lys Phe Ala Gly
                140                 145                 150

Lys Gln Arg Ile Val Leu Gly Gly Asp Glu Val Pro Gly Ser Gly Val
            155                 160                 165

His Gln Thr Asp Phe Ile Arg Phe Met Asn Gln Ile Ala Glu Thr Ala
        170                 175                 180

Lys Ala Ser Asn Tyr Lys Pro Gln Met Trp Asn Asp Ser Ile Thr Pro
    185                 190                 195

Glu Gly Ile Gln Asn Leu Asp Arg Ser Phe Ser Ile Leu Tyr Trp Lys
200                 205                 210                 215

Gln Ser Thr Leu Ser Asn Gly Ala Gln Gly Leu Asp Val Gln Asp Phe
                220                 225                 230

Glu Glu Asn Gly Leu Ser Val Tyr Asn Tyr Asn Ala Tyr Ser Leu Tyr
            235                 240                 245

Phe Leu Pro Ala Thr Arg Phe Thr Gln Glu Asp Ile Thr Glu Gln Ile
        250                 255                 260

Asp Tyr Met Lys Trp Ala Tyr Ala Tyr Asn Lys Phe Phe Tyr Ile Ser
    265                 270                 275

Asp Tyr Tyr Lys Gln Val Asp Thr Ser Asn Val Lys Gly Ser Ser Leu
280                 285                 290                 295

Val Phe Trp Gly Glu His Ala Asn Asp Leu Ser Gln Glu Gly Leu Leu
                300                 305                 310

Lys Gln Glu Lys Pro Leu Ile Gln Asn Phe Leu Gly Leu
            315                 320

<210> SEQ ID NO 5
<211> LENGTH: 1047
<212> TYPE: DNA
```

```
<213> ORGANISM: Terribacillus saccharophilus
<220> FEATURE:
<221> NAME/KEY: sig_peptide
<222> LOCATION: (1)..(75)
<220> FEATURE:
<221> NAME/KEY: CDS
<222> LOCATION: (1)..(1047)
<220> FEATURE:
<221> NAME/KEY: mat_peptide
<222> LOCATION: (76)..(1047)

<400> SEQUENCE: 5
```

| | | | | | | | | | | | | | | | | |
|---|---|---|---|---|---|---|---|---|---|---|---|---|---|---|---|---|
| atg | ctt | atc | aag | ttc | ctt | tct | atc | act | aca | gtt | tct | atc | ctt | ctt | ttc | 48 |
| Met | Leu | Ile | Lys | Phe | Leu | Ser | Ile | Thr | Thr | Val | Ser | Ile | Leu | Leu | Phe | |
| -25 | | | | -20 | | | | | -15 | | | | | | -10 | |

| | | | | | | | | | | | | | | | | |
|---|---|---|---|---|---|---|---|---|---|---|---|---|---|---|---|---|
| ctt | aca | atg | gcg | aac | act | gcg | caa | gcg | aag | gac | caa | gag | aag | ggc | atc | 96 |
| Leu | Thr | Met | Ala | Asn | Thr | Ala | Gln | Ala | Lys | Asp | Gln | Glu | Lys | Gly | Ile | |
| | | | -5 | | | | -1 | 1 | | | | 5 | | | | |

| | | | | | | | | | | | | | | | | |
|---|---|---|---|---|---|---|---|---|---|---|---|---|---|---|---|---|
| act | atc | gac | atc | tca | cgc | aag | tac | tac | tct | atc | ggc | act | ctt | aaa | gcg | 144 |
| Thr | Ile | Asp | Ile | Ser | Arg | Lys | Tyr | Tyr | Ser | Ile | Gly | Thr | Leu | Lys | Ala | |
| | | 10 | | | | | 15 | | | | | 20 | | | | |

| | | | | | | | | | | | | | | | | |
|---|---|---|---|---|---|---|---|---|---|---|---|---|---|---|---|---|
| atc | gta | gac | gag | atc | aac | gcg | aat | ggt | ggc | gac | tac | ctt | caa | ctt | cac | 192 |
| Ile | Val | Asp | Glu | Ile | Asn | Ala | Asn | Gly | Gly | Asp | Tyr | Leu | Gln | Leu | His | |
| | 25 | | | | | 30 | | | | | 35 | | | | | |

| | | | | | | | | | | | | | | | | |
|---|---|---|---|---|---|---|---|---|---|---|---|---|---|---|---|---|
| ttc | tct | gac | aac | gag | tca | tac | gcg | atc | gcg | tca | gag | ttc | ctt | ggc | caa | 240 |
| Phe | Ser | Asp | Asn | Glu | Ser | Tyr | Ala | Ile | Ala | Ser | Glu | Phe | Leu | Gly | Gln | |
| 40 | | | | | 45 | | | | | 50 | | | | | 55 | |

| | | | | | | | | | | | | | | | | |
|---|---|---|---|---|---|---|---|---|---|---|---|---|---|---|---|---|
| aac | agc | gag | aac | cca | aac | agc | act | tac | ctt | aca | aag | aag | gag | ctt | ctt | 288 |
| Asn | Ser | Glu | Asn | Pro | Asn | Ser | Thr | Tyr | Leu | Thr | Lys | Lys | Glu | Leu | Leu | |
| | | | | 60 | | | | | 65 | | | | | 70 | | |

| | | | | | | | | | | | | | | | | |
|---|---|---|---|---|---|---|---|---|---|---|---|---|---|---|---|---|
| tca | ctt | atc | gcg | tac | agc | aac | gac | cgc | aac | atc | atg | gta | atc | cca | gac | 336 |
| Ser | Leu | Ile | Ala | Tyr | Ser | Asn | Asp | Arg | Asn | Ile | Met | Val | Ile | Pro | Asp | |
| | | | | 75 | | | | | 80 | | | | | 85 | | |

| | | | | | | | | | | | | | | | | |
|---|---|---|---|---|---|---|---|---|---|---|---|---|---|---|---|---|
| atc | gac | ctt | cct | gcg | cac | tca | aag | ggc | tgg | ctt | aac | gta | atg | aag | gag | 384 |
| Ile | Asp | Leu | Pro | Ala | His | Ser | Lys | Gly | Trp | Leu | Asn | Val | Met | Lys | Glu | |
| | | 90 | | | | | 95 | | | | | 100 | | | | |

| | | | | | | | | | | | | | | | | |
|---|---|---|---|---|---|---|---|---|---|---|---|---|---|---|---|---|
| aag | gac | tct | ggc | ctt | tac | aca | gac | atc | gtt | aca | gac | tac | agc | gag | gac | 432 |
| Lys | Asp | Ser | Gly | Leu | Tyr | Thr | Asp | Ile | Val | Thr | Asp | Tyr | Ser | Glu | Asp | |
| | 105 | | | | | 110 | | | | | 115 | | | | | |

| | | | | | | | | | | | | | | | | |
|---|---|---|---|---|---|---|---|---|---|---|---|---|---|---|---|---|
| aca | ctt | gac | tac | cac | aac | aat | gct | gct | gcg | ctt | tac | act | gcg | aac | caa | 480 |
| Thr | Leu | Asp | Tyr | His | Asn | Asn | Ala | Ala | Ala | Leu | Tyr | Thr | Ala | Asn | Gln | |
| 120 | | | | | 125 | | | | | 130 | | | | | 135 | |

| | | | | | | | | | | | | | | | | |
|---|---|---|---|---|---|---|---|---|---|---|---|---|---|---|---|---|
| ctt | ctt | gac | gag | gta | ctt | gac | ctt | ttc | tac | caa | cca | aag | ttt | gct | ggc | 528 |
| Leu | Leu | Asp | Glu | Val | Leu | Asp | Leu | Phe | Tyr | Gln | Pro | Lys | Phe | Ala | Gly | |
| | | | 140 | | | | | 145 | | | | | 150 | | | |

| | | | | | | | | | | | | | | | | |
|---|---|---|---|---|---|---|---|---|---|---|---|---|---|---|---|---|
| aag | caa | cgc | atc | gtt | ctt | ggt | ggc | gac | gag | gta | cca | ggc | tct | ggt | gcg | 576 |
| Lys | Gln | Arg | Ile | Val | Leu | Gly | Gly | Asp | Glu | Val | Pro | Gly | Ser | Gly | Ala | |
| | | | 155 | | | | | 160 | | | | | 165 | | | |

| | | | | | | | | | | | | | | | | |
|---|---|---|---|---|---|---|---|---|---|---|---|---|---|---|---|---|
| cac | caa | aca | gac | ttc | atc | cgc | ttc | atg | aac | caa | atc | gac | gag | act | gcg | 624 |
| His | Gln | Thr | Asp | Phe | Ile | Arg | Phe | Met | Asn | Gln | Ile | Asp | Glu | Thr | Ala | |
| | | 170 | | | | | 175 | | | | | 180 | | | | |

| | | | | | | | | | | | | | | | | |
|---|---|---|---|---|---|---|---|---|---|---|---|---|---|---|---|---|
| aag | gcg | tca | aac | tac | gag | cca | caa | atg | tgg | aac | gac | tct | atc | aca | cca | 672 |
| Lys | Ala | Ser | Asn | Tyr | Glu | Pro | Gln | Met | Trp | Asn | Asp | Ser | Ile | Thr | Pro | |
| | 185 | | | | | 190 | | | | | 195 | | | | | |

| | | | | | | | | | | | | | | | | |
|---|---|---|---|---|---|---|---|---|---|---|---|---|---|---|---|---|
| gag | ggc | atc | caa | aac | ctt | gac | cgc | tca | ttc | agc | atc | ctt | tac | tgg | aag | 720 |
| Glu | Gly | Ile | Gln | Asn | Leu | Asp | Arg | Ser | Phe | Ser | Ile | Leu | Tyr | Trp | Lys | |
| 200 | | | | | 205 | | | | | 210 | | | | | 215 | |

| | | | | | | | | | | | | | | | | |
|---|---|---|---|---|---|---|---|---|---|---|---|---|---|---|---|---|
| caa | tct | act | ctt | agc | tct | ggt | gcg | caa | ggc | ctt | gac | gta | caa | aac | ttc | 768 |
| Gln | Ser | Thr | Leu | Ser | Ser | Gly | Ala | Gln | Gly | Leu | Asp | Val | Gln | Asn | Phe | |
| | | | | 220 | | | | | 225 | | | | | 230 | | |

| | | | | | | | | | | | | | | | | |
|---|---|---|---|---|---|---|---|---|---|---|---|---|---|---|---|---|
| gag | gag | aag | ggc | ttc | tct | gtt | tac | aac | tac | aat | gcg | tac | tct | ctt | tac | 816 |
| Glu | Glu | Lys | Gly | Phe | Ser | Val | Tyr | Asn | Tyr | Asn | Ala | Tyr | Ser | Leu | Tyr | |

```
                235                 240                 245
ttc ctt cct tct aca cgc ttc act cag gag gac atc acg gag caa atc    864
Phe Leu Pro Ser Thr Arg Phe Thr Gln Glu Asp Ile Thr Glu Gln Ile
        250                 255                 260 gac tac atg aag tgg gcg tat gcg tac aac aag ttc ttc tac atc tca    912
Asp Tyr Met Lys Trp Ala Tyr Ala Tyr Asn Lys Phe Phe Tyr Ile Ser
265                 270                 275 gac tac tac aag caa gta gac acg agc aac gta aag ggc agc tca ctt    960
Asp Tyr Tyr Lys Gln Val Asp Thr Ser Asn Val Lys Gly Ser Ser Leu
280                 285                 290                 295 gtt ttc tgg ggt gag cac gcg aac gac ctt tct caa gag ggc ctt ctt   1008
Val Phe Trp Gly Glu His Ala Asn Asp Leu Ser Gln Glu Gly Leu Leu
                300                 305                 310 gag caa gag aag cca ctt atc caa aac ttc ctt tct ctt                1047
Glu Gln Glu Lys Pro Leu Ile Gln Asn Phe Leu Ser Leu
                315                 320
```

<210> SEQ ID NO 6
<211> LENGTH: 349
<212> TYPE: PRT
<213> ORGANISM: Terribacillus saccharophilus

<400> SEQUENCE: 6

```
Met Leu Ile Lys Phe Leu Ser Ile Thr Thr Val Ser Ile Leu Leu Phe
-25                 -20                 -15                 -10

Leu Thr Met Ala Asn Thr Ala Gln Ala Lys Asp Gln Glu Lys Gly Ile
                -5                  -1  1                   5

Thr Ile Asp Ile Ser Arg Lys Tyr Tyr Ser Ile Gly Thr Leu Lys Ala
        10                  15                  20

Ile Val Asp Glu Ile Asn Ala Asn Gly Gly Asp Tyr Leu Gln Leu His
            25                  30                  35

Phe Ser Asp Asn Glu Ser Tyr Ala Ile Ala Ser Glu Phe Leu Gly Gln
40                  45                  50                  55

Asn Ser Glu Asn Pro Asn Ser Thr Tyr Leu Thr Lys Lys Glu Leu Leu
                60                  65                  70

Ser Leu Ile Ala Tyr Ser Asn Asp Arg Asn Ile Met Val Ile Pro Asp
            75                  80                  85

Ile Asp Leu Pro Ala His Ser Lys Gly Trp Leu Asn Val Met Lys Glu
        90                  95                  100

Lys Asp Ser Gly Leu Tyr Thr Asp Ile Val Thr Asp Tyr Ser Glu Asp
    105                 110                 115

Thr Leu Asp Tyr His Asn Asn Ala Ala Ala Leu Tyr Thr Ala Asn Gln
120                 125                 130                 135

Leu Leu Asp Glu Val Leu Asp Leu Phe Tyr Gln Pro Lys Phe Ala Gly
                140                 145                 150

Lys Gln Arg Ile Val Leu Gly Gly Asp Glu Val Pro Gly Ser Gly Ala
            155                 160                 165

His Gln Thr Asp Phe Ile Arg Phe Met Asn Gln Ile Asp Glu Thr Ala
        170                 175                 180

Lys Ala Ser Asn Tyr Glu Pro Gln Met Trp Asn Asp Ser Ile Thr Pro
    185                 190                 195

Glu Gly Ile Gln Asn Leu Asp Arg Ser Phe Ser Ile Leu Tyr Trp Lys
200                 205                 210                 215

Gln Ser Thr Leu Ser Ser Gly Ala Gln Gly Leu Asp Val Gln Asn Phe
                220                 225                 230

Glu Glu Lys Gly Phe Ser Val Tyr Asn Tyr Asn Ala Tyr Ser Leu Tyr
```

```
                    235                 240                 245

Phe Leu Pro Ser Thr Arg Phe Thr Gln Glu Asp Ile Thr Glu Gln Ile
                250                 255                 260

Asp Tyr Met Lys Trp Ala Tyr Ala Tyr Asn Lys Phe Phe Tyr Ile Ser
            265                 270                 275

Asp Tyr Tyr Lys Gln Val Asp Thr Ser Asn Val Lys Gly Ser Ser Leu
280                 285                 290                 295

Val Phe Trp Gly Glu His Ala Asn Asp Leu Ser Gln Glu Gly Leu Leu
                300                 305                 310

Glu Gln Glu Lys Pro Leu Ile Gln Asn Phe Leu Ser Leu
            315                 320

<210> SEQ ID NO 7
<211> LENGTH: 324
<212> TYPE: PRT
<213> ORGANISM: Terribacillus saccharophilus

<400> SEQUENCE: 7

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Ala Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Pro
        275                 280                 285
```

```
Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 8
<211> LENGTH: 324
<212> TYPE: PRT
<213> ORGANISM: Terribacillus goriensis

<400> SEQUENCE: 8

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
            20                  25                  30

Gly Asp Tyr Leu Gln Leu His Phe Ser Asp Asn Glu Arg Tyr Ala Ile
        35                  40                  45

Ala Ser Glu Phe Leu Gly Gln Asn Gly Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu
```

<210> SEQ ID NO 9
<211> LENGTH: 324
<212> TYPE: PRT
<213> ORGANISM: Terribacillus saccharophilus

<400> SEQUENCE: 9

Lys Asp Gln Glu Lys Gly Ile Thr Ile Asp Ile Ser Arg Lys Tyr Tyr
1               5                   10                  15

Ser Ile Gly Thr Leu Lys Ala Ile Val Asp Glu Ile Asn Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Ser Gly Ala Gln
    210                 215                 220

Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Glu Gln Glu Lys Pro Leu Ile Gln Asn
305                 310                 315                 320

Phe Leu Ser Leu

<210> SEQ ID NO 10
<211> LENGTH: 324
<212> TYPE: PRT
<213> ORGANISM: Terribacillus saccharophilus

<400> SEQUENCE: 10

Gln Asp Gln Glu Lys Gly Ile Thr Ile Asp Ile Ser Arg Lys His Tyr
1               5                   10                  15

```
Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys
65                  70                  75                  80

Asp Ile Leu Val Ile Pro Asp Ile Asp Leu Pro Ala His Ser Lys Gly
                85                  90                  95

Trp Leu Glu Leu Ile Lys Lys Asp Val Lys Leu Tyr Asn Asp Ile
                100                 105                 110

Val Thr Asp Tyr Ser Glu Glu Thr Leu Asp Tyr Tyr Asp Asn Arg Val
            115                 120                 125

Ala Leu Asp Thr Val Asn Gln Leu Leu Asp Glu Val Leu Asp Leu Phe
130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
                180                 185                 190

Trp Asn Asp Ser Ile Thr Ser Glu Gly Ile Ala Asn Leu Asp Asp Ser
            195                 200                 205

Phe Ser Ile Leu Tyr Trp Gln Gln Ser Thr Leu Ser Ser Gly Glu Glu
    210                 215                 220

Ser Leu Asn Val Glu Asp Phe Glu Asn Trp Gly Phe Ser Val Tyr Asn
225                 230                 235                 240

Tyr Asn Ala Tyr Ser Leu Tyr Phe Leu Pro Ser Asn Gly Phe Thr Gln
                245                 250                 255

Glu Asp Ile Asn Glu Gln Met Asp Tyr Met Asn Trp Ala Tyr Ala His
                260                 265                 270

Asn Lys Phe Phe Tyr Ile Ser Asp Tyr Tyr His Ala Val Glu Thr Ser
            275                 280                 285

Asn Val Lys Gly Ser Ser Leu Thr Phe Trp Gly Glu His Ala Thr Asp
    290                 295                 300

Leu Ser Gln Lys Lys Leu Leu Lys Gln Glu Leu Pro Leu Ile Arg His
305                 310                 315                 320

Tyr Leu Asn Leu

<210> SEQ ID NO 11
<211> LENGTH: 324
<212> TYPE: PRT
<213> ORGANISM: Terribacillus saccharophilus

<400> SEQUENCE: 11

Lys Asp Gln Glu Lys Gly Ile Ser Ile Asp Ile Ser Arg Lys Tyr Tyr
1               5                   10                  15

Ser Ile Gly Thr Leu Lys Ala Ile Ile Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Asp Tyr Leu Gly Gln Ile Ser Asp Thr Pro Asn Asn Thr Tyr
    50                  55                  60
```

```
Leu Thr Lys Asn Asp Leu Leu Ser Leu Ile Ala Tyr Ser Asn Asp Arg
 65                  70                  75                  80

Asn Ile Leu Ile Ile Pro Asp Met Asp Leu Pro Ala His Ser Arg Gly
                 85                  90                  95

Trp Leu Glu Leu Met Lys Val Lys Asp Arg Glu Leu Tyr Thr Asp Ile
            100                 105                 110

Val Thr Asp Tyr Ser Asn Glu Thr Leu Asp Tyr His Asn Asn Thr Asp
        115                 120                 125

Ala Leu Asn Thr Ala Asn Gln Leu Leu Asn Glu Ile Leu Glu Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Glu Ile His Gln Leu Asp Phe Ile Arg Phe Ile
                165                 170                 175

Asn Gln Ile Ala Ser Thr Ala Lys Ala Ser Asn Tyr Ala Pro Gln Met
            180                 185                 190

Trp Asn Asp Ser Ile Thr Ala Glu Gly Ile Gln Asn Leu Asp Lys Ser
        195                 200                 205

Phe Ser Ile Leu Tyr Trp Lys Gln Ser Thr Leu Ser Asn Gly Ala Gln
210                 215                 220

Ser Leu Glu Val Gln Asp Phe Glu Asp Trp Asp Phe Pro Val Tyr Asn
225                 230                 235                 240

Tyr Asn Ala Tyr Ser Leu Tyr Phe Leu Pro Ser Ile Arg Phe Thr Asp
                245                 250                 255

Glu Asp Ile Thr Glu Gln Met Asn Tyr Met Lys Trp Ala Tyr Ala Tyr
            260                 265                 270

Asn Lys Phe Phe Tyr Ile Ser Asp Tyr Tyr Lys Ser Val Asp Ala Ser
        275                 280                 285

Asn Val Lys Gly Ser Ser Leu Thr Phe Trp Gly Glu His Ala Thr Asp
290                 295                 300

Leu Ser Gln Glu Glu Leu Leu Glu Gln Glu Leu Pro Leu Ile Lys Lys
305                 310                 315                 320

Phe Leu Ser Leu

<210> SEQ ID NO 12
<211> LENGTH: 1047
<212> TYPE: DNA
<213> ORGANISM: Terribacillus saccharophilus
<220> FEATURE:
<221> NAME/KEY: CDS
<222> LOCATION: (1)..(1044)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1044)

<400> SEQUENCE: 12 ttg ttt aaa att ctt tcc att aca gca ctt ggt atg att cta ttt ctg      48
Leu Phe Lys Ile Leu Ser Ile Thr Ala Leu Gly Met Ile Leu Phe Leu
        -20                 -15                 -10 act atg tcg aat aca gtt caa gcc cag gat caa gaa aaa gga att aca      96
Thr Met Ser Asn Thr Val Gln Ala Gln Asp Gln Glu Lys Gly Ile Thr
            -5                  -1   1               5 atc gat att tcg agg aaa cac tat act gtt gaa aca ctg aaa agc ctt     144
Ile Asp Ile Ser Arg Lys His Tyr Thr Val Glu Thr Leu Lys Ser Leu
         10                  15                  20
```

```
gta gat gaa ata agc tat aat ggc ggg aac tac gta cag ctg cat ttt      192
Val Asp Glu Ile Ser Tyr Asn Gly Gly Asn Tyr Val Gln Leu His Phe
 25              30                  35                  40 tcc gat aat gag aat tat gct ata gct tct gaa tat ctt ggt cag agc      240
Ser Asp Asn Glu Asn Tyr Ala Ile Ala Ser Glu Tyr Leu Gly Gln Ser
                 45                  50                  55 agt gag aat acc aat aat aca tat ttg acg aaa aat gaa ctt cta tca      288
Ser Glu Asn Thr Asn Asn Thr Tyr Leu Thr Lys Asn Glu Leu Leu Ser
             60                  65                  70 tta ata gca tat agt aat gat aaa gat ata ctg gtc att cct gat att      336
Leu Ile Ala Tyr Ser Asn Asp Lys Asp Ile Leu Val Ile Pro Asp Ile
         75                  80                  85 gat ctg ccg gcg cac tcc aag ggg tgg ctg gaa tta atc aaa aag aaa      384
Asp Leu Pro Ala His Ser Lys Gly Trp Leu Glu Leu Ile Lys Lys Lys
     90                  95                 100 gat gtg aag tta tat aat gac atc gta acg gat tac agc gaa gag aca      432
Asp Val Lys Leu Tyr Asn Asp Ile Val Thr Asp Tyr Ser Glu Glu Thr
105                 110                 115                 120 ctg gat tat tat gat aat aga gtc gca ttg gat act gtg aat cag ctg      480
Leu Asp Tyr Tyr Asp Asn Arg Val Ala Leu Asp Thr Val Asn Gln Leu
                125                 130                 135 ttg gat gaa gtg ctt gat ttg ttt tat cag cca aaa ttc gaa gga aaa      528
Leu Asp Glu Val Leu Asp Leu Phe Tyr Gln Pro Lys Phe Glu Gly Lys
            140                 145                 150 caa aga ata gtg ctt ggc ggg gat gaa gta tcg gga agt gaa gtg cat      576
Gln Arg Ile Val Leu Gly Gly Asp Glu Val Ser Gly Ser Glu Val His
        155                 160                 165 cag ttg gat ttt att gat ttt atg aat cag att gcc agt aca gtc aaa      624
Gln Leu Asp Phe Ile Asp Phe Met Asn Gln Ile Ala Ser Thr Val Lys
    170                 175                 180 gaa agc aaa tat gaa ccg caa atg tgg aat gac agc atc acg tca gaa      672
Glu Ser Lys Tyr Glu Pro Gln Met Trp Asn Asp Ser Ile Thr Ser Glu
185                 190                 195                 200 gga ata gcg aac ttg gac gat agc ttt tcc atc ctc tat tgg cag caa      720
Gly Ile Ala Asn Leu Asp Asp Ser Phe Ser Ile Leu Tyr Trp Gln Gln
                205                 210                 215 agt aca ctt tcc agc gga gaa gaa agc ttg aat gtg gag gac ttt gaa      768
Ser Thr Leu Ser Ser Gly Glu Glu Ser Leu Asn Val Glu Asp Phe Glu
            220                 225                 230 aac tgg ggt ttc tcc gta tat aac tat aat gca tat tct ttg tac ttc      816
Asn Trp Gly Phe Ser Val Tyr Asn Tyr Asn Ala Tyr Ser Leu Tyr Phe
        235                 240                 245 tta cca tca aac ggg ttt aca cag gaa gat atc aat gag cag atg gat      864
Leu Pro Ser Asn Gly Phe Thr Gln Glu Asp Ile Asn Glu Gln Met Asp
    250                 255                 260 tat atg aat tgg gct tat gcg cat aat aaa ttt ttc tat att tca gat      912
Tyr Met Asn Trp Ala Tyr Ala His Asn Lys Phe Phe Tyr Ile Ser Asp
265                 270                 275                 280 tac tat cat gcg gtg gaa act tct aat gta aaa ggt tca agt ctg acc      960
Tyr Tyr His Ala Val Glu Thr Ser Asn Val Lys Gly Ser Ser Leu Thr
                285                 290                 295 ttt tgg ggc gaa cat gca act gac ttg agc caa aag aaa tta tta aag     1008
Phe Trp Gly Glu His Ala Thr Asp Leu Ser Gln Lys Lys Leu Leu Lys
            300                 305                 310 caa gag ctg cct ttg ata aga cat tat ctg aac ttg taa                 1047
Gln Glu Leu Pro Leu Ile Arg His Tyr Leu Asn Leu
        315                 320
```

<210> SEQ ID NO 13

```
<211> LENGTH: 348
<212> TYPE: PRT
<213> ORGANISM: Terribacillus saccharophilus

<400> SEQUENCE: 13

Leu Phe Lys Ile Leu Ser Ile Thr Ala Leu Gly Met Ile Leu Phe Leu
            -20                 -15                 -10

Thr Met Ser Asn Thr Val Gln Ala Gln Asp Gln Glu Lys Gly Ile Thr
             -5              -1   1                   5

Ile Asp Ile Ser Arg Lys His Tyr Thr Val Glu Thr Leu Lys Ser Leu
 10                  15                  20

Val Asp Glu Ile Ser Tyr Asn Gly Gly Asn Tyr Val Gln Leu His Phe
 25                  30                  35                  40

Ser Asp Asn Glu Asn Tyr Ala Ile Ala Ser Glu Tyr Leu Gly Gln Ser
                 45                  50                  55

Ser Glu Asn Thr Asn Asn Thr Tyr Leu Thr Lys Asn Glu Leu Leu Ser
             60                  65                  70

Leu Ile Ala Tyr Ser Asn Asp Lys Asp Ile Leu Val Ile Pro Asp Ile
             75                  80                  85

Asp Leu Pro Ala His Ser Lys Gly Trp Leu Glu Leu Ile Lys Lys Lys
 90                  95                 100

Asp Val Lys Leu Tyr Asn Asp Ile Val Thr Asp Tyr Ser Glu Glu Thr
105                 110                 115                 120

Leu Asp Tyr Tyr Asp Asn Arg Val Ala Leu Asp Thr Val Asn Gln Leu
                125                 130                 135

Leu Asp Glu Val Leu Asp Leu Phe Tyr Gln Pro Lys Phe Glu Gly Lys
            140                 145                 150

Gln Arg Ile Val Leu Gly Gly Asp Glu Val Ser Gly Ser Glu Val His
            155                 160                 165

Gln Leu Asp Phe Ile Asp Phe Met Asn Gln Ile Ala Ser Thr Val Lys
            170                 175                 180

Glu Ser Lys Tyr Glu Pro Gln Met Trp Asn Asp Ser Ile Thr Ser Glu
185                 190                 195                 200

Gly Ile Ala Asn Leu Asp Asp Ser Phe Ser Ile Leu Tyr Trp Gln Gln
                205                 210                 215

Ser Thr Leu Ser Ser Gly Glu Glu Ser Leu Asn Val Glu Asp Phe Glu
            220                 225                 230

Asn Trp Gly Phe Ser Val Tyr Asn Tyr Asn Ala Tyr Ser Leu Tyr Phe
            235                 240                 245

Leu Pro Ser Asn Gly Phe Thr Gln Glu Asp Ile Asn Glu Gln Met Asp
            250                 255                 260

Tyr Met Asn Trp Ala Tyr Ala His Asn Lys Phe Phe Tyr Ile Ser Asp
265                 270                 275                 280

Tyr Tyr His Ala Val Glu Thr Ser Asn Val Lys Gly Ser Ser Leu Thr
                285                 290                 295

Phe Trp Gly Glu His Ala Thr Asp Leu Ser Gln Lys Leu Leu Lys
            300                 305                 310

Gln Glu Leu Pro Leu Ile Arg His Tyr Leu Asn Leu
            315                 320

<210> SEQ ID NO 14
<211> LENGTH: 1047
<212> TYPE: DNA
<213> ORGANISM: Terribacillus saccharophilus
<220> FEATURE:
<221> NAME/KEY: CDS
```

```
<222> LOCATION: (1)..(1044)
<220> FEATURE:
<221> NAME/KEY: sig_peptide
<222> LOCATION: (1)..(72)
<220> FEATURE:
<221> NAME/KEY: mat_peptide
<222> LOCATION: (73)..(1044)

<400> SEQUENCE: 14 ttg att aaa ttt ctt tct att aca aca gtt agt ata ctc tta ttt cta      48
Leu Ile Lys Phe Leu Ser Ile Thr Thr Val Ser Ile Leu Leu Phe Leu
            -20                 -15                 -10 act atg gcg aat aca gta cat gca aag gat caa gag aaa ggg att tca      96
Thr Met Ala Asn Thr Val His Ala Lys Asp Gln Glu Lys Gly Ile Ser
        -5                  -1  1                   5 atc gat att tcg aga aaa tat tat tct atc gga aca tta aaa gca att     144
Ile Asp Ile Ser Arg Lys Tyr Tyr Ser Ile Gly Thr Leu Lys Ala Ile
        10                  15                  20 ata gat gaa ata agt gca aat ggc gga gac tac tta cag ctg cat ttt     192
Ile Asp Glu Ile Ser Ala Asn Gly Gly Asp Tyr Leu Gln Leu His Phe
25                  30                  35                  40 tca gat aat gag agc tat gca att gct tct gac tat ctt ggt cag atc     240
Ser Asp Asn Glu Ser Tyr Ala Ile Ala Ser Asp Tyr Leu Gly Gln Ile
                45                  50                  55 agt gat act cct aac aat aca tac tta acg aaa aat gat ctt tta tca     288
Ser Asp Thr Pro Asn Asn Thr Tyr Leu Thr Lys Asn Asp Leu Leu Ser
            60                  65                  70 ctt ata gca tat agc aat gat aga aat ata ctg atc att ccc gat atg     336
Leu Ile Ala Tyr Ser Asn Asp Arg Asn Ile Leu Ile Ile Pro Asp Met
        75                  80                  85 gat cta cct gcg cat tcc aga ggc tgg ttg gag tta atg aaa gtg aaa     384
Asp Leu Pro Ala His Ser Arg Gly Trp Leu Glu Leu Met Lys Val Lys
    90                  95                  100 gat aga gaa tta tat act gac att gta acg gat tac agt aac gag aca     432
Asp Arg Glu Leu Tyr Thr Asp Ile Val Thr Asp Tyr Ser Asn Glu Thr
105                 110                 115                 120 ctt gat tat cat aat aat aca gat gct cta aat act gcg aat cag ctg     480
Leu Asp Tyr His Asn Asn Thr Asp Ala Leu Asn Thr Ala Asn Gln Leu
                125                 130                 135 tta aat gaa ata ctt gaa cta ttt tat cag cca aag ttt gcg ggg aag     528
Leu Asn Glu Ile Leu Glu Leu Phe Tyr Gln Pro Lys Phe Ala Gly Lys
            140                 145                 150 cag agg ata gta ctt ggc gga gat gaa gtg cca ggg agt gag att cat     576
Gln Arg Ile Val Leu Gly Gly Asp Glu Val Pro Gly Ser Glu Ile His
        155                 160                 165 cag ttg gat ttc att cgt ttt att aat caa atc gcc tcc act gct aaa     624
Gln Leu Asp Phe Ile Arg Phe Ile Asn Gln Ile Ala Ser Thr Ala Lys
    170                 175                 180 gct agc aac tat gca cca cag atg tgg aat gat agc att act gca gaa     672
Ala Ser Asn Tyr Ala Pro Gln Met Trp Asn Asp Ser Ile Thr Ala Glu
185                 190                 195                 200 gga att cag aat ctg gat aaa agc ttc tct att ctt tat tgg aag caa     720
Gly Ile Gln Asn Leu Asp Lys Ser Phe Ser Ile Leu Tyr Trp Lys Gln
                205                 210                 215 agt acg ctt tca aac ggt gca caa agt cta gaa gta caa gac ttt gaa     768
Ser Thr Leu Ser Asn Gly Ala Gln Ser Leu Glu Val Gln Asp Phe Glu
            220                 225                 230 gac tgg gat ttt ccc gta tat aac tat aat gca tat tct tta tat ttc     816
Asp Trp Asp Phe Pro Val Tyr Asn Tyr Asn Ala Tyr Ser Leu Tyr Phe
        235                 240                 245 tta cct tcc atc cgt ttt acc gat gaa gat ata aca gag cag atg aac     864
Leu Pro Ser Ile Arg Phe Thr Asp Glu Asp Ile Thr Glu Gln Met Asn
```

-continued

```
Leu Pro Ser Ile Arg Phe Thr Asp Glu Asp Ile Thr Glu Gln Met Asn
    250                 255                 260 tat atg aaa tgg gct tat gca tat aat aaa ttt ttc tat att tca gat       912
Tyr Met Lys Trp Ala Tyr Ala Tyr Asn Lys Phe Phe Tyr Ile Ser Asp
265                 270                 275                 280 tac tat aag tcg gtg gac gca tct aac gta aaa ggg tct agc ttg acc       960
Tyr Tyr Lys Ser Val Asp Ala Ser Asn Val Lys Gly Ser Ser Leu Thr
                285                 290                 295 ttt tgg ggt gaa cac gca act gac tta agc caa gag gaa ttg ctt gag      1008
Phe Trp Gly Glu His Ala Thr Asp Leu Ser Gln Glu Glu Leu Leu Glu
            300                 305                 310 caa gaa ctg cct tta ata aaa aaa ttc tta agc tta taa                  1047
Gln Glu Leu Pro Leu Ile Lys Lys Phe Leu Ser Leu
        315                 320

<210> SEQ ID NO 15
<211> LENGTH: 348
<212> TYPE: PRT
<213> ORGANISM: Terribacillus saccharophilus

<400> SEQUENCE: 15

Leu Ile Lys Phe Leu Ser Ile Thr Thr Val Ser Ile Leu Leu Phe Leu
                -20                 -15                 -10

Thr Met Ala Asn Thr Val His Ala Lys Asp Gln Glu Lys Gly Ile Ser
            -5                  -1  1                   5

Ile Asp Ile Ser Arg Lys Tyr Tyr Ser Ile Gly Thr Leu Lys Ala Ile
 10                  15                  20

Ile Asp Glu Ile Ser Ala Asn Gly Gly Asp Tyr Leu Gln Leu His Phe
25                  30                  35                  40

Ser Asp Asn Glu Ser Tyr Ala Ile Ala Ser Asp Tyr Leu Gly Gln Ile
                45                  50                  55

Ser Asp Thr Pro Asn Asn Thr Tyr Leu Thr Lys Asn Asp Leu Leu Ser
            60                  65                  70

Leu Ile Ala Tyr Ser Asn Asp Arg Asn Ile Leu Ile Pro Asp Met
        75                  80                  85

Asp Leu Pro Ala His Ser Arg Gly Trp Leu Glu Leu Met Lys Val Lys
 90                  95                 100

Asp Arg Glu Leu Tyr Thr Asp Ile Val Thr Asp Tyr Ser Asn Glu Thr
105                 110                 115                 120

Leu Asp Tyr His Asn Asn Thr Asp Ala Leu Asn Thr Ala Asn Gln Leu
                125                 130                 135

Leu Asn Glu Ile Leu Glu Leu Phe Tyr Gln Pro Lys Phe Ala Gly Lys
            140                 145                 150

Gln Arg Ile Val Leu Gly Gly Asp Glu Val Pro Gly Ser Glu Ile His
        155                 160                 165

Gln Leu Asp Phe Ile Arg Phe Ile Asn Gln Ile Ala Ser Thr Ala Lys
    170                 175                 180

Ala Ser Asn Tyr Ala Pro Gln Met Trp Asn Asp Ser Ile Thr Ala Glu
185                 190                 195                 200

Gly Ile Gln Asn Leu Asp Lys Ser Phe Ser Ile Leu Tyr Trp Lys Gln
                205                 210                 215

Ser Thr Leu Ser Asn Gly Ala Gln Ser Leu Glu Val Gln Asp Phe Glu
            220                 225                 230

Asp Trp Asp Phe Pro Val Tyr Asn Tyr Asn Ala Tyr Ser Leu Tyr Phe
        235                 240                 245

Leu Pro Ser Ile Arg Phe Thr Asp Glu Asp Ile Thr Glu Gln Met Asn
```

```
                250                 255                 260
Tyr Met Lys Trp Ala Tyr Ala Tyr Asn Lys Phe Phe Tyr Ile Ser Asp
265                 270                 275                 280

Tyr Tyr Lys Ser Val Asp Ala Ser Asn Val Lys Gly Ser Ser Leu Thr
                285                 290                 295

Phe Trp Gly Glu His Ala Thr Asp Leu Ser Gln Glu Glu Leu Leu Glu
                300                 305                 310

Gln Glu Leu Pro Leu Ile Lys Lys Phe Leu Ser Leu
                315                 320
```

<210> SEQ ID NO 16
<211> LENGTH: 27
<212> TYPE: PRT
<213> ORGANISM: Artificial
<220> FEATURE:
<223> OTHER INFORMATION: Bacillus clausii signal peptide

<400> SEQUENCE: 16

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
                20                  25
```

<210> SEQ ID NO 17
<211> LENGTH: 8
<212> TYPE: PRT
<213> ORGANISM: Artificial
<220> FEATURE:
<223> OTHER INFORMATION: His-tag

<400> SEQUENCE: 17

```
His His His His His His Pro Arg
1               5
```

<210> SEQ ID NO 18
<211> LENGTH: 4
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa = any natural amino acids

<400> SEQUENCE: 18

```
Gly Xaa Asp Glu
1
```

<210> SEQ ID NO 19
<211> LENGTH: 7
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = E (Glu) or Q (Gln)
<220> FEATURE:
<221> NAME/KEY: MISC_FEATURE
<222> LOCATION: (2)..(2)
<223> OTHER INFORMATION: Xaa = N (Asn) or R (Arg) or S (Ser) or H (His)
     or A (Ala)
<220> FEATURE:
<221> NAME/KEY: MISC_FEATURE
<222> LOCATION: (3)..(3)

```
<223> OTHER INFORMATION: Xaa = Y (Tyr) or V (Val) or F (Phe) or L (Leu)
<220> FEATURE:
<221> NAME/KEY: MISC_FEATURE
<222> LOCATION: (4)..(4)
<223> OTHER INFORMATION: Xaa = A(Ala) or G(Gly) or S (Ser) or T (Thr) or
      C (Cys)
<220> FEATURE:
<221> NAME/KEY: MISC_FEATURE
<222> LOCATION: (5)..(5)
<223> OTHER INFORMATION: Xaa = I (Ile) or V (Val) or L (Leu) or F (Phe)
<220> FEATURE:
<221> NAME/KEY: MISC_FEATURE
<222> LOCATION: (6)..(6)
<223> OTHER INFORMATION: Xaa = E (Glu) or A (Ala) or Q (Gln) or Y (Tyr)
      or N (Asn)
<220> FEATURE:
<221> NAME/KEY: MISC_FEATURE
<222> LOCATION: (7)..(7)
<223> OTHER INFORMATION: Xaa = S (Ser) or N (Asn)

<400> SEQUENCE: 19

Xaa Xaa Xaa Xaa Xaa Xaa Xaa
1               5

<210> SEQ ID NO 20
<211> LENGTH: 8
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = V (Val) or I (Ile) or M (Met)
<220> FEATURE:
<221> NAME/KEY: MISC_FEATURE
<222> LOCATION: (2)..(2)
<223> OTHER INFORMATION: Xaa = L (Leu) or I (Ile) or V (Val)
<220> FEATURE:
<221> NAME/KEY: MISC_FEATURE
<222> LOCATION: (4)..(4)
<223> OTHER INFORMATION: Xaa = G (Gly) or A (Ala) or V (Val)
<220> FEATURE:
<221> NAME/KEY: MISC_FEATURE
<222> LOCATION: (7)..(7)
<223> OTHER INFORMATION: Xaa = V (Val) or I (Ile)
<220> FEATURE:
<221> NAME/KEY: MISC_FEATURE
<222> LOCATION: (8)..(8)
<223> OTHER INFORMATION: Xaa = P (Pro) or S (Ser) or A (Ala)

<400> SEQUENCE: 20

Xaa Xaa Gly Xaa Asp Glu Xaa Xaa
1               5

<210> SEQ ID NO 21
<211> LENGTH: 6
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: Xaa = S (Ser) or Q (Gln) or R (Arg)
<220> FEATURE:
<221> NAME/KEY: MISC_FEATURE
<222> LOCATION: (5)..(5)
<223> OTHER INFORMATION: Xaa = I (Ile) or V (Val) or L (Leu)
<220> FEATURE:
<221> NAME/KEY: MISC_FEATURE
<222> LOCATION: (6)..(6)
<223> OTHER INFORMATION: Xaa = T (Thr) or L (Leu) or V (Val) or M (Met)

<400> SEQUENCE: 21
```

```
Trp Asn Asp Xaa Xaa Xaa
1               5

<210> SEQ ID NO 22
<211> LENGTH: 4
<212> TYPE: PRT
<213> ORGANISM: Artificial
<220> FEATURE:
<223> OTHER INFORMATION: motif

<400> SEQUENCE: 22

Gln Ser Thr Leu
1

<210> SEQ ID NO 23
<211> LENGTH: 5
<212> TYPE: PRT
<213> ORGANISM: Artificial
<220> FEATURE:
<223> OTHER INFORMATION: motif

<400> SEQUENCE: 23

Asn Lys Phe Phe Tyr
1               5

<210> SEQ ID NO 24
<211> LENGTH: 5
<212> TYPE: PRT
<213> ORGANISM: Artificial
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: Xaa = D (Asp) or R (Arg)

<400> SEQUENCE: 24

Asn Leu Asp Xaa Ser
1               5
```